US012773134B2

(12) United States Patent
Rong et al.

(10) Patent No.: US 12,773,134 B2
(45) Date of Patent: Oct. 27, 2026

(54) CONTINUOUS ANALYTE MONITORING SENSOR SYSTEMS AND METHODS OF USING THE SAME

(71) Applicant: Dexcom, Inc., San Diego, CA (US)

(72) Inventors: Daiting Rong, San Diego, CA (US); Xiong Peng, San Diego, CA (US); Nicholas Vincent Apollo, San Diego, CA (US); Jonathan M Hughes, Carlsbad, CA (US); Wenjie Lan, San Diego, CA (US); Chris W Dring, San Diego, CA (US); Shane Richard Parnell, San Diego, CA (US); Ryan Lee Knoy, San Diego, CA (US); Peter C Simpson, Cardiff, CA (US); Joshua Ray Windmiller, Del Mar, CA (US); Nai-Jen Chang, San Diego, CA (US); Jie Zhu, Carlsbad, CA (US); Matthew S. Brown, San Diego, CA (US); Eric Ruike Zhao, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 475 days.

(21) Appl. No.: 18/185,455

(22) Filed: Mar. 17, 2023

(65) Prior Publication Data

US 2023/0301553 A1 Sep. 28, 2023

Related U.S. Application Data

(60) Provisional application No. 63/478,047, filed on Dec. 30, 2022, provisional application No. 63/321,340, filed on Mar. 18, 2022.

(51) Int. Cl.
*A61B 5/145* (2006.01)
*A61B 5/1486* (2006.01)
(Continued)

(52) U.S. Cl.
CPC ........ *A61B 5/1451* (2013.01); *A61B 5/14532* (2013.01); *A61B 5/14542* (2013.01);
(Continued)

(58) Field of Classification Search
CPC .............. A61B 5/1451; A61B 5/14532; A61B 5/14542; A61B 5/14865; A61B 5/14546; A61B 5/1495; A61B 5/1486
See application file for complete search history.

(56) References Cited

U.S. PATENT DOCUMENTS 4,340,457 A 7/1982 Kater
5,338,435 A 8/1994 Betts et al.
(Continued)

FOREIGN PATENT DOCUMENTS

CN 103549963 A 2/2014
EP 3902472 B1 8/2025
(Continued)

OTHER PUBLICATIONS

Bisenberger, M., C. Bräuchle, and N. Hampp. "A triple-step potential waveform at enzyme multisensors with thick-film gold electrodes for detection of glucose and sucrose." (1995). Sensors and Actuators B: Chemical 28.3: 181-189. (Year: 1995).*
(Continued)

*Primary Examiner* — Jason M Sims
*Assistant Examiner* — Kyle W. Kretzer
(74) *Attorney, Agent, or Firm* — Schwegman, Lundberg & Woessner, P.A.

(57) ABSTRACT

Disclosed herein are systems and methods for a continuous analyte monitoring system for measuring a concentration of a first analyte and concentration of a second analyte in a host. One such system utilizes a working electrode and a reference electrode to measure glucose concentration and oxygen concentration in bodily fluid of a host. The system
(Continued)

includes a sensor control circuit that applies a first bias condition to the sensor to measure a first signal generated by the sensor indicative of a concentration of the first analyte. The sensor control circuit also applies a second bias condition to the sensor to measure a second signal generated by the sensor indicative of a concentration of a second analyte at the host.

22 Claims, 35 Drawing Sheets

(51) Int. Cl.
*A61B 5/256* (2021.01)
*A61B 5/257* (2021.01)

(52) U.S. Cl.
CPC ...... *A61B 5/14865* (2013.01); *A61B 5/14546* (2013.01); *A61B 5/256* (2021.01); *A61B 5/257* (2021.01)

(56) References Cited

U.S. PATENT DOCUMENTS 5,918,590 A 7/1999 Burkett et al.
6,001,067 A 12/1999 Shults et al.
6,424,847 B1 7/2002 Mastrototaro et al.
6,477,395 B2 11/2002 Schulman et al.
6,484,046 B1 11/2002 Say et al.
6,512,939 B1 1/2003 Colvin et al.
6,565,509 B1 5/2003 Say et al.
6,579,690 B1 6/2003 Bonnecaze et al.
7,494,465 B2 2/2009 Brister et al.
8,682,408 B2 3/2014 Boock et al.
9,044,199 B2 6/2015 Brister et al.
9,170,310 B2 10/2015 Ma et al.
2005/0027463 A1 2/2005 Goode, Jr. et al.
2005/0161346 A1 7/2005 Simpson et al.
2005/0179512 A1 8/2005 Weyers et al.
2006/0020187 A1 1/2006 Brister et al.
2006/0195029 A1* 8/2006 Shults .................. A61B 5/6848 128/903
2007/0027385 A1 2/2007 Brister et al.
2007/0128681 A1 6/2007 Barman et al.
2007/0173710 A1 7/2007 Petisce et al.
2007/0197890 A1 8/2007 Boock et al.
2008/0108942 A1 5/2008 Brister et al.
2008/0119703 A1 5/2008 Brister et al.
2009/0178459 A1* 7/2009 Li .......................... C12Q 1/001 73/1.02
2010/0292557 A1 11/2010 Pesach et al.
2011/0024307 A1 2/2011 Simpson et al.
2011/0144463 A1 6/2011 Pesach et al.
2012/0004524 A1 1/2012 Van Antwerp et al.
2012/0028805 A1 2/2012 Hollis et al.
2012/0078071 A1* 3/2012 Bohm .................. A61B 5/0002 600/345
2012/0262298 A1 10/2012 Bohm et al.
2013/0245981 A1 9/2013 Estes et al.
2014/0005505 A1 1/2014 Peyser et al.
2014/0005509 A1* 1/2014 Bhavaraju ............ A61B 5/1459 600/347
2015/0087941 A1 3/2015 Katsuki
2015/0289788 A1 10/2015 Simpson et al.
2015/0351672 A1 12/2015 Vanslyke et al.
2016/0058380 A1 3/2016 Lee et al.
2016/0151010 A1 6/2016 Erez
2016/0235366 A1 8/2016 Holmes et al.
2017/0273610 A1* 9/2017 Suri ................... A61B 5/15105
2018/0151280 A1 5/2018 Pourrahimi
2018/0279928 A1 10/2018 Bohm et al.
2018/0325430 A1 11/2018 Vaddiraju et al.
2018/0353684 A1 12/2018 Kim et al.
2018/0372667 A1 12/2018 Gupta
2019/0175082 A1* 6/2019 Varsavsky ............ A61B 5/4839
2019/0227022 A1 7/2019 Harley-Trochimczyk et al.

FOREIGN PATENT DOCUMENTS

WO 2004059286 A2 7/2004
WO 2020140017 A1 7/2020

OTHER PUBLICATIONS

International Search Report and Written Opinion for Application No. PCT/US2023/015493, mailed Aug. 14, 2023, 28 pages.
International Search Report and Written Opinion for Application No. PCT/US2019/068708 mailed on Apr. 30, 2020, 11 pages.

* cited by examiner

Exponential 3P

Prediction Model a+b • Exp © • Time (s))

a = Asymptote
b = Scale
c = Growth Rate

Summary of Fit

Parameter Estimates

| Parameter | Estimate | Std Error | Wald ChiSquare | Prob > ChiSquare | Lower 95% | Upper 95% |
|---|---|---|---|---|---|---|
| Asymptote | 7.0890431 | 0.220365 | 1034.8798 | <.0001* | 6.6571356 | 7.5209506 |
| Scale | 0.9272675 | 0.1878589 | 24.363884 | <.0001* | 0.5590708 | 1.2954641 |
| Growth Rate | -0.005171 | 0.0024543 | 4.4397 | 0.0351* | -0.009982 | -0.000361 |

CONTINUOUS ANALYTE MONITORING SENSOR SYSTEMS AND METHODS OF USING THE SAME

CROSS-REFERENCE TO RELATED APPLICATION

This application claims priority to and the benefit of U.S. Provisional Patent Application Ser. No. 63/321,340, filed Mar. 18, 2022, entitled "CONTINUOUS ANALYTE MONITORING SENSOR SYSTEMS AND METHODS OF USING THE SAME," and claims priority to and the benefit of U.S. Provisional Patent Application Ser. No. 63/478,047, filed Dec. 30, 2022, entitled "CONTINUOUS ANALYTE MONITORING SENSOR SYSTEMS AND METHODS OF USING THE SAME," both of which are hereby incorporated by reference in their entirety.

FIELD

The present disclosure relates generally to systems and methods for measuring analyte concentrations in a host.

BACKGROUND

Monitoring of various systems functioning in a host can be helpful to monitor the overall health of the host. As an example, continuous monitoring of analytes associated with diabetes can help a patient monitor their health. Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a blood sugar level higher than what is considered normal or healthy is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2." A Type 1 diabetes patient may be able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with a continuous analyte monitoring system, such as a continuous glucose monitor. A continuous glucose monitor may provide the wearer (patient) with information, such as an estimated blood glucose level or a trend of estimated blood glucose levels.

SUMMARY

Example 1 is a continuous analyte monitoring system for measuring a concentration of a first analyte and concentration of a second analyte in a host, the continuous analyte monitoring system comprising: a sensor comprising a working electrode extending along a central axis; and a reference electrode; and a sensor control circuit, the sensor control circuit configured to perform operations comprising: applying a first bias condition to the sensor; accessing a first signal generated by the sensor in vivo while the first bias condition is applied to the sensor, the first signal indicating a concentration of a first analyte at the host; applying a second bias condition to the sensor, the second bias condition being different than the first bias condition; and accessing, by the sensor control circuit, a second signal generated by the sensor in vivo while the second bias condition is applied to the sensor, the second signal indicating a concentration of a second analyte at the host, the second analyte being different than the first analyte.

In Example 2, which can be combined with other examples herein, the subject matter of Example 1 optionally includes wherein the first analyte is glucose and the second analyte is oxygen.

In Example 3, which can be combined with other examples herein, the subject matter of any one or more of Examples 1-2 optionally includes wherein the reference electrode is configured to support a redox reaction the working electrode is configured to support an oxidation reaction.

In Example 4, which can be combined with other examples herein, the subject matter of any one or more of Examples 1-3 optionally includes wherein the reference electrode extends coaxially along the central axis.

In Example 5, which can be combined with other examples herein, the subject matter of any one or more of Examples 1-4 optionally includes wherein the reference electrode is configured to operate in an ex vivo position.

In Example 6, which can be combined with other examples herein, the subject matter of any one or more of Examples 1-5 optionally includes wherein the working electrode, the reference electrode, or both are substantially planar.

In Example 7, which can be combined with other examples herein, the subject matter of any one or more of Examples 1-6 optionally includes a counter electrode in electrical communication with the working electrode, the reference electrode, or both.

In Example 8, which can be combined with other examples herein, the subject matter of any one or more of Examples 1-7 optionally includes an enzyme layer at least partially covering the working electrode.

In Example 9, which can be combined with other examples herein, the subject matter of Example 8 optionally includes wherein the enzyme layer comprises an oxidase.

In Example 10, which can be combined with other examples herein, the subject matter of any one or more of Examples 8-9 optionally includes a resistance layer at least partially covering the enzyme layer.

In Example 11, which can be combined with other examples herein, the subject matter of any one or more of Examples 1-10 optionally includes wherein the working electrode comprises platinum and tantalum, and the reference electrode comprises silver and silver chloride.

In Example 12, which can be combined with other examples herein, the subject matter of any one or more of Examples 1-11 optionally includes wherein at least a portion of the working electrode and the reference electrode are configured to be exposed to at least one of glucose or oxygen.

In Example 13, which can be combined with other examples herein, the subject matter of any one or more of Examples 1-12 optionally includes wherein buckling strength of the sensor is in a range of 0.010 lbf to 0.10 lbf.

In Example 14, which can be combined with other examples herein, the subject matter of any one or more of Examples 1-13 optionally includes wherein: when configured in the first bias condition, the working electrode is biased at about 0.50 V to about 0.70 V, relative to the reference electrode; and when configured in the second bias condition, the working electrode is biased at about −0.3V to about −0.2V, relative to the reference electrode.

In Example 15, which can be combined with other examples herein, the subject matter of any one or more of Examples 1-14 optionally includes a transmitter capable of transmitting data obtained during the first bias condition, the second bias condition, or both to a device.

Example 16, which can be combined with other examples herein, is a method of continuous analyte monitoring, the method comprising: biasing an in vivo sensor, by a sensor control circuit, to a first bias condition, the sensor comprising: a working electrode extending coaxially along a central axis; and a reference electrode; accessing, by the sensor control circuit, a first signal generated by the sensor while the first bias condition is applied to the sensor, the first signal indicating a concentration of a first analyte; biasing the sensor, by the sensor control circuit, to a second bias condition different than the first bias condition; and accessing, by the sensor control circuit, a second signal generated by the sensor while the second bias condition is applied to the sensor, the second signal indicating a concentration of a second analyte, the second analyte being different than the first analyte.

In Example 17, which can be combined with other examples herein, the subject matter of Example 16 optionally includes wherein the first bias condition has a first polarity and the second bias condition has a second polarity that is the opposite of the first polarity.

In Example 18, which can be combined with other examples herein, the subject matter of any one or more of Examples 16-17 optionally includes wherein the biasing of the sensor to the first bias condition comprises applying a positive potential difference between the working electrode and the reference electrode.

In Example 19, which can be combined with other examples herein, the subject matter of Example 18 optionally includes wherein the positive potential difference is in a range of from about 0.50 V to 0.70 V.

In Example 20, which can be combined with other examples herein, the subject matter of any one or more of Examples 16-19 optionally includes wherein the biasing of the sensor to the second bias condition comprises applying a negative potential difference between the working electrode and the reference electrode.

In Example 21, which can be combined with other examples herein, the subject matter of Example 20 wherein the negative potential difference is in a range of from about −0.3 to −0.2V In Example 22, which can be combined with other examples herein, the subject matter of any one or more of Examples 16-21 optionally includes wherein the sensor is configured to reside in vivo.

In Example 23, which can be combined with other examples herein, the subject matter of any one or more of Examples 16-22 optionally includes switching the sensor between first bias condition and the second bias condition.

In Example 24, which can be combined with other examples herein, the subject matter of Example 23 optionally includes wherein switching between the first bias condition and the second bias condition comprises executing a first bias condition program and a second bias condition program, respectively.

Example 25, which can be combined with other examples herein, is a continuous analyte monitoring system for measuring a concentration of at least one analyte, the continuous analyte monitoring system comprising: a sensor comprising a working electrode extending along a central axis; a reference electrode; and a solid-state electrolyte layer at least partially covering at least one of the working electrode and the reference electrode.

In Example 26, which can be combined with other examples herein, the subject matter of Example 25 optionally includes a sensor control circuit, the sensor control circuit configured to perform operations comprising: applying a bias condition to the sensor; and accessing a signal generated by the sensor in vivo and biased to the bias condition, the signal indicating a concentration of an analyte.

In Example 27, which can be combined with other examples herein, the subject matter of any one or more of Examples 25-26 optionally includes wherein the analyte is oxygen.

In Example 28, which can be combined with other examples herein, the subject matter of any one or more of Examples 25-27 optionally includes wherein the reference electrode extends coaxially along the central axis.

In Example 29, which can be combined with other examples herein, the subject matter of any one or more of Examples 25-28 optionally includes wherein the working electrode, the reference electrode, or both are substantially planar.

In Example 30, which can be combined with other examples herein, the subject matter of any one or more of Examples 25-29 optionally includes a counter electrode in electrical communication with the working electrode, the reference electrode, or both.

In Example 31, which can be combined with other examples herein, the subject matter of any one or more of Examples 25-30 optionally includes an enzyme layer at least partially covering the working electrode, the reference electrode, or both.

In Example 32, which can be combined with other examples herein, the subject matter of any one or more of Examples 25-31 optionally includes wherein the solid-state electrolyte layer comprises a polyelectrolyte.

In Example 33, which can be combined with other examples herein, the subject matter of any one or more of Examples 25-32 optionally includes wherein the working electrode comprises platinum and tantalum and the reference electrode comprises silver and silver chloride.

In Example 34, which can be combined with other examples herein, the subject matter of any one or more of Examples 25-33 optionally includes wherein the solid-state electrolyte layer is disposed between and in electrical communication with the working electrode and reference electrode.

In Example 35, which can be combined with other examples herein, the subject matter of any one or more of Examples 25-34 optionally includes wherein at least a portion of the working electrode and a portion of the reference electrode are exposed to the analyte.

In Example 36, which can be combined with other examples herein, the subject matter of any one or more of Examples 25-35 optionally includes wherein buckling strength of the sensor is in a range of 0.010 lbf to 0.10 lbf.

In Example 37, which can be combined with other examples herein, the subject matter of any one or more of Examples 25-36 optionally includes a transmitter capable of transmitting data obtained during the bias condition to a display device.

In Example 38, which can be combined with other examples herein, the subject matter of any one or more of Examples 25-37 optionally includes wherein the reference electrode and the working electrode are separated by a membrane.

In Example 39, which can be combined with other examples herein, the subject matter of Example 38 optionally includes wherein the membrane comprises a polymer.

Example 40, which can be combined with other examples herein, is a method of using a continuous analyte monitoring system, the method comprising: biasing an in vivo sensor, by a sensor control circuit, to a bias condition, the sensor comprising: a working electrode extending along a central axis; and a reference electrode; a solid-state electrolyte layer partially covering at least one of the working electrode and the reference electrode; and accessing by the sensor control circuit a signal generated by the sensor in vivo while the first bias condition is applied, the signal indicating a concentration of an analyte; and accessing, by the sensor control circuit, a signal generated by the sensor in vivo while the second bias condition is applied to the sensor, the signal indicating a concentration of an analyte.

In Example 41, which can be combined with other examples herein, the subject matter of Example 40 optionally includes wherein the analyte is oxygen.

In Example 42, which can be combined with other examples herein, the subject matter of Example 41 optionally includes wherein the oxygen is interstitial oxygen.

In Example 43, which can be combined with other examples herein, the subject matter of any one or more of Examples 40-42 optionally includes wherein the reference electrode extends coaxially along the central axis.

In Example 44, which can be combined with other examples herein, the subject matter of any one or more of Examples 40-43 optionally includes wherein the reference electrode is configured to reside ex vivo.

In Example 45, which can be combined with other examples herein, the subject matter of any one or more of Examples 40-44 optionally includes wherein the working electrode, the reference electrode, or both are substantially planar.

In Example 46, which can be combined with other examples herein, the subject matter of any one or more of Examples 40-45 optionally includes a counter electrode in electrical communication with the working electrode, the reference electrode, or both.

In Example 47, which can be combined with other examples herein, the subject matter of any one or more of Examples 40-46 optionally includes an enzyme layer at least partially covering the working electrode, the reference electrode, or both.

In Example 48, which can be combined with other examples herein, the subject matter of any one or more of Examples 40-47 optionally includes wherein the solid-state electrolyte layer comprises a polyelectrolyte.

In Example 49, which can be combined with other examples herein, the subject matter of any one or more of Examples 40-48 optionally includes wherein the working electrode comprises platinum and tantalum and the reference electrode comprises silver and silver chloride.

In Example 50, which can be combined with other examples herein, the subject matter of any one or more of Examples 40-49 optionally includes wherein the solid-state electrolyte layer is disposed between and in electrical communication with the working electrode and reference electrode.

In Example 51, which can be combined with other examples herein, the subject matter of any one or more of Examples 40-50 optionally includes wherein at least a portion of the working electrode and a portion of the reference electrode are exposed to the analyte.

In Example 52, which can be combined with other examples herein, the subject matter of any one or more of Examples 40-51 optionally includes wherein buckling strength of the sensor is in a range of 0.010 lbf to 0.10 lbf.

In Example 53, which can be combined with other examples herein, the subject matter of any one or more of Examples 40-52 optionally includes a transmitter capable of transmitting data obtained during the bias condition to a display device.

Example 54, which can be combined with other examples herein, is a method of calibrating an analyte sensor, the method comprising: exposing the analyte sensor to a first known analyte concentration, the analyte sensor comprising: a working electrode extending along a central axis; and a reference electrode; a solid-state electrolyte layer at least partially covering at least one of the working electrode and the reference electrode; accessing a first sensor signal generated by the analyte sensor while the analyte sensor is exposed to the first known analyte concentration; exposing the analyte sensor to a second known analyte concentration; accessing a second sensor signal generated by the analyte sensor while the analyte sensor is exposed to the second known analyte concentration; and determining a calibration parameter using the first signal and the second signal.

In Example 55, which can be combined with other examples herein, the subject matter of Example 54 optionally includes wherein the calibration parameter describes a linear relationship between an amount of signal produced by the analyte sensor and analyte concentration.

In Example 56, which can be combined with other examples herein, the subject matter of any one or more of Examples 54-55 optionally includes the calibration parameter comprises a sensitivity, the sensitivity describing an analyte concentration per unit of sensor signal.

In Example 57, which can be combined with other examples herein, the subject matter of any one or more of Examples 54-56 optionally includes accessing a third sensor signal generated by the analyte sensor in vivo; and determining a concentration of the analyte in vivo using the third sensor signal and the calibration parameter.

In Example 58, which can be combined with other examples herein, the subject matter of any one or more of Examples 54-57 optionally includes wherein the analyte of the known analyte concentration is oxygen.

In Example 59, which can be combined with other examples herein, the subject matter of any one or more of Examples 54-58 optionally includes wherein the working electrode, the reference electrode, or both are substantially planar.

In Example 60, which can be combined with other examples herein, the subject matter of any one or more of Examples 54-59 optionally includes wherein the solid-state electrolyte layer comprises a polyelectrolyte.

In Example 61, which can be combined with other examples herein, the subject matter of any one or more of Examples 54-60 optionally includes wherein the working electrode comprises platinum and tantalum and the reference electrode comprises silver and silver chloride.

In Example 62, which can be combined with other examples herein, the subject matter of any one or more of Examples 54-61 optionally includes wherein the solid-state electrolyte layer is disposed between and in electrical communication with the working electrode and reference electrode.

In Example 63, which can be combined with other examples herein, the subject matter of any one or more of Examples 54-62 optionally includes wherein at least a portion of the working electrode and a portion of the reference electrode are exposed to the analyte.

Example 64 is continuous analyte monitoring system for measuring a concentration of a first analyte and concentration of a second analyte in a host, the continuous analyte monitoring system comprising: a sensor comprising a working electrode extending along a central axis; and a reference electrode; and a sensor control circuit, the sensor control circuit configured to perform operations comprising: applying a first bias condition between the working electrode and the reference electrode, the first bias condition having a first polarity and a first magnitude; accessing a first signal generated by the sensor in vivo while the first bias condition is applied to the sensor, the first signal indicating a concentration of a first analyte at the host; applying a second bias condition between the working electrode and the reference electrode, the second bias condition having a second polarity and a second magnitude, the second polarity being opposite the first polarity; and accessing, by the sensor control circuit, a second signal generated by the sensor in vivo while the second bias condition is applied to the sensor, the second signal indicating a concentration of a second analyte at the host, the second analyte being different than the first analyte; and applying a third bias condition between the working electrode and the reference electrode, the third bias condition having a third polarity and a third magnitude, the third polarity being equivalent to the first polarity and the third magnitude being greater than the first magnitude.

Example 65, which can be combined with other examples herein, the subject matter of Example 64, optionally includes wherein the first analyte is glucose or lactate and the second analyte is oxygen.

Example 66, which can be combined with other examples herein, the subject matter of any one or more of Examples 64-65, optionally includes wherein the reference electrode is configured to support a redox reaction the working electrode is configured to support an oxidation reaction.

Example 67, which can be combined with other examples herein, the subject matter of any one or more of Examples 46-66, optionally includes wherein the reference electrode extends coaxially along the central axis.

Example 68, which can be combined with other examples herein, the subject matter of any one or more of Examples 64-67, optionally includes wherein the reference electrode is configured to operate in an ex vivo position.

Example 69, which can be combined with other examples herein, the subject matter of any one or more of Examples 64-68, optionally includes wherein the working electrode, the reference electrode, or both are substantially planar.

Example 70, which can be combined with other examples herein, the subject matter of any one or more of Examples 64-69, optionally includes further comprising a counter electrode in electrical communication with the working electrode, the reference electrode, or both.

Example 71, which can be combined with other examples herein, the subject matter of any one or more of Examples 64-70, optionally includes further comprising an enzyme layer at least partially covering the working electrode.

Example 72, which can be combined with other examples herein, the subject matter of Example 71, optionally includes wherein the enzyme layer comprises an oxidase, dehydrogenase, or a mixture thereof.

Example 73, which can be combined with other examples herein, the subject matter of any one or more of Examples 71-72, optionally includes further comprising a resistance layer at least partially covering the enzyme layer.

Example 74, which can be combined with other examples herein, the subject matter of any one or more of Examples 64-73, optionally includes wherein the working electrode comprises platinum, palladium, rhodium, iridium, tantalum, or a mixture thereof and the reference electrode comprises silver and silver chloride.

Example 75, which can be combined with other examples herein, the subject matter of any one or more of Examples 64-74, optionally includes wherein at least a portion of the working electrode and the reference electrode are configured to be exposed to at least one of glucose, lactate, and oxygen.

Example 76, which can be combined with other examples herein, the subject matter of any one or more of Examples 64-75, optionally includes wherein a buckling strength of the sensor is in a range of 0.010 lbf to 0.10 lbf.

Example 77, which can be combined with other examples herein, the subject matter of any one or more of Examples 64-76, optionally includes the first polarity being positive from the working electrode to the reference electrode and the second polarity being negative from the working electrode to the reference electrode.

Example 78, which can be combined with other examples herein, the subject matter of any one or more of Examples 64-77, optionally includes the first magnitude being between about 0.5 V and about 0.7 V.

Example 79, which can be combined with other examples herein, the subject matter of any one or more of Examples 64-78, optionally includes the second magnitude being between about −0.3V and about −0.2V.

Example 80, which can be combined with other examples herein, the subject matter of any one or more of Examples 64-79, optionally includes the third magnitude being between about 0.7V and to about 1.2V.

Example 81, which can be combined with other examples herein, the subject matter of Examples 64-80, optionally includes further comprising a transmitter capable of transmitting data obtained during the first bias condition, the second bias condition, the third bias condition, or a combination thereof to a device.

Example 82, which can be combined with other examples herein, the subject matter of any one or more of Examples 64-81, optionally includes wherein the third bias condition is applied for an amount of time that is less than a time that each of the first bias condition and the second bias condition are applied.

Example 83, which can be combined with other examples herein, the subject matter of any one or more of Examples 64-82, optionally includes wherein the first bias condition is applied for a time in a range of from about 4 minutes to about 80 minutes; the second bias condition is applied for a time in range of from about 10 seconds to about 10 minutes; and the third bias condition is applied for a time in a range of from about 5 seconds to about 60 seconds.

Example 84, which can be combined with other examples herein, the subject matter of any one or more of Examples 64-83, optionally includes wherein the first bias condition is applied for a time in a range of from about 4 minutes to about 30 minutes; the second bias condition is applied for a time in range of from about 10 seconds to about 2 minutes; and the third bias condition is applied for a time in a range of from about 10 seconds to about 60 seconds.

Example 85, which can be combined with other examples herein, the subject matter of any one or more of Examples 64-84, optionally includes wherein the second bias condition is applied for a time in range of from about 1 minute to about 10 minutes; and the third bias condition is applied for a time in a range of from about 10 seconds to about 60 seconds.

Example 86, which can be combined with other examples herein, the subject matter of any one or more of Examples 64-85, optionally includes wherein the second bias condition is applied for a time in range of from about 1 minute to about 4 minutes; and the third bias condition is applied for a time in a range of from about 10 seconds to about 60 seconds.

Example 87, which can be combined with other examples herein, the subject matter of any one or more of Examples 64-86, optionally includes wherein the second bias condition is applied for a time ranging from about 3 times to about 9 times greater than the third bias condition.

Example 88, which can be combined with other examples herein, the subject matter of any one or more of Examples 64-87, optionally includes wherein the second bias condition is applied for a time ranging from about 5 times to about 7 times greater than the third bias condition.

Example 89, which can be combined with other examples herein, the subject matter of any one or more of Examples 64-88, optionally includes further comprising a solid-state electrolyte layer at least partially covering at least one of the working electrode and the reference electrode.

Example 90, which can be combined with other examples herein, the subject matter of any one or more of Example 89, optionally includes wherein the solid-state electrolyte layer comprises a polyelectrolyte.

Example 91, which can be combined with other examples herein, the subject matter of Examples 89-90, optionally includes wherein the solid-state electrolyte layer is disposed between and in electrical communication with the working electrode and reference electrode.

Example 92, which can be combined with other examples herein, the subject matter of any one or more of Examples 89-91, optionally includes wherein the reference electrode and the working electrode are separated by a membrane.

Example 93, which can be combined with other examples herein, the subject matter of Example 92, optionally includes wherein the membrane comprises a polymer.

Example 94 is a continuous analyte monitoring, the method comprising: applying a first bias condition between a working electrode extending coaxially along a central axis and a reference electrode of an in vivo sensor, the first bias condition having a first polarity and a first magnitude accessing, by a sensor control circuit a first signal generated by the sensor in vivo while the first bias condition is applied to the sensor, the first signal indicating a concentration of a first analyte at a host; applying a second bias condition between the working electrode and the reference electrode, the second bias condition having a second polarity and a second magnitude, the second polarity being opposite the first polarity; and accessing, by the sensor control circuit, a second signal generated by the sensor in vivo while the second bias condition is applied to the sensor, the second signal indicating a concentration of a second analyte at the host, the second analyte being different than the first analyte; and applying a third bias condition between the working electrode and the reference electrode, the third bias condition having a third polarity and a third magnitude, the third polarity being equivalent to the first polarity and the third magnitude being greater than the first magnitude.

Example 95 which can be combined with other examples herein, the subject matter of Example 94, optionally includes wherein the first bias condition and the third bias condition have a first polarity and the second bias condition has a second polarity that is the opposite of the first polarity.

Example 96, which can be combined with other examples herein, the subject matter of any one or more of Examples 94-95 optionally includes wherein the biasing of the sensor to the first bias condition and the third bias condition comprises applying a positive potential difference between the working electrode and the reference electrode.

Example 97, which can be combined with other examples herein, the subject matter of Example 96, optionally includes wherein the positive potential difference of the first bias condition is in a range of from about 0.5 V to 0.7 V, relative to the reference electrode.

Example 98, which can be combined with other examples herein, the subject matter of any one or more of Examples 96 97, optionally includes wherein the positive potential difference of the third bias condition is in a range of from about 0.7 V to about 1.2 V, relative to the reference electrode.

Example 99, which can be combined with other examples herein, the subject matter of Examples 94-98, optionally includes wherein the biasing of the sensor to the second bias condition comprises applying a negative potential difference between the working electrode and the reference electrode.

Example 100, which can be combined with other examples herein, the subject matter of Example 99, optionally includes wherein the negative potential difference is in a range of from about −0.3 to −0.2V, relative to the reference electrode.

Example 101, which can be combined with other examples herein, the subject matter of any one or more of Examples 94-100, optionally includes wherein the first bias condition is applied for a time in a range of from about 4 minutes to about 80 minutes; the second bias condition is applied for a time in range of from about 10 seconds to about 10 minutes; and the third bias condition is applied for a time in a range of from about 5 seconds to about 60 seconds.

Example 102, which can be combined with other examples herein, the subject matter of any one or more of Examples 94-101, optionally includes wherein the first bias condition is applied for a time in a range of from about 4 minutes to about 30 minutes; the second bias condition is applied for a time in range of from about 10 seconds to about 2 minutes; and the third bias condition is applied for a time in a range of from about 10 seconds to about 60 seconds.

Example 103, which can be combined with other examples herein, the subject matter of any one or more of Examples 94-102, optionally includes wherein the second bias condition is applied for a time in range of from about 1 minute to about 10 minutes; and the third bias condition is applied for a time in a range of from about 10 seconds to about 60 seconds.

Example 104, which can be combined with other examples herein, the subject matter of any one or more of Examples 94-103, optionally includes wherein the second bias condition is applied for a time in range of from about 1 minute to about 4 minutes; and the third bias condition is applied for a time in a range of from about 10 seconds to about 60 seconds.

Example 105, which can be combined with other examples herein, the subject matter of any one or more of Examples 94-104, optionally includes wherein the second bias condition is applied for a time ranging from about 3 times to about 9 times greater than the third bias condition.

Example 106, which can be combined with other examples herein, the subject matter of any one or more of Examples 94-105, optionally includes wherein the second bias condition is applied for a time ranging from about 5 times to about 7 times greater than the third bias condition.

Example 107, which can be combined with other examples herein, the subject matter of any one or more of Examples 94-106, optionally includes wherein the sensor is configured to reside in vivo.

Example 108, which can be combined with other examples herein, the subject matter of any one or more of Examples 94-107, optionally includes further comprising switching the sensor between first bias condition, the second bias condition, and the third bias condition.

Example 109, which can be combined with other examples herein, the subject matter of any one or more of Example 108, optionally includes wherein switching between the first bias condition, the second bias condition, and the third bias condition comprises executing a first bias condition program, a second bias condition program, and a third bias condition respectively.

Example 110, which can be combined with other examples herein, the subject matter of any one or more of Examples 108-109, optionally includes further comprising executing a fourth bias condition program following executing the third bias condition.

Example 111, which can be combined with other examples herein, the subject matter of Example 110, optionally includes wherein the fourth bias condition comprises a positive potential difference that is substantially equivalent to the positive potential difference of the first bias condition.

Example 112, optionally includes which can be combined with other examples herein, the subject matter of any one or more of Examples 94-111, wherein the sensor further comprises a solid-state electrolyte layer at least partially covering at least one of the working electrode and the reference electrode.

Example 113, optionally includes which can be combined with other examples herein, the subject matter of Example 112, wherein the solid-state electrolyte layer comprises a polyelectrolyte.

Example 114, optionally includes which can be combined with other examples herein, the subject matter of any one or more of Examples 112-113, wherein the solid-state electrolyte layer is disposed between and in electrical communication with the working electrode and reference electrode.

Example 115, which can be combined with other examples herein, the subject matter of any one or more of Examples 110-114, optionally includes wherein the reference electrode and the working electrode are separated by a membrane.

Example 116, which can be combined with other examples herein, the subject matter of Example 115, optionally includes wherein the membrane comprises a polymer.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various aspects described in the present document.

FIGS. 18A-8B illustrates an example of transient raw current values corresponding to glucose concentrations at multiple times after the completion of measuring an oxygen concentration.

DETAILED DESCRIPTION

Figure 1:
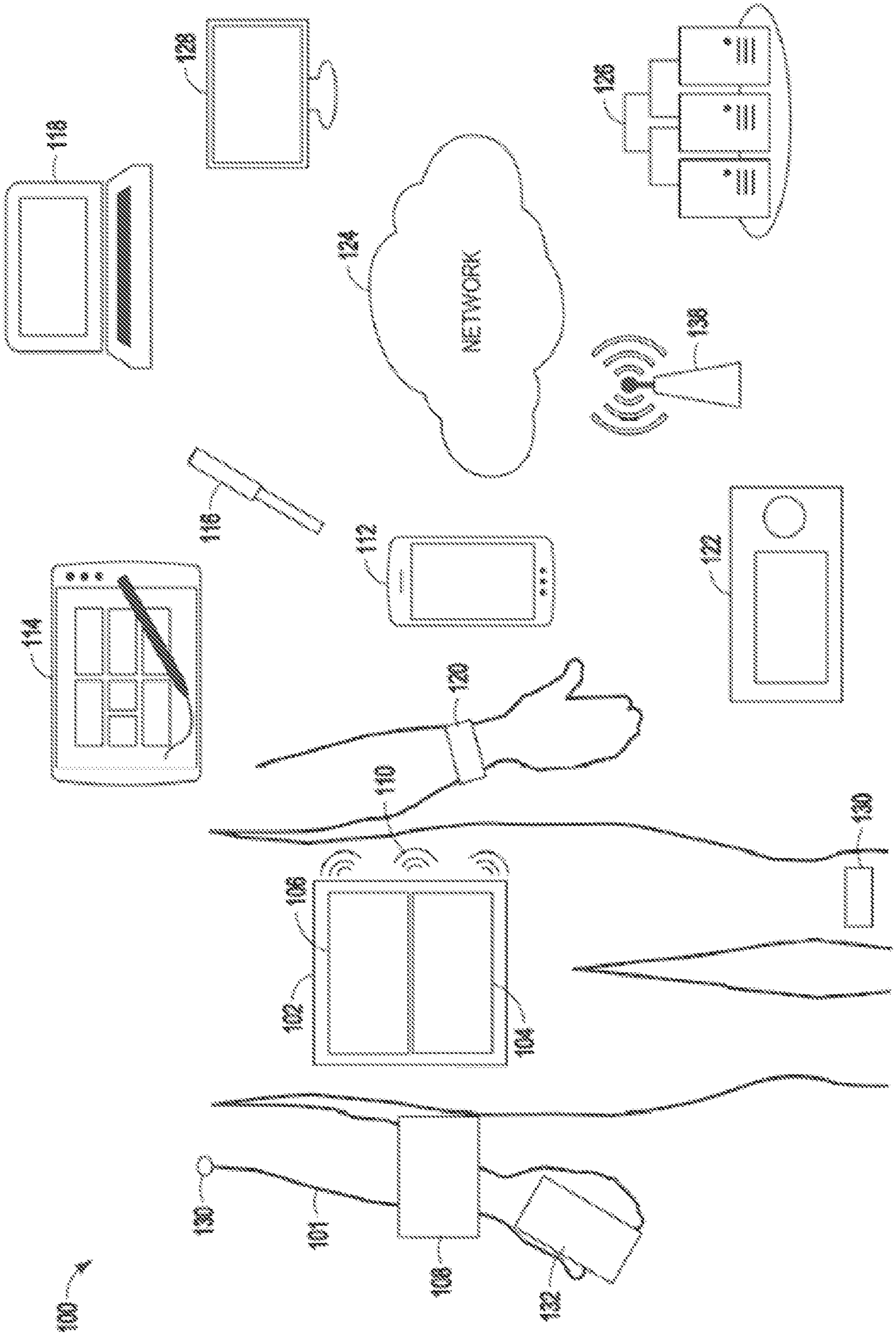
FIG. 1 illustrates an example of an environment including a continuous analyte monitoring system according to various aspects of the present disclosure.

Various examples described herein are directed to continuous analyte monitoring systems and methods of use for continuous analyte monitoring systems. A continuous analyte monitoring system is placed in contact with bodily fluid of a host to measure a concentration of an analyte, such as glucose, in the bodily fluid. In some examples, the continuous analyte monitoring system is inserted under the skin (e.g., in vivo) of the host and placed in contact with interstitial fluid below the skin to measure the concentration of the analyte in the interstitial fluid.

The terms and phrases "analyte measuring device," "biosensor," "sensor," "sensing region," and "sensing mechanism" as used herein are broad terms and phrases, and are to be given their ordinary and customary meaning to a person of ordinary skill in the art (and are not to be limited to a special or customized meaning), and refer without limitation to the area of an analyte-monitoring device responsible for the detection of, or transduction of a signal associated with, a particular analyte or combination of analytes. In one example, such devices are capable of providing specific quantitative, semi-quantitative, qualitative, semi qualitative analytical information using a biological recognition element combined with a transducing (detecting) element.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 weight percentage (wt %) to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The terms "adhere" and "attach" as used herein are broad terms, and are to be given their ordinary and customary meaning to a person of ordinary skill in the art (and are not be limited to a special or customized meaning), and refer without limitation to hold, bind, or stick, for example, by gluing, bonding, grasping, interpenetrating, or fusing.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some examples, the analyte for measurement by the sensing regions, devices, and methods is glucose. However, other analytes are contemplated as well, including but not limited to a carboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; blood electrolytes (including but not limited to sodium and potassium) c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatinine, creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax,* 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycerol, glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; beta-hydroxybutyrate; ketone, lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalis, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Treponema pallidum, Trypanosoma cruzi/rangeli*, vesicular stomatitis virus, *Wuchereria bancrofti*, yellow fever virus); specific antigens (hepatitis B virus, HIV-1); succinyl acetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain examples. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and histamine.

The term "bioactive agent" as used herein is a broad term, and is to be given its ordinary and customary meaning to a person of ordinary skill in the art (and is not to be limited to a special or customized meaning), and refers without limitation to any substance that has an effect on or elicits a response from living tissue.

The phrases "biointerface membrane" and "biointerface layer" and "biointerface/drug releasing membrane" and "biointerface/drug releasing layer" as used interchangeably herein is a broad phrase, and is to be given its ordinary and customary meaning to a person of ordinary skill in the art (and is not to be limited to a special or customized meaning), and refers without limitation to a permeable membrane or layer that functions as an interface between host tissue and an implantable device.

The phrase "barrier cell layer" as used herein is a broad term, and is to be given its ordinary and customary meaning to a person of ordinary skill in the art (and is not to be limited to a special or customized meaning), and refers without limitation to a part of a foreign body response that forms a cohesive monolayer of cells (for example, macrophages and foreign body giant cells) that substantially block the transport of molecules and other substances to the implantable device.

The term "biostable" as used herein is a broad term, and is to be given its ordinary and customary meaning to a person of ordinary skill in the art (and is not to be limited to a special or customized meaning), and refers without limitation to materials that are relatively resistant to degradation by processes that are encountered in vivo.

The terms "bioresorbable" or "bioabsorbable" as used herein are broad terms, and are to be given their ordinary and customary meaning to a person of ordinary skill in the art (and are not to be limited to a special or customized meaning), and refer without limitation to materials that can be absorbed, or lose substance, in a biological system.

The phrase "cell processes" as used herein is a broad term, and is to be given its ordinary and customary meaning to a person of ordinary skill in the art (and is not to be limited to a special or customized meaning), and refers without limitation to pseudopodia of a cell.

The phrase "cellular attachment" as used herein is a broad term, and is to be given its ordinary and customary meaning to a person of ordinary skill in the art (and is not to be limited to a special or customized meaning), and refers without limitation to adhesion of cells and/or cell processes to a material at the molecular level, and/or attachment of cells and/or cell processes to microporous material surfaces or macroporous material surfaces. One example of a material used in the prior art that encourages cellular attachment to its porous surfaces is the BIOPORE™ cell culture support marketed by Millipore (Bedford, Mass.), and as described in Brauker et al., U.S. Pat. No. 5,741,330. The term "coaxial" as used herein is to be construed broadly to include sensor architectures having elements aligned along a shared axis around a core that can be configured to have a circular, elliptical, triangular, polygonal, or other cross-section such elements can include electrodes, insulating layers, or other elements that can be positioned circumferentially around the core layer, such as a core electrode or core polymer wire.

The term "co-continuous" as used herein is a broad term, and is to be given its ordinary and customary meaning to a person of ordinary skill in the art (and is not to be limited to a special or customized meaning), and refers without limitation to a solid portion or cavity wherein an unbroken curved line in three dimensions can be drawn between two sides of a membrane.

The phrase "continuous analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and/or intermittently (but regularly) performed, for example, from about every 5 seconds or less to about 10 minutes or more, preferably from about 10, 15, 20, 25, 30, 35, 40, 45, 50, 55, or 60 second to about 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50 or 9.75 minutes. Further examples of continuous analyte sensors can be found in, for example, U.S. Pat. No. 8,828,201, Simpson, et al.; U.S. Pat. No. 9,131,885 Simpson, et al.; U.S. Pat. No. 9,237,864, Simpson, et al.; and U.S. Pat. No. 9,763,608, Simpson, et al., each of which is incorporated by reference in its entirety herein The term "coupled" as used herein may refer to two or more system elements or components that are configured to be at least one of electrically, mechanically, thermally, or otherwise attached.

The term "removably coupled" as used herein may refer to two or more system elements or components that are configured to be or have been electrically, mechanically, thermally, or otherwise attached and detached without damaging any of the coupled elements or components. The term "permanently coupled" as used herein may refer to two or more system elements or components that are configured to be or have been electrically, mechanically, thermally, operably, chemically, or otherwise attached but cannot be uncoupled without damaging at least one of the coupled elements or components.

The phrase "defined edges" as used herein is a broad phrase, and is to be given its ordinary and customary meaning to a person of ordinary skill in the art (and is not to be limited to a special or customized meaning), and refers without limitation to abrupt, distinct edges or borders among layers, domains, coatings, or portions. "Defined edges" are in contrast to a gradual transition between layers, domains, coatings, or portions.

The term "discontinuous" as used herein is a broad term, and is to be given its ordinary and customary meaning to a person of ordinary skill in the art (and is not to be limited to a special or customized meaning), and refers without limitation to disconnected, interrupted, or separated portions, layers, coatings, or domains.

The term "distal" as used herein is a broad term, and is to be given its ordinary and customary meaning to a person of ordinary skill in the art (and is not to be limited to a special or customized meaning), and refers without limitation to a region spaced relatively far from a point of reference, such as an origin or a point of attachment.

The term "domain" as used herein is a broad term, and is to be given its ordinary and customary meaning to a person of ordinary skill in the art (and is not to be limited to a special or customized meaning), and refers without limitation to a region of the membrane system that can be a layer, multiple layers, a uniform or non-uniform gradient (for example, an anisotropic region of a membrane), or a portion of a membrane configured to perform one or more functions. The domains discussed herein can be formed as a single layer, as two or more layers, as pairs of bi-layers, or as combinations thereof The term "drift" as used herein is a broad term, and is to be given its ordinary and customary meaning to a person of ordinary skill in the art (and is not to be limited to a special or customized meaning), and refers without limitation to a progressive increase or decrease in signal over time that is unrelated to changes in host systemic analyte concentrations. For example, such as host postprandial glucose concentrations. While not wishing to be bound by theory, it is believed that drift may be the result of a local decrease in glucose transport to the sensor, due to cellular invasion, which surrounds the sensor, for example. It is also believed that an insufficient amount of interstitial fluid is surrounding the sensor, which results in reduced oxygen and/or glucose transport to the sensor, for example. An increase in local interstitial fluid may slow or reduce drift and thus improve sensor performance. Drift may also be the result of sensor electronics, or algorithmic models used to compensate for noise or other anomalies that can occur with electrical signals in the picoamp range.

The phrases "drug releasing membrane" and "drug releasing layer" as used interchangeably herein are each a broad phrase, and each are to be given its ordinary and customary meaning to a person of ordinary skill in the art (and is not to be limited to a special or customized meaning), and refers without limitation to a permeable or semi-permeable membrane which is permeable to one or more bioactive agents. In one example, the "drug releasing membrane" and "drug releasing layer" can be comprised of two or more domains and may be a few microns thickness or more. In one example the drug releasing layer and/or drug releasing membrane are substantially the same as the biointerface layer and/or biointerface membrane. Examples of drug releasing layers and membranes may be found in pending U.S. Patent Publication Number: 2022-0296867, titled "DRUG RELEASING MEMBRANE FOR ANALYTE SENSOR," filed Mar. 17, 2022, incorporated by reference in its entirety herein; as well as in pending U.S. application Ser. No. 17/945,585, titled "DRUG RELEASING MEMBRANE FOR ANALYTE SENSOR," filed Mar. 17, 2022, incorporated by reference in its entirety herein.

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. In a working electrode, hydrogen peroxide produced by an enzyme-catalyzed reaction of an analyte being detected reacts can create a measurable electronic current. For example, in the detection of glucose, glucose oxidase produces hydrogen peroxide (H2O2) as a byproduct. The H2O2 reacts with the surface of the working electrode to produce two protons (2H+), two electrons (2e−) and one molecule of oxygen (O2), which produces the electronic current being detected. In a counter electrode, a reducible species, for example, O2 is reduced at the electrode surface so as to balance the current generated by the working electrode.

The term "host" as used herein is a broad term, and is to be given its ordinary and customary meaning to a person of ordinary skill in the art (and is not to be limited to a special or customized meaning), and refers without limitation to mammals, preferably humans.

The terms "interferants" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured.

The term "in vivo" without limitation refers to the portion of a device (for example, a sensor) adapted for insertion into and/or existence within a living body of a host.

The term "ex vivo" refers to a portion of a device (for example, a sensor) adapted to remain and/or exist outside of a living body of a host.

The phrase "membrane system" as used herein is a broad phrase, and is to be given its ordinary and customary meaning to a person of ordinary skill in the art (and is not to be limited to a special or customized meaning), and refers without limitation to a permeable or semi-permeable membrane that can be comprised of two or more domains and may be formed from one or more materials to a thickness of a few microns or more, which is permeable to one or more analytes. In one example, the membrane is permeable to oxygen and is optionally permeable to, e.g., glucose or one or more other analytes. In one example, the membrane system comprises an immobilized glucose oxidase enzyme, which enables a reaction to occur between glucose and oxygen whereby a concentration of glucose can be measured.

The term "noise," as used herein, is a broad term and is used in its ordinary sense, including, without limitation, a signal detected by the sensor or sensor electronics that is unrelated to analyte concentration and can result in reduced sensor performance. One type of noise has been observed during the few hours (e.g., about 2 to about 24 hours) after sensor insertion. After the first 24 hours, the noise may disappear or diminish, but in some hosts, the noise may last for about three to four days. In some cases, noise can be reduced using predictive modeling, artificial intelligence, and/or algorithmic means. In other cases, noise can be reduced by addressing immune response factors associated with the presence of the implanted sensor, such as using a drug releasing layer with at least one bioactive agent. For example, noise of one or more exemplary biosensors as presently disclosed can be determined and then compared qualitatively or quantitatively. By way of example, obtaining a raw signal timeseries with a fixed sampling interval (in units of pA), a smoothed version of the raw signal timeseries can be obtained, e.g., by applying a 3rd order lowpass digital Chebyshev Type II filter. Other smoothing algorithms can be used. At each sampling interval, an absolute difference, in units of pA, can be calculated to provide a smoothed timeseries. This smoothed timeseries can be converted into units of mg/dL, (the unit of "noise"), using a glucose sensitivity timeseries, in units of pA/mg/dL, where the glucose sensitivity timeseries is derived by optimizing a mathematical model between the raw signal and reference blood glucose measurements (e.g., obtained from Blood Glucose Meter). Optionally, the time series can be aggregated as desired, e.g., by hour or day. Comparison of corresponding time series between different exemplary biosensors with the presently disclosed drug releasing layer and one or more bioactive agents provides for qualitative or quantitative determination of improvement of noise.

The terms "nonbioresorbable" or "nonbioabsorbable" as used herein are broad terms, and are to be given their ordinary and customary meaning to a person of ordinary skill in the art (and are not to be limited to a special or customized meaning), and refer without limitation to materials that are not substantially absorbed, or do not substantially lose substance, in a biological system.

The terms "non-zwitterionic dipole" and "non-zwitterionic dipolar compound" as used herein are broad terms, and are to be given their ordinary and customary meaning to a person of ordinary skill in the art (and is not to be limited to a special or customized meaning), and refer without limitation to compounds in which a neutral molecule of the compound have a positive and negative electrical charge at different locations within the molecule. The positive and negative electrical charges within the molecule can be any non-zero, but less than full unit, charges.

The terms "operably connected" and "operably linked" as used herein are broad terms, and are to be given their ordinary and customary meaning to a person of ordinary skill in the art (and are not to be limited to a special or customized meaning), and refer without limitation to one or more components linked to another component(s) in a manner that facilitates transmission of signals between the components. For example, one or more electrodes can be used to detect an analyte in a sample and convert that information into a signal; the signal can then be transmitted to an electronic circuit. In this example, the electrode is "operably linked" to the electronic circuit.

The term "optional" or "optionally" means that the subsequently described event or circumstance can or cannot occur, and that the description includes instances where the event or circumstance occurs and instances where it does not occur. The term "planar" as used herein is to be interpreted broadly to describe sensor architecture having a substrate including a first side and a second side, and a plurality of elements arranged on one or more sides of the substrate, the elements may or may not be electrically or otherwise coupled, where the elements can include conductive or insulating layers or elements configured to operate as a circuit.

The term "polyampholytic polymer" as used herein is a broad term, and is to be given its ordinary and customary meaning to a person of ordinary skill in the art (and is not to be limited to a special or customized meaning), and refers without limitation to polymers comprising both cationic and anionic groups. Such polymers can be prepared to have about equal numbers of positive and negative charges, and thus the surface of such polymers can be about net neutrally charged. Alternatively, such polymers can be prepared to have an excess of either positive or negative charges, and thus the surface of such polymers can be net positively or negatively charged, respectively.

The term "polymerization group" used herein is a broad term, and is to be given its ordinary and customary meaning to a person of ordinary skill in the art (and is not to be limited to a special or customized meaning), and refers without limitation to a functional group that permits polymerization of the monomer with itself to form a homopolymer or together with different monomers to form a copolymer. Depending on the type of polymerization methods employed, the polymerization group can be selected from alkene, alkyne, epoxide, lactone, amine, hydroxyl, isocyanate, carboxylic acid, anhydride, silane, halide, aldehyde, and carbodiimide.

The term "polyzwitterions" as used herein is a broad term, and is to be given its ordinary and customary meaning to a person of ordinary skill in the art (and is not to be limited to a special or customized meaning), and refers without limitation to polymers where a repeating unit of the polymer chain is a zwitterionic moiety. Polyzwitterions are also known as polybetaines. Since polyzwitterions have both cationic and anionic groups, they are a type of polyampholytic polymer. They are unique, however, because the cationic and anionic groups are both part of the same repeating unit, which means a polyzwitterion has the same number of cationic groups and anionic groups whereas other polyampholytic polymers can have more of one ionic group than the other. Also, polyzwitterions have the cationic group and anionic group as part of a repeating unit. Polyampholytic polymers need not have cationic groups connected to anionic groups, they can be on different repeating units and thus may be distributed apart from one another at random intervals, or one ionic group may outnumber the other.

The term "proximal" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some examples of a device include a membrane system having a biointerface layer and an enzyme layer. If the sensor is deemed to be the point of reference and the enzyme layer is positioned nearer to the sensor than the biointerface layer, then the enzyme layer is more proximal to the sensor than the biointerface layer.

The phrases and terms "processor module" and "microprocessor" as used herein are broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer. The use of the processor module or microprocessor can improve the function of an analyte sensor, battery, measurement circuit, processor, memory, or a combination thereof.

The term "sensing membrane" as used herein is a broad term, and is to be given its ordinary and customary meaning to a person of ordinary skill in the art (and is not to be limited to a special or customized meaning), and refers without limitation to a permeable or semi-permeable membrane that can comprise one or more domains in a membrane system and that is constructed of materials having a thickness of a few microns or more, and that are permeable to reactants and/or co-reactants employed in determining the analyte of interest. As an example, a sensing membrane can comprise an immobilized glucose oxidase enzyme, which catalyzes an electrochemical reaction with glucose and oxygen to permit measurement of a concentration of glucose. In some further examples, a sensing membrane can include an oxidase, dehydrogenase, or a mixture thereof that can react with lactate.

The term "invasive" as used herein is a broad term, and is to be given its ordinary and is to be given its ordinary and customary meaning to a person of ordinary skill in the art (and is not to be limited to a special or customized meaning), and refers without limitation to a medical procedure that invades (enters) the body, usually by cutting or puncturing the skin or by inserting instruments into the body.

The term "minimally-invasive" as used herein is a broad term, and is to be given its ordinary and is to be given its ordinary and customary meaning to a person of ordinary skill in the art (and is not to be limited to a special or customized meaning), and refers without limitation to a procedure minimizing incisions to reduce trauma to the body. This type of procedure, for example, can be performed using thin-needles and an endoscope to visually guide the procedure.

The term "non-invasive sensing techniques" as used herein is a broad term, and is to be given its ordinary and is to be given its ordinary and customary meaning to a person of ordinary skill in the art (and is not to be limited to a special or customized meaning), and refers without limitation to techniques for sensing an internal condition or analyte(s) while minimizing incisions to reduce trauma to the body. Examples of such techniques can include optically excited fluorescence, microneedle incision, and/or transdermal monitoring of glucose). The term "polyelectrolyte" as used herein is a broad term, and is to be given its ordinary and is to be given its ordinary and customary meaning to a person of ordinary skill in the art (and is not to be limited to a special or customized meaning), and refers without limitation to polymers whose repeating units bear an electrolyte group. For example, polycations and polyanions are polyelectrolytes. Polyelectrolytes dissociate in aqueous solutions, making the polymers charged. Polyelectrolyte properties are thus similar to both electrolytes and polymers and are sometimes called polysalts.

The term "semi-continuous" as used herein is a broad term, and is to be given its ordinary and customary meaning to a person of ordinary skill in the art (and is not to be limited to a special or customized meaning), and refers without limitation to a portion, coating, domain, or layer that includes one or more continuous and noncontinuous portions, coatings, domains, or layers. For example, a coating disposed around a sensing region but not about the sensing region is "semi-continuous."

The term "sensing membrane" as used herein is a broad term, and is to be given its ordinary and customary meaning to a person of ordinary skill in the art (and is not to be limited to a special or customized meaning), and refers without limitation to a permeable or semi-permeable membrane that can comprise one or more domains and that is constructed of materials having a thickness of a few microns or more, and that are permeable to reactants and/or co-reactants employed in determining the analyte of interest. As an example, a sensing membrane can comprise an immobilized glucose oxidase enzyme, which catalyzes an electrochemical reaction with glucose and oxygen to permit measurement of a concentration of glucose.

The term "signal medium" or "transmission medium" as used herein is a broad term, and is to be given its ordinary and is to be given its ordinary and customary meaning to a person of ordinary skill in the art (and is not to be limited to a special or customized meaning), and refers without limitation to a form of modulated data signal, carrier wave, and so forth.

The term "modulated data signal" as used herein is a broad term, and is to be given its ordinary and is to be given its ordinary and customary meaning to a person of ordinary skill in the art (and is not to be limited to a special or customized meaning), and refers without limitation to a signal that has one or more of its characteristics set or changed in such a matter as to encode information in the signal.

The terms "machine-readable medium," "computer-readable medium" and "device-readable medium" mean the same thing and may be used interchangeably in this disclosure and as used herein are broad terms, and are to be given its ordinary and is to be given its ordinary and customary meaning to a person of ordinary skill in the art (and are not to be limited to a special or customized meaning), and refers without limitation to both machine-storage media and signal media. Thus, the terms include both storage devices/media and carrier waves/modulated data signals.

The term "electrical contact" as used herein is a broad term, and is to be given its ordinary and is to be given its ordinary and customary meaning to a person of ordinary skill in the art (and are not to be limited to a special or customized meaning), and refers without limitation to materials that are sufficient contact so as to allow an electromagnetic signal to propagate between the materials. In some examples, the electromagnetic signal may be a current. In other examples, the electromagnetic signal is an induced or other wireless signal.

When an analyte sensor of the continuous monitoring system is exposed to one or more analytes, an electrochemical reaction between the analyte sensor and at least one analyte causes the analyte sensor to generate a raw sensor signal indicating the analyte concentration. The raw sensor signal may be a current that flows between two or more electrodes of the analyte sensor. Analyte sensors may have different numbers of electrodes. For example, a three-electrode analyte sensor may include a working electrode, a counter electrode, and a reference electrode. In the presence of one or more analytes, the electrochemical reaction causes a current to flow between the electrodes, where the raw sensor signal is, or is based on, the current generated. The current may flow primarily between the working electrode and the counter electrode, with the reference electrode providing a stable reference potential. In a two-electrode configuration an example analyte sensor includes a working electrode and a reference electrode. The reference electrode conducts current, similar to the counter electrode in a three-electrode configuration, and provides a stable reference potential, like the reference electrode in a three-electrode configuration. Accordingly, the reference electrode in a two-electrode arrangement is sometimes referred to as a counter-reference electrode. Herein, the term reference electrode may refer to the reference electrode of a three-electrode configuration, the counter-reference electrode of a two-electrode configuration, or similar electrodes in other configurations.

In use, sensor electronics apply a bias condition between the working electrode and the reference (e.g., counter-reference) electrode. The applied bias promotes the electrochemical reaction between the analyte and the analyte sensor, resulting in a current between the working electrode and the reference (e.g., counter-reference) electrode. In one example, the current comprises all of the raw sensor signal. In another example, the raw sensor signal includes the current in addition to one or more other elements.

Continuously measuring multiple analytes can be beneficial in a variety of contexts. For example, it may be cumbersome to wear multiple sensors, or existing sensors may not be configured to detect, in either a simultaneous or alternating fashion, two or more analytes. Additionally, measuring concentrations of different analytes can involve two or more different electrochemical reactions, which under some circumstances can make it difficult to use a single sensor. In some examples, a concentration of a first analyte and a second analyte may be known, and this data used in concert to predict adverse health events, deliver medication, or other actions. However, in other examples, the concentration of one analyte may be known while a concentrate of a second analyte is unknown. Being able to measure the concentrations of multiple analytes using the same sensor to perform continuous analyte monitoring addresses said concerns. In one example, the multi-analyte monitoring systems discussed herein facilitate the measurement of the different analytes by varying the bias of the electrodes provides an easy and rapid device for analyte measurement. In some examples, the ability to measure oxygen concentration can be enhanced by including a solid-state electrolyte layer. In this example, the solid-state electrolyte layer can help to minimize the risk of an electrical short being caused by the oxidation-reduction reaction between the electrodes used to measure oxygen concentration. In this manner, without being bound to any particular theory, it is believed that the solid-state electrolyte layer helps inhibit dendrite growth at the electrode.

Analyte Sensor Environment

FIG. 1 illustrates an example environment 100 including an analyte sensor system 102. The analyte sensor system 102 is coupled to a host 101, which may be a human patient. In some examples, the host 101 is subject to a temporary or permanent diabetes condition or other health condition that makes analyte monitoring useful. In some examples, the host 101 is a diabetic patient. In some examples, the host 101 is a jogger, climber, or the like monitoring oxygen concentration. In some examples, the host 101 is a pulmonary patient.

The analyte sensor system 102 includes an analyte sensor 104. In some examples, the analyte sensor 104 is or includes a glucose sensor configured to measure a glucose concentration in the host 101. In other examples, analyte sensor is or includes an oxygen sensor configured to measure an oxygen concentration in the host 101. Also, in some examples, the analyte sensor 104 is a multi-analyte sensor that can measure the concentration of different analytes in the host 101, for example, under different bias conditions as described herein. In examples where the analyte sensor 104 is arranged to measure glucose, the glucose detected can be D-glucose. However, in some example arrangements, the analyte sensor 104 may detect any stereoisomer or blend of stereoisomers of glucose as well as any glucose in an open-chain form, cyclic form, or a mixture thereof.

At least a portion the analyte sensor 104 can be exposed to analyte at the host 101 in any suitable way. In some examples, the analyte sensor 104 is fully implantable under the skin of the host 101. In other examples, the analyte sensor 104 is wearable ex vivo on the body of the host 101 (e.g., on the body but not under the skin). Also, in some examples, the analyte sensor 104 is a transcutaneous device (e.g., with a sensor residing at least partially under or in the skin of a host). In the example of FIG. 1, the analyte sensor system 102 also includes sensor electronics 106. In some examples, the sensor electronics 106 and analyte sensor 104 are provided in a single integrated package. In other examples, the analyte sensor 104 and sensor electronics 106 are provided as separate components or modules. For example, the analyte sensor system 102 may include a disposable (e.g., single use) sensor mounting unit (FIG. 3) that may include the analyte sensor 104, a component for attaching the analyte sensor 104 to a host (e.g., an adhesive pad), and/or a mounting structure configured to receive a sensor electronics unit including some or all of the sensor electronics 106 shown in FIG. 2. The sensor electronics unit may be reusable. The sensor electronics 106 may be programmed and/or arranged to perform various operations as described herein. For example, the sensor electronics 106 may apply bias conditions to the analyte sensor 104, may receive a raw sensor signal from the analyte sensor 104, convert a raw sensor signal to a corresponding analyte concentration, and/or the like.

The analyte sensor 104 may use any known method, including invasive, minimally-invasive, or non-invasive sensing techniques (e.g., optically excited fluorescence, microneedle, transdermal monitoring of glucose), to provide a raw sensor signal indicative of the concentration of the analyte in the host 101. The raw sensor signal may be converted into calibrated and/or filtered analyte concentration data used to provide a useful value of the analyte concentration (e.g., estimated blood glucose concentration level and/or estimated dissolved oxygen concentration level) to a user, such as the host or a caretaker (e.g., a parent, a relative, a guardian, a teacher, a doctor, a nurse, or any other individual that has an interest in the wellbeing of the host 101).

In some examples, the analyte sensor 104 is or includes a continuous glucose monitoring sensor. In some other examples, the analyte sensor 104 is or includes a continuous oxygen concentration sensor. In some further examples, the analyte sensor 104 can be switched between a glucose sensing mode and an oxygen sensing mode. Depending upon the example, the modes discussed herein may also be described a "configuration." The analyte sensor can be or include a subcutaneous, transdermal (e.g., transcutaneous), and/or intravascular device. In some aspects, such a sensor or device may recurrently (e.g., periodically or intermittently) analyze sensor data. The analyte sensor 104 may use any method of glucose and/or oxygen measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DEXCOM®, (e.g., the DEXCOM G5® sensor, the DEXCOM G6® sensor, the DEXCOM G7™ sensor and/or variations thereof). In some further examples, analyte sensor 104 can be configured to detect lactate.

The environment 100 may also include a second medical device 108. The second medical device 108 may be or include a drug delivery device such as an insulin pump or an insulin pen. In some examples, the second medical device 108 includes one or more sensors, such as another analyte sensor, a heart rate sensor, a respiration sensor, a motion sensor (e.g., accelerometer), posture sensor (e.g., 3-axis accelerometer), acoustic sensor (e.g., to capture ambient sound or sounds inside the body). The second medical device 108 may be wearable, e.g., on a watch, glasses, contact lens, patch, wristband, ankle band, or another wearable item, or may be incorporated into a handheld device (e.g., a smartphone). In some examples, the medical device 108 includes a multi-sensor patch that may, for example, detect one or more of an analyte level (e.g., glucose, lactate, ketone, uric acid, creatinine, glycerol, insulin, or other substance), heart rate, respiration (e.g., using impedance), activity (e.g., using an accelerometer), posture (e.g., using an accelerometer), galvanic skin response, tissue fluid levels (e.g., using impedance or pressure).

In some examples, the analyte sensor system 102 and the second medical device 108 communicate with one another, that is, the analyte sensor system 102 and the second medical device 108 are communicatively coupled such as to enable two-way communication. Communication between the analyte sensor system 102 and second medical device 108 may occur over any suitable wired connection and/or via a wireless communication signal 110. For example, the analyte sensor system 102 may be configured to communicate using via radio frequency (e.g., Bluetooth, Medical Implant Communication System (MICS), Wi-Fi, near field communication (NFC), radio frequency identification (RFID), Zigbee, Z-Wave or other communication protocols), optically (e.g., infrared), sonically (e.g., ultrasonic), or a cellular protocol (e.g., Code Division Multiple Access (CDMA) or Global System for Mobiles (GSM)), or via a wired connection (e.g., serial, parallel, etc.).

In some examples, the environment 100 also includes a wearable sensor 130. The wearable sensor 130 can include a sensor circuit (e.g., a sensor circuit configured to detect a glucose concentration or other analyte concentration) and a communication circuit, which may, for example, be an NFC circuit. In some examples, information from the wearable sensor 130 may be retrieved from the wearable sensor 130 using a user computer device 132, such as a smart phone, that is configured to communicate with the wearable sensor 130 via the wearable sensor's communication circuit, for example, when the user computer device 132 is placed near the wearable sensor 130. For example, swiping the user computer device 132 over the sensor 130 may retrieve sensor data from the wearable sensor 130 using NFC or other suitable wireless communication. The use of NFC communication may reduce power consumption by the wearable sensor 130, which may reduce the size of a power source (e.g., battery or capacitor) in the wearable sensor 130 or extend the usable life of the power source. In some examples, the wearable sensor 130 may be wearable on an upper arm as shown. In some examples, a wearable sensor 130 may additionally or alternatively be on the upper torso of the patient (e.g., over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 such as a watch, and an additional wearable sensor 130 may communicate with one another via wired or wireless (e.g., Bluetooth, MICS, NFC or any of the other options described above,) communication. The additional wearable sensor 130 may be any of the examples described above with respect to medical device 108. The analyte sensor system 102, medical device 108, and additional wearable sensor 130 on the host 101 are provided for illustration and description and are not necessarily drawn to scale.

The environment 100 may also include one or more computing devices, such as a hand-held smart device (e.g., smart device) 112, tablet 114, smart pen 116 (e.g., insulin delivery pen with processing and communication capability), computer 118, a wearable device 120 such as a watch, or peripheral medical device 122 (which may be a proprietary device such as a proprietary user device available from DexCom), any of which may communicate with the analyte sensor system 102 via a wireless communication signal 110, and may also communicate over a network 124 with a server system (e.g., remote data center) or with a remote terminal 128 to facilitate communication with a remote user (not shown) such as a technical support staff member or a clinician.

The wearable device 120 may include an activity sensor, a heart rate monitor (e.g., light-based sensor or electrode-based sensor), a respiration sensor (e.g., acoustic- or electrode-based), a location sensor (e.g., GPS), or other sensors.

In some examples, the environment 100 includes a server system 126. The server system 126 can include one or more computing devices, such as one or more server computing devices. In some examples, the server system 126 is used to collect analyte data from the analyte sensor system 102 and/or analyte or other data from the plurality of other devices, and to perform analytics on collected data, generate, or apply one or more of universal or individualized models for glucose levels, and communicate such analytics, models, or information based thereon back to one or more of the devices in the environment 100. In some examples, the server system 126 gathers inter-host and/or intra-host break-in data to generate one or more break-in characteristics, as described herein.

The environment 100 may also include a wireless access point (WAP) 138 used to communicatively couple one or more of analyte sensor system 102, network 124, server system 126, medical device 108 or any of the peripheral devices described above. For example, WAP 138 may provide Wi-Fi and/or cellular connectivity within environment 100. Other communication protocols, such as NFC or Bluetooth, may also be used among devices of the environment 100.

Analyte Sensor System

Figure 2:
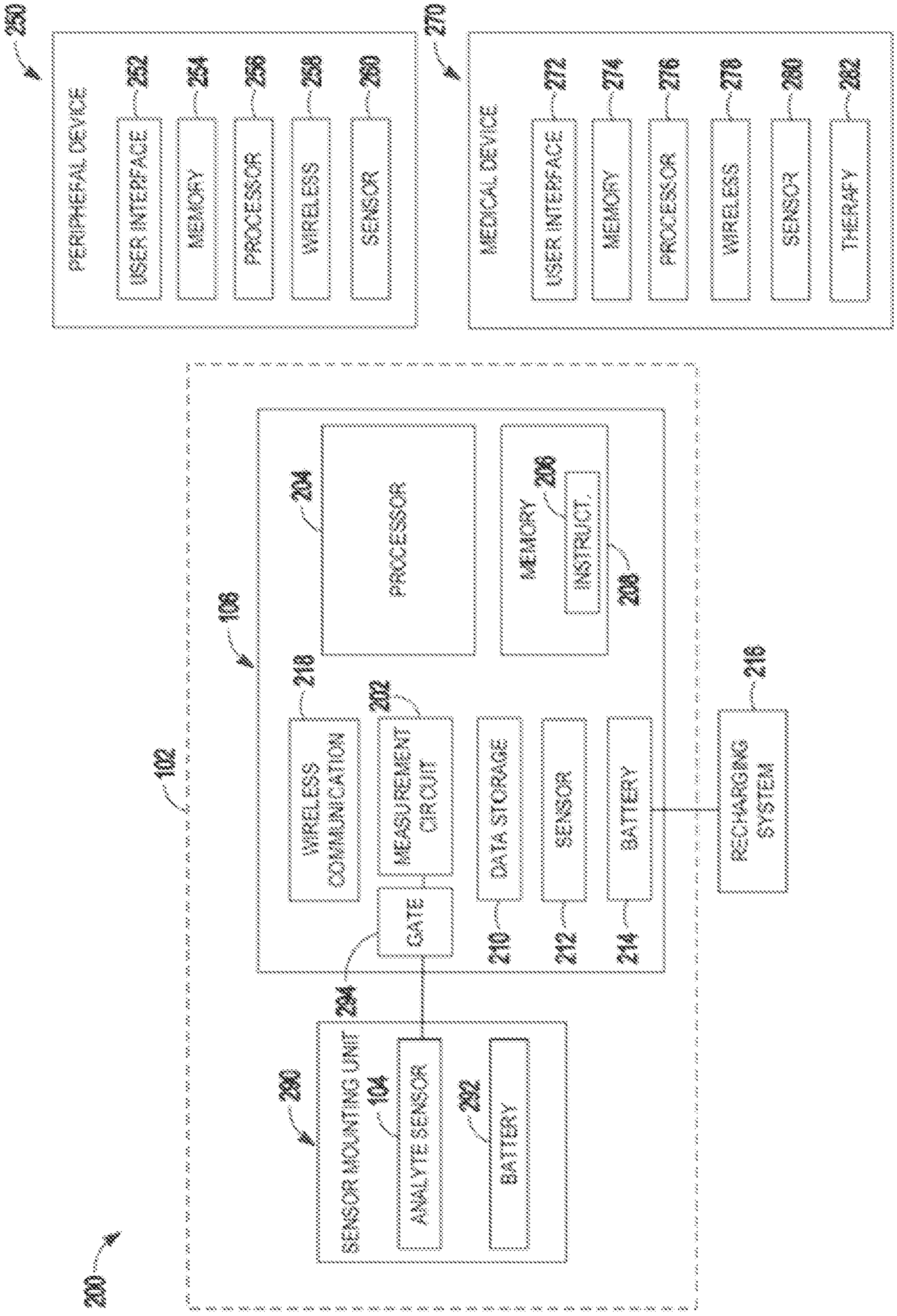
FIG. 2 illustrates an example of a medical device system including the continuous analyte monitoring system of FIG. 1 according to various aspects of the present disclosure.

FIG. 2 illustrates an example of a medical device system 200 including the analyte sensor system 102 of FIG. 1. In the example of FIG. 2, the analyte sensor system 102 includes sensor electronics 106 and a sensor mounting unit 290. While a specific example of division of components between the sensor mounting unit 290 and sensor electronics 106 is shown, it is understood that some examples may include additional components in the sensor mounting unit 290 or in the sensor electronics 106, and that some of the components (e.g., a battery or supercapacitor) that are shown in the sensor electronics 106 may be alternatively or additionally (e.g., redundantly) provided in the sensor mounting unit 290. Also, in some examples, the analyte sensor system 102 may be an integrated system in which the analyte sensor 104 is integrated with the sensor electronics 106. In some examples of an integrated analyte sensor system 102, the sensor mounting unit 290 is omitted and the analyte sensor 104 is mounted to the same substrate or other unit as the sensor electronics 106.

In the example shown in FIG. 2, the sensor mounting unit 290 includes the analyte sensor 104 and a battery 292. In some examples, the sensor mounting unit 290 may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may also include a control circuit 204. The control circuit 204 is configured to control various operations in the analyte sensor system 102. For example, the control circuit 204 may be configured to control application of bias potentials and/or other bias conditions to the analyte sensor 104 via a potentiostat or other suitable component(s) at the measurement circuit 202, interpret raw sensor signals from the analyte sensor 104, and/or compensate for environmental factors. The control circuit 204 may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The control circuit 204 may include suitable hardware for controlling the operations of the analyte sensor system 102, as described herein. In some examples, the control circuit 204 includes one or more processors. The one or more processors may be configured to retrieve instructions 206 from memory 208 and execute the instructions 206 to control the operations of the analyte sensor system 102 as described herein. In some examples, the control circuit 204 includes logic gates for implementing a state machine or other suitable processing hardware.

The sensor electronics 106 may also include a sensor 212, which may be coupled to the control circuit 204. The sensor 212 may be any suitable sensor such as, for example, a temperature sensor, an accelerometer, a location sensor, a blood pressure sensor, a heart rate sensor, a respiration sensor, or another suitable sensor. Although one sensor 212 is shown in FIG. 2, some examples may include multiple sensors at the sensor electronics 106 such as, for example, a temperature sensor and an accelerometer, multiple temperature sensors, and/or the like.

The sensor electronics 106 may also include a power source such as a capacitor or battery 214, which may be integrated into the sensor electronics 106, or may be removable, or part of a separate electronics unit. The battery 214 (or other power storage component, e.g., capacitor) may optionally be rechargeable via a wired or wireless (e.g., inductive or ultrasound) recharging system 216. The recharging system 216 may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component).

The sensor electronics 106 may also include one or more supercapacitors in the sensor electronics unit (as shown), or in the sensor mounting unit 290. For example, the supercapacitor may allow energy to be drawn from the battery 214 in a highly consistent manner to extend the life of the battery 214. The battery 214 may recharge the supercapacitor after the supercapacitor delivers energy to the communication circuit or to the control circuit 204, so that the supercapacitor is prepared for delivery of energy during a subsequent high-load period. In some examples, the supercapacitor may be configured in parallel with the battery 214. A device may be configured to draw energy from the supercapacitor, as opposed to the battery 214. In some examples, a supercapacitor may be configured to receive energy from a rechargeable battery for short-term storage and transfer energy to the rechargeable battery for long-term storage.

The sensor electronics 106 may also include a wireless communication circuit 218, which may for example include a wireless transceiver operatively coupled to an antenna. The wireless communication circuit 218 may be operatively coupled to the control circuit 204 and may be configured to wirelessly communicate with one or more peripheral devices or other medical devices, such as an insulin pump or smart insulin pen. The wireless communication circuit 218 may be configured to communicate according to any suitable wireless protocol or technique including, for example, via radio frequency, optically, sonically, etc.

In the example of FIG. 2, the medical device system 200 also includes an optional peripheral device 250. The peripheral device 250 may be any suitable user computing device such as, for example, a wearable device (e.g., activity monitor), such as a wearable device 120. In other examples, the peripheral device 250 may be a hand-held smart device (e.g., smartphone or other device such as a proprietary handheld device available from Dexcom), a tablet 114, a smart pen 116, or computer 118 shown in FIG. 1.

The peripheral device 250 may include a UI 252, a memory circuit 254, a processor 256, a wireless communication circuit 258, a sensor 260, or any combination thereof. The peripheral device 250 may not necessarily include all the components shown in FIG. 2. The peripheral device 250 may also include a power source, such as a battery.

The UI 252 may, for example, be provided using any suitable input/output device or devices of the peripheral device 250 such as, for example, a touch-screen interface, a microphone (e.g., to receive voice commands), or a speaker, a vibration circuit, or any combination thereof. The UI 252 may receive information from the host or another user (e.g., instructions, glucose values). The UI 252 may also deliver information to the host or other user, for example, by displaying UI elements at the UI 252. For example, UI elements can indicate glucose and/or other analyte concentration values, glucose or other analyte trends, glucose, or other analyte alerts, etc. Trends can be indicated by UI elements such as arrows, graphs, charts, etc.

The processor 256 may be configured to present information to the host 101 or other user, or receive input from the host 101 or other user, via the UI 252. The processor 256 may also be configured to store and retrieve information, such as communication information (e.g., pairing information or data center access information), user information, sensor data or trends, or other information in the memory circuit 254. The wireless communication circuit 258 may include a transceiver and antenna configured to communicate via a wireless protocol, such as any of the wireless protocols described herein. The sensor 260 may, for example, include an accelerometer, a temperature sensor, a location sensor, biometric sensor, or blood glucose sensor, blood pressure sensor, heart rate sensor, respiration sensor, or other physiologic sensor.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., “high glucose level”, “low glucose level” or “fall rate alert” may be communicated via the UI 252 (e.g., via visual display, sound, or vibration). In some examples, the peripheral device 250 may be configured to display or otherwise communicate the sensor information as it is communicated from the sensor electronics 106 (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level). In other examples, the peripheral device 250 may process or interpret the received information (e.g., to declare an alert based on glucose values or a glucose trend). In various examples, the peripheral device 250 may receive information directly from sensor electronics 106, or over a network (e.g., via a cellular or Wi-Fi network that receives information from the sensor electronics 106 or from a device that is communicatively coupled to the sensor electronics 106).

In the example of FIG. 2, the medical device system 200 includes an optional medical device 270. For example, optional the medical device 270 may be used in addition to or instead of the peripheral device 250. The medical device 270 may be or include any suitable type of medical or other computing device including, for example, the medical device 108, peripheral medical device 122, wearable device 120, wearable sensor 130, or wearable sensor 136 shown in FIG. 1. The medical device 270 may include a UI 272, a memory circuit 274, a processor 276, a wireless communication circuit 278, a sensor 280, a therapy circuit 282, or any combination thereof.

Similar to the UI 252, the UI 272 may be provided using any suitable input/output device or devices of the medical device 270 such as, for example, a touch-screen interface, a microphone, or a speaker, a vibration circuit, or any combination thereof. The UI 272 may receive information from the host or another user (e.g., glucose values, alert preferences, calibration coding). The UI 272 may also deliver information to the host or other user, for example, by displaying UI elements at the UI 252. For example, UI elements can indicate glucose, or oxygen, or other analyte concentration values, glucose or other analyte trends, glucose, or other analyte alerts, etc. Trends can be indicated by UI elements such as arrows, graphs, charts, etc.

The processor 276 may be configured to present information to a user, or receive input from a user, via the UI 272. The processor 276 may also be configured to store and retrieve information, such as communication information (e.g., pairing information or data center access information), user information, sensor data or trends, or other information in the memory circuit 274. The wireless communication circuit 278 may include a transceiver and antenna configured communicate via a wireless protocol, such as any of the wireless protocols described herein.

The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one sensor 280 is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof.

In examples where medical device 270 is or includes an insulin pump, the pump and analyte sensor system 102 may be in two-way communication (e.g., so the pump can request a change to an analyte transmission protocol, e.g., request a data point or request data on a more frequent schedule), or the pump and analyte sensor system 102 may communicate using one-way communication (e.g., the pump may receive analyte concentration level information from the analyte sensor system). In one-way communication, a glucose value may be incorporated in an advertisement message, which may be encrypted with a previously-shared key. In a two-way communication, a pump may request a value, which the analyte sensor system 102 may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the medical device system 200 includes two or more peripheral devices and/or medical devices that each receive information directly or indirectly from the analyte sensor system 102. Because different display devices provide many different user interfaces, the content of the data packages (e.g., amount, format, and/or type of data to be displayed, alarms, and the like) may be customized (e.g., programmed differently by the manufacturer and/or by an end user) for each particular device. For example, referring now to the example of FIG. 1, a plurality of different peripheral devices may be in direct wireless communication with sensor electronics 106 (e.g., such as an on-skin sensor electronics 106 that are physically connected to the continuous analyte sensor 104) during a sensor session to enable a plurality of different types and/or levels of display and/or functionality associated with the displayable sensor information, or, to save battery power in the analyte sensor system 102, one or more specified devices may communicate with the analyte sensor system 102 and relay (i.e., share) information to other devices directly or through a server system (e.g., a network-connected data center) 126.

Continuous Analyte Sensor

Figure 3:
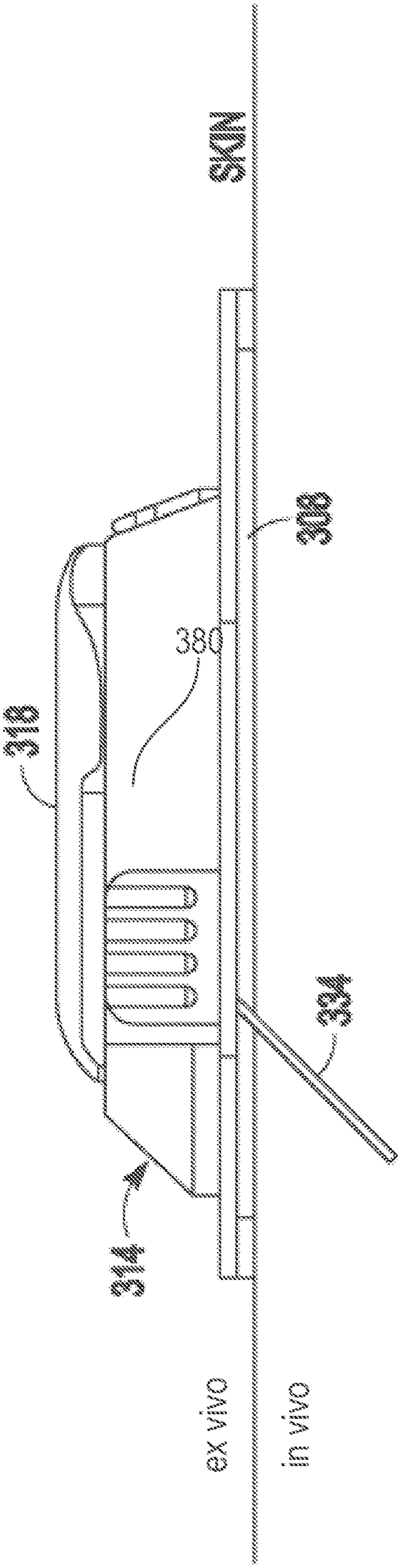
FIG. 3 illustrates an example of a continuous analyte monitoring system that may be implanted into a host according to various aspects of the present disclosure.

FIG. 3 illustrates an example of a transcutaneous sensing system including one or more sensors 334 that may be implanted into a host. A mounting unit 314 may be adhered to the host's skin using an adhesive pad 308. The adhesive pad 308 may be formed from an extensible material, which may be removably attached to the skin using an adhesive. Electronics unit 318 may mechanically couple to the mounting unit 314. In some examples, the electronics unit 318 and mounting unit 314 are arranged in a manner similar to the sensor electronics 106 and sensor mounting unit 290 shown in FIGS. 1 and 2. The analyte sensor 334 may be formed as a coaxial sensor as shown in FIGS. 4A-4J. In other examples, the analyte sensor 334 may be formed as a planar sensor having conductive elements on one or both sides in various configurations.

The layers discussed in at least FIGS. 4A-4G can be formed via one or more pasting/dipping/coating operations, for example, using a die-metered dip coating process. In other examples, electroplating may be used to form some layers, and pasting, dipping, or other coating operations may be used to form other layers, during an iterative process. Examples of methods of forming the sensors and sensor systems discussed herein may be found in currently pending U.S. patent application Ser. No. 16/452,364. Boock et al., incorporated by reference in its entirety herein.

Figure 4A:
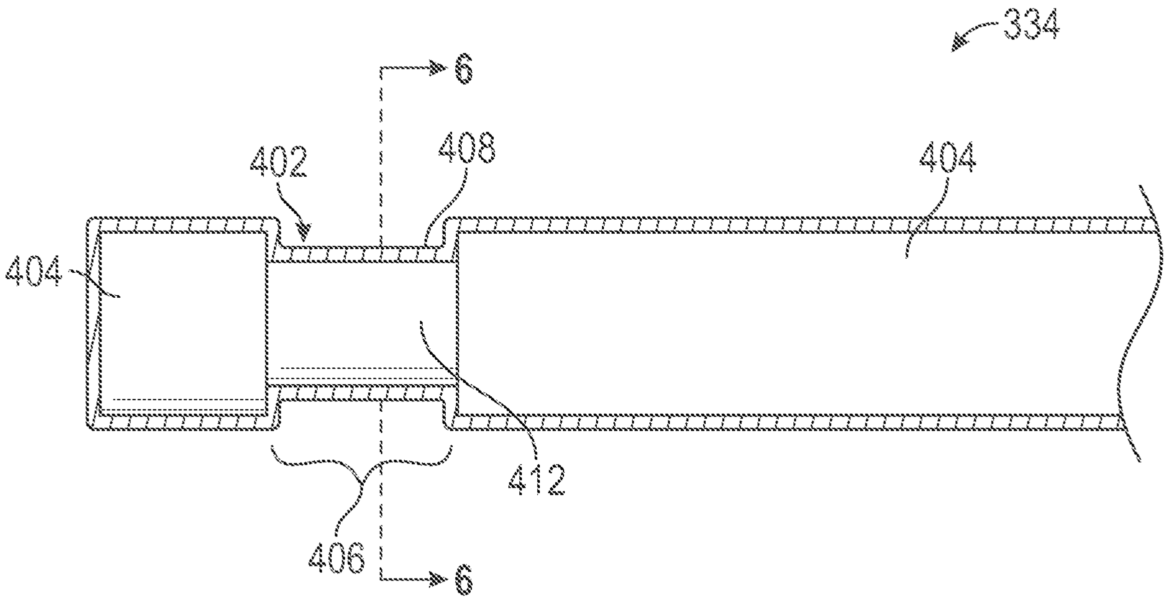
FIG. 4A illustrates an example of the continuous analyte monitoring system according to various aspects of the present disclosure.
Figure 4B:
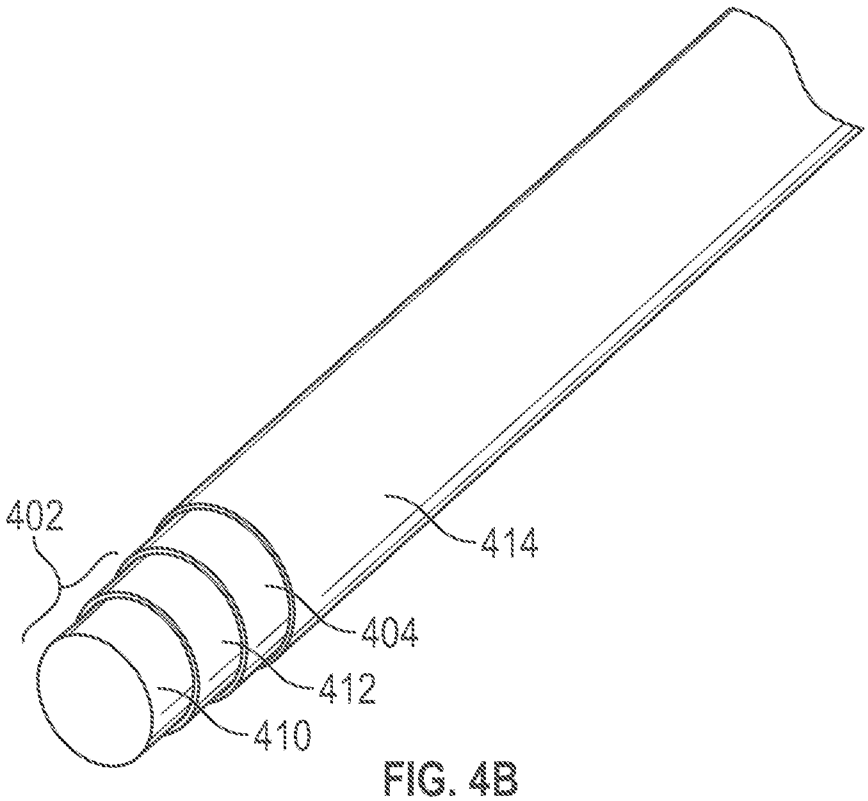
FIG. 4B illustrates an example of the continuous analyte monitoring system according to various aspects of the present disclosure.
Figure 4C:
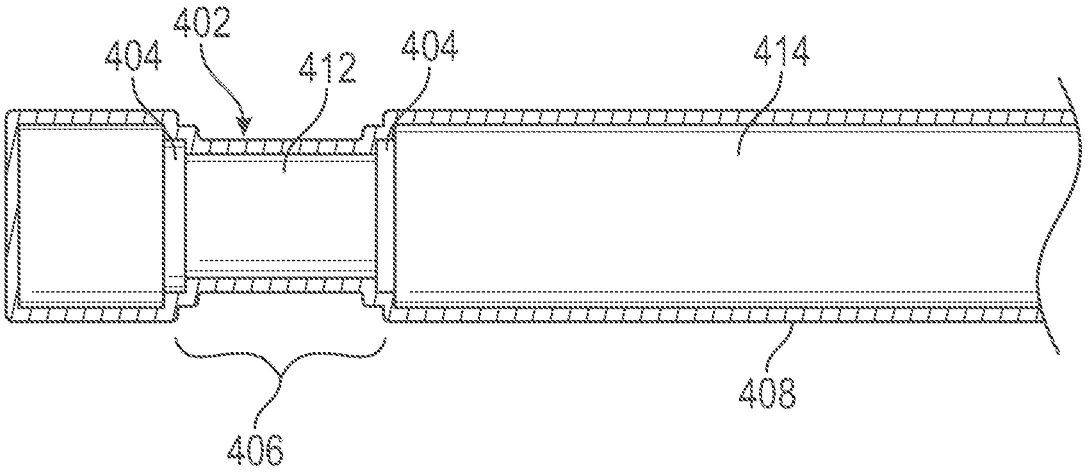
FIG. 4C illustrates an example of the continuous analyte monitoring system according to various aspects of the present disclosure.

FIGS. 4A through 4C illustrate one aspect (e.g., the in vivo portion) of a continuous analyte sensor 334, which includes an elongated conductive body 402. The elongated conductive body 402 includes a core 410 (see FIG. 4B) and a first layer 412 at least partially surrounding the core. The first layer 412 includes a working electrode (e.g., located in window 406) and a membrane 408 located over the working electrode configured and arranged for multi-axis bending. In some aspects, the core 410 and first layer 412 can be of a single material (e.g., platinum). In some aspects, the elongated conductive body 402 is a composite of at least two materials, such as a composite of two conductive materials, or a composite of at least one conductive material and at least one non-conductive material. In some aspects, the elongated conductive body 402 comprises a plurality of layers. In certain aspects, there are at least two concentric (e.g., annular) layers, such as a core 410 formed of a first material and a first layer 412 formed of a second material. However, additional layers can be included in some aspects. In some aspects, the layers are coaxial.

While the elongated conductive body 402 is illustrated in FIGS. 4A through 4C as having a circular cross-section, in other aspects the cross-section of the elongated conductive body can be ovoid, rectangular, triangular, polyhedral, star-shaped, C-shaped, T-shaped, X-shaped, Y-Shaped, irregular, or the like. In one aspect, a conductive wire electrode is employed as a core. To such a clad electrode, two additional conducting layers may be added (e.g., with intervening insulating layers provided for electrical isolation). The conductive layers can be comprised of any suitable material. In certain aspects, it can be desirable to employ a conductive layer comprising conductive particles (e.g., particles of a conductive material) in a polymer or other binder.

Referring again to FIGS. 4A-4C, in some aspects, the first layer 412 is formed of a conductive material. The working electrode 438 is an exposed portion of the surface of the first layer. Accordingly, the first layer is formed of a material configured to provide a suitable electroactive surface for the working electrode.

As shown in FIG. 4B-4C, a second layer 404 surrounds a least a portion of the first layer 412, thereby defining the boundaries of the working electrode. In some aspects, the second layer 404 serves as an insulator and is formed of an insulating material, such as polyimide, polyurethane, parylene, or any other known insulating materials. For example, in one aspect the second layer is disposed on the first layer and configured such that the working electrode is exposed via window 406. In another aspect, an elongated conductive body, including the core, the first layer and the second layer, is provided, and the working electrode is exposed (e.g., formed) by removing a portion of the second layer, thereby forming the window 406 through which the electroactive surface of the working electrode (e.g., the exposed surface of the first layer) is exposed. In some aspects, the working electrode is exposed by (e.g., window 406 is formed by) removing a portion of the second and (optionally) third layers. Removal of coating materials from one or more layers of elongated conductive body (e.g., to expose the electroactive surface of the working electrode) can be performed by hand, excimer lasing, chemical etching, laser ablation, grit-blasting, or the like.

In some aspects, the sensor further comprises a third layer 414 comprising a conductive material. In further aspects, the third layer may comprise a reference electrode, which may be formed of a silver-containing material that is applied onto the second layer (e.g., an insulator). The silver-containing material may include any of a variety of materials and be in various forms, such as, silver/silver chloride (Ag/AgCl)-polymer pastes, paints, polymer-based conducting mixture, and/or inks that are commercially available, for example. The third layer can be processed using a pasting/dipping/coating step, for example, using a die-metered dip coating process. In one aspect, an Ag/AgCl polymer paste is applied to an elongated body by dip-coating the body (e.g., using a meniscus coating technique) and then drawing the body through a die to meter the coating to a precise thickness. In some aspects, multiple coating steps are used to build up the coating to a predetermined thickness. Such a drawing method can be utilized for forming one or more of the electrodes in the device depicted in FIG. 4B.

In some aspects, Ag/AgCl particles are mixed into a polymer, such as polyurethane, polyimide, or the like, to form the silver-containing material for the reference electrode. In some aspects, the third layer is cured, for example, by using an oven or other curing process. In some aspects, a covering of fluid-permeable polymer with conductive particles (e.g., carbon particles) therein is applied over the reference electrode and/or third layer. A layer of insulating material is located over a portion of the silver-containing material, in some aspects.

Over time, such a reference electrode becomes depleted, as silver ions of the silver chloride are converted to silver metal. As silver ions are depleted, reference electrode capacity decreases, reducing the stability of the reference electrode such that analyte sensitivity becomes less linear. By changing this polarity of the bias potential on the reference electrode while in oxygen sensing mode, the reference electrode is able to regenerate by reversing the conversion of silver ions to silver metal. In this manner, silver metal is oxidized to silver ions to advantageously regenerate the capacity of reference electrode while oxygen sensing mode.

Figure 4D:
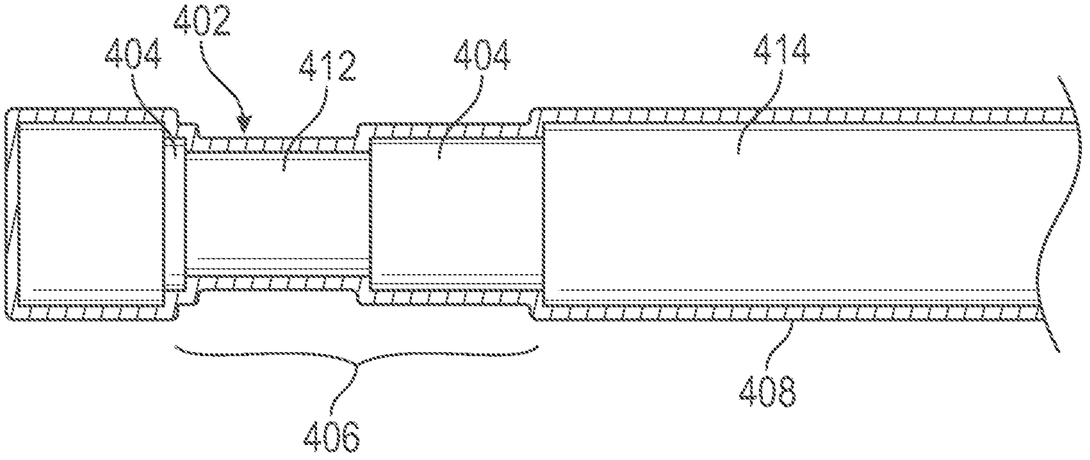
FIG. 4D illustrates an example of the continuous analyte monitoring system according to various aspects of the present disclosure.

As shown in FIGS. 4C and 4D, the sensor also includes a membrane 408 covering at least a portion of the working electrode.

Figure 4E:
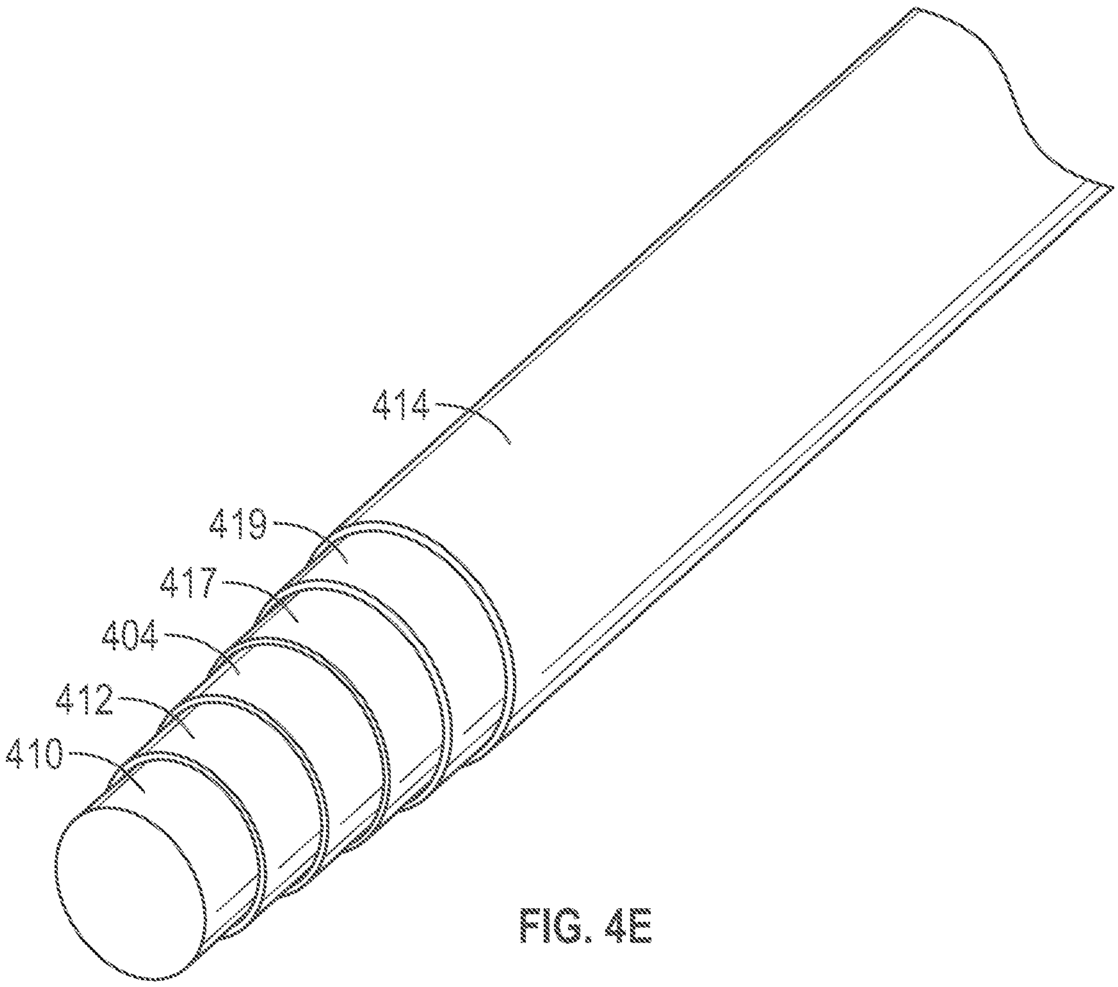
FIG. 4E illustrates an example of the continuous analyte monitoring system according to various aspects of the present disclosure.
Figure 4F:
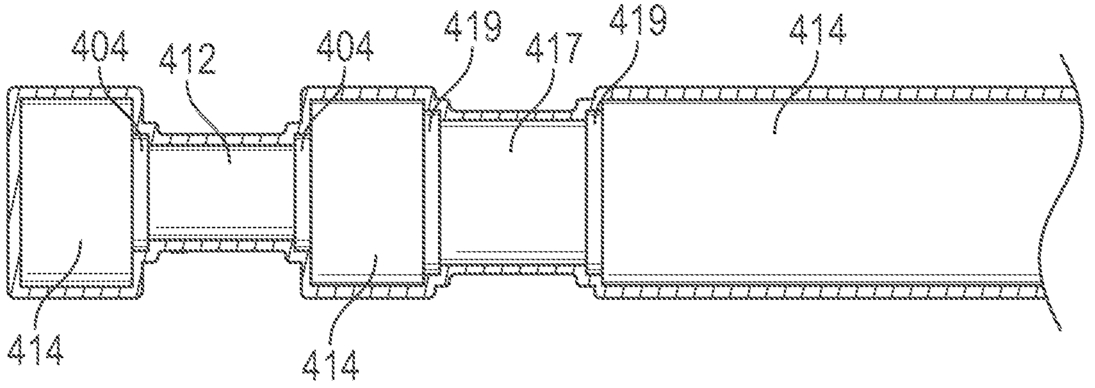
FIG. 4F illustrates an example of the continuous analyte monitoring system according to various aspects of the present disclosure.
Figure 4G:
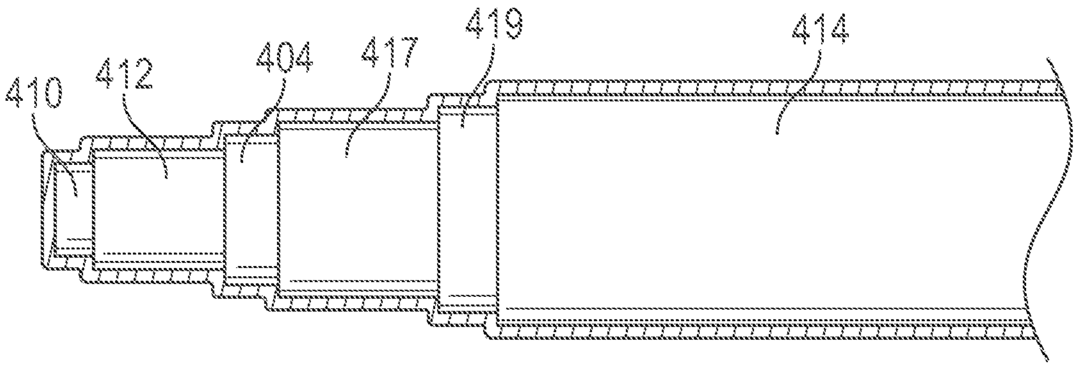
FIG. 4G illustrates an example of the continuous analyte monitoring system according to various aspects of the present disclosure.

FIG. 4B is an illustration showing layers cut away, but in the fabrication process the material typically obtained has all layers ending at a tip. A step of removing layers 404 and 414 can be performed so as to form window(s). FIG. 4D illustrates the results of this removal/cutting away process through a side-view/cross-section. In such a fabrication method involving a continuous strand, the sensors can be singularized after the removal step. In some aspects, if the core is a metal, an end cap may be employed, e.g., by dipping, spraying, shrink tubing, crimp wrapping, etc., an insulating or other isolating material onto the tip. If the core is a polymer (e.g., hydrophobic material), an end cap may not be necessary. For example, in the sensor depicted in FIG. 4D, an end cap (e.g., of a polymer or an insulating material) or other structure may be provided over the core (e.g., if the core 410 is not insulating). FIG. 4E can be considered to build on a general structure as depicted in FIG. 4B, in that two or more additional layers are added to create one or more additional electrodes. Methods for selectively removing two or more windows to create two or more electrodes can also be employed. For example, by adding another conductive layer 417 and insulating layer 419 under a reference electrode layer 414, then two electrodes (e.g., a first and a second working electrode) can be formed, yielding a dual electrode sensor. The dual electrolyte sensor can be configured such that each working electrode detects a signal from a different analyte. In other examples, the operations discussed herein can be used to form a counter electrode, or electrodes to measure additional analytes (e.g., oxygen), and the like, for example. FIG. 4F illustrates a sensor having an additional conductive layer 417 (as compared to FIGS. 4B-4D), wherein the windows are selectively removed to expose working electrode 412 and conductive layer 417 in between a reference electrode (including multiple segments) 414, with a small amount of insulator 404, 419 exposed therebetween. FIG. 4G illustrates another aspect, wherein selective removal of the various layers is stepped to expose the electrode 412 and the conductive layer 417 and insulators 404, 419 along the length of the elongated body.

A bucking strength of the analyte sensor 334 can be in a range of from about 0.010 lbf to 0.10 lbf, or from about 0.02 lbf to about 0.06 lbf, or from less than, equal to, or greater than about 0.01, 0.02, 0.03, 0.03, 0.04, 0.05, 0.06, 0.07, 0.08, 0.09, or 0.10 lbf.

Figure 4I:
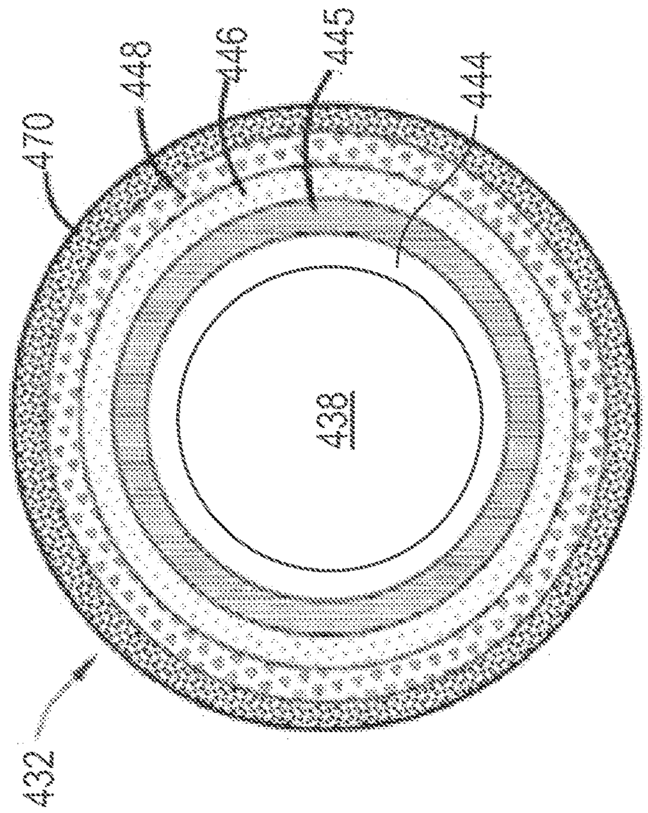
FIG. 4I illustrates an example of the continuous analyte monitoring system according to various aspects of the present disclosure.
Figure 4H:
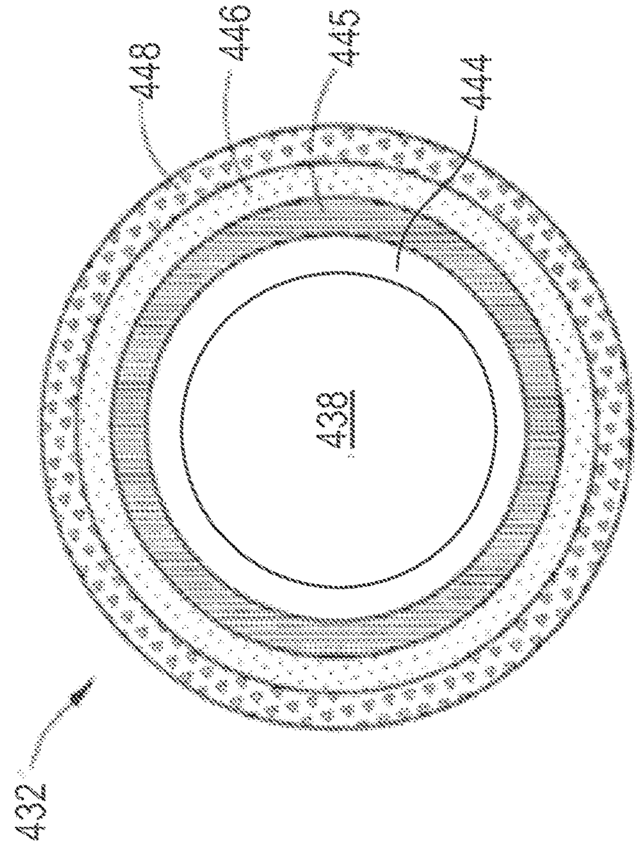
FIG. 4H illustrates an example of the continuous analyte monitoring system according to various aspects of the present disclosure.

FIG. 4H illustrates an example of the sensor of FIG. 4A on line B-B, showing an exposed electroactive surface of at least the working electrode 438 (also referred to as the first layer 412) surrounded by a sensing member 430 (also referred to as the third layer 114). In general, the sensing member 430 of the present disclosure includes a plurality of domains, each having one or more layers, for example, an interference domain 444, an enzyme domain 446, and a resistance domain 448. In some examples, the sensing member 430 may include additional domains, such as a reference electrode domain 445, a cell impermeable domain (not shown), an optional oxygen domain (not shown), an optional drug releasing membrane 470, and/or an optional biointerface membrane (not shown). The reference electrode can be part of the sensing member 430. However, it is understood that a sensing member 430 modified for other sensors, for example, by including various combination of types and configurations domains is within the scope of the present disclosure.

In some examples, one or more domains of the sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones, and block copolymers thereof including, for example, di-block, tri-block, alternating, random, and graft copolymers.

The sensing member 430 can be deposited on the electroactive surfaces of the electrode material using known thin or thick film techniques (for example, spraying, electro-depositing, dipping, roll-to-roll processing, other inline processing, or the like). It is noted that the sensing member 430 that surrounds the working electrode 438 does not have to be the same structure as the sensing member 430 that surrounds a reference electrode, etc. For example, the enzyme domain deposited over the working electrode 438 may be deposited such that it is deposited over the working electrode but is not deposited over the reference and/or counter electrodes.

In the illustrated example, the sensor including the sensing member 430 is an enzyme-based electrochemical sensor. In this example the working electrode 438 measures a product (including but not limited to hydrogen peroxide) produced by the enzyme-catalyzed reaction of glucose. The product detected creates a measurable electronic current. As an example, in detecting glucose, glucose oxidase produces hydrogen peroxide ($H_2O_2$) as a by-product. The produced $H_2O_2$ reacts with the surface of the working electrode 438 producing two protons ($2H^+$), two electrons ($2e^-$) and one molecule of oxygen ($O_2$), which produces the electronic current being detected). as described in more detail above and as is appreciated by one skilled in the art. In some examples, one or more potentiostats are employed to monitor the electrochemical reaction at the electroactive surface of the working electrode(s). The potentiostat applies a constant potential to the working electrode 438 and its associated reference electrode to determine the current produced at the working electrode 438. The current that is produced at the working electrode 438 (and flows through the circuitry to the counter electrode) is substantially proportional to the amount of $H_2O_2$ that diffuses to the working electrode 438. The output signal is may include a raw data stream that is used to provide a useful value of the measured analyte concentration in a host to the host or to a third party such as a medical professional or a guardian, for example.

In addition to the reaction described herein above for detecting glucose concentrations, the sensor described herein can detect oxygen concentrations. According to some examples, measuring oxygen concentrations includes two primary reactions take place on the working electrode:

$$O_2+4H^++4e^-\rightarrow 2H_2O\text{—referred to as the “oxygen current”}$$

$$H_2O_2+2H^++2e^-\rightarrow 2H_2O\text{—referred to as the “}H_2O_2\text{ reduction current”}$$

The above two reactions are balanced by the reaction taking place on the reference electrode:

$$Ag+Cl^-\rightarrow e^-+AgCl$$

In sum “total reduction current”=“oxygen current”+ “$H_2O_2$ reduction current.” To determine How much of the “total reduction current is “oxygen current” and how much is “$H_2O_2$ reduction current,” the following equivalence can be established: “$H_2O_2$ reduction current”=“$H_2O_2$ oxidizing current.” The “oxygen current” can be calculated as:

$$\text{oxygen current}=\text{total reduction current}-H_2O_2\text{ oxidizing current}$$

The resulting “oxygen current” has a linear relationship with the bulk oxygen concentration when oxygen reduction is under oxygen mass transport control. Once the value of “oxygen current” is calculated, the current value can be converted into an oxygen concentration value. As described further herein, detection of glucose concentrations or oxygen concentrations can be driven by selectively applying potential difference (alternatively referred to as a voltage) across the electrodes. In one example, a positive potential difference drives the reaction for detecting glucose concentrations and negative potential difference (e.g., an opposite polarity) drives the reaction for detecting oxygen concentrations.

Figure 14A:
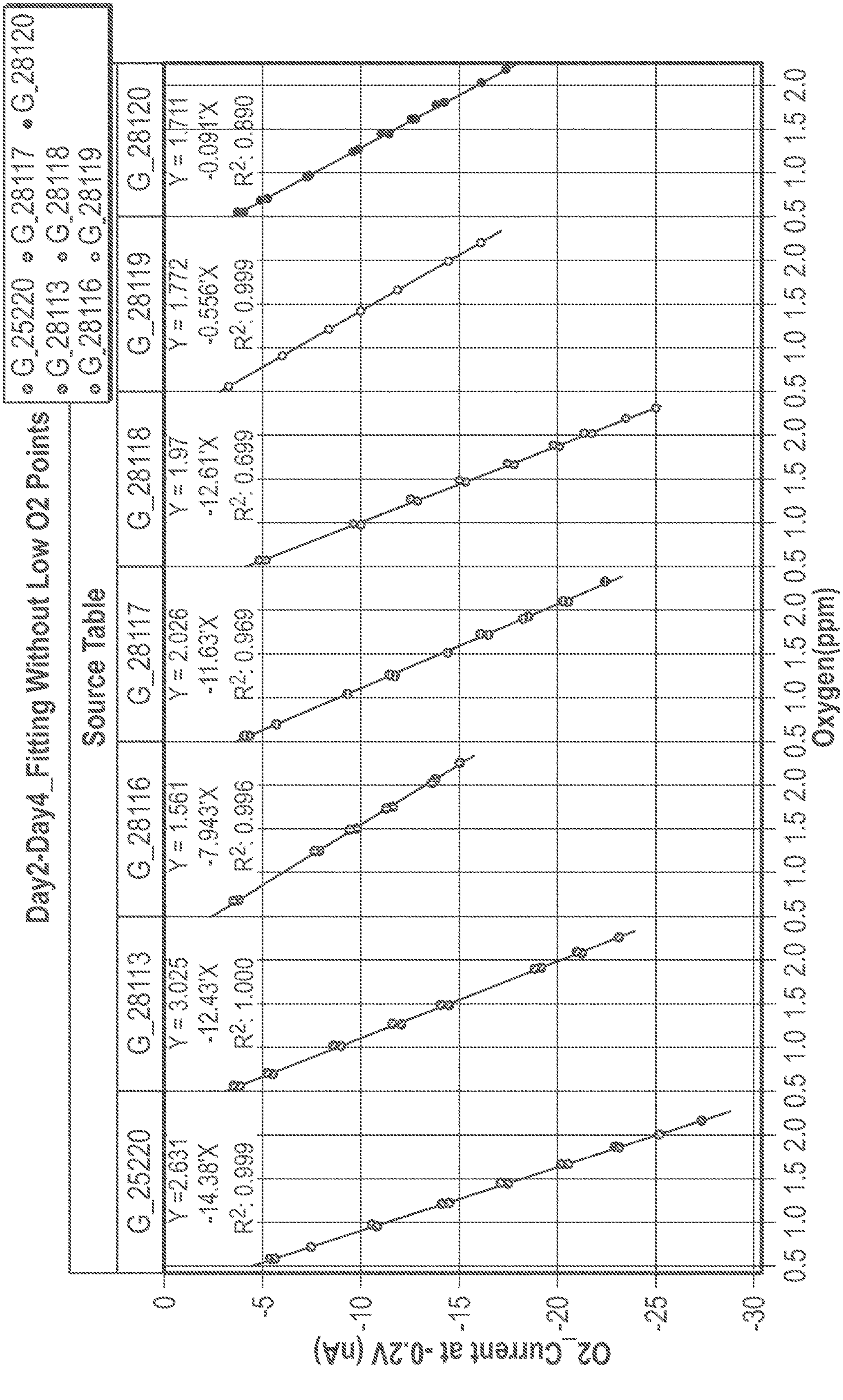
FIGS. 14A-14F demonstrate the linear relationship between the oxygen current vs. oxygen concentration at different glucose concentrations and days according to various aspects of the present disclosure.
Figure 14B:
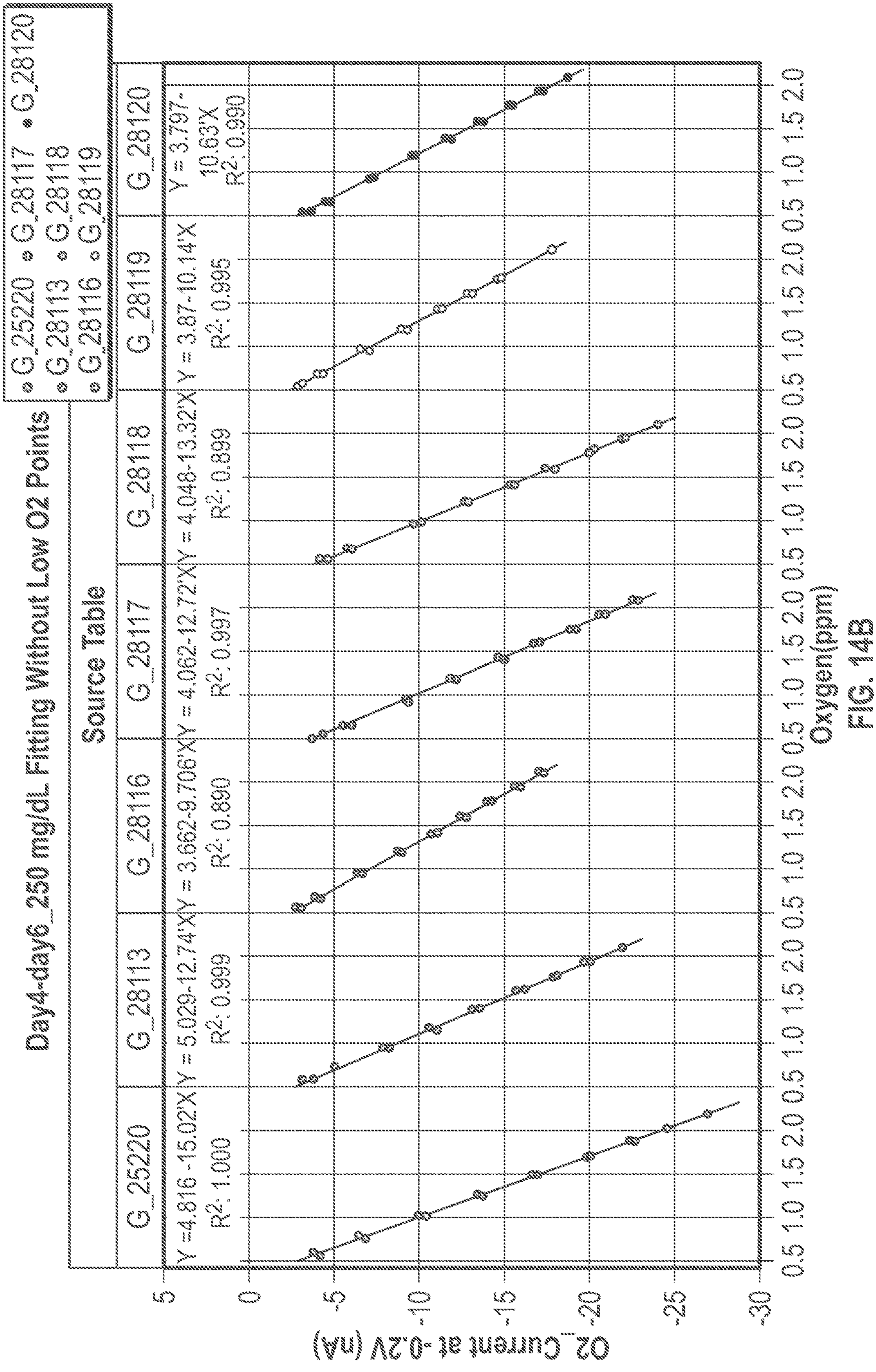
Figure 14C:
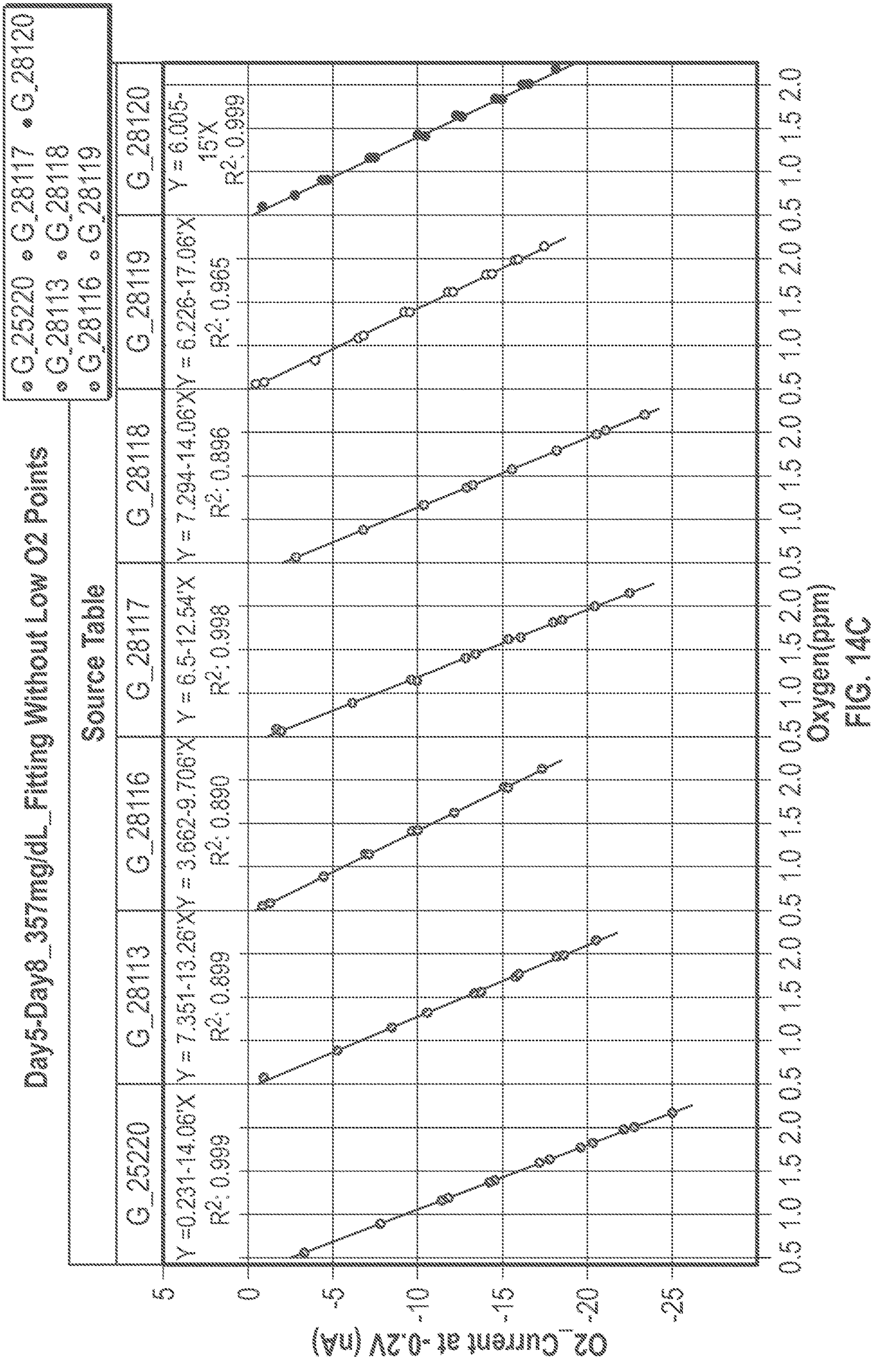
Figure 14D:
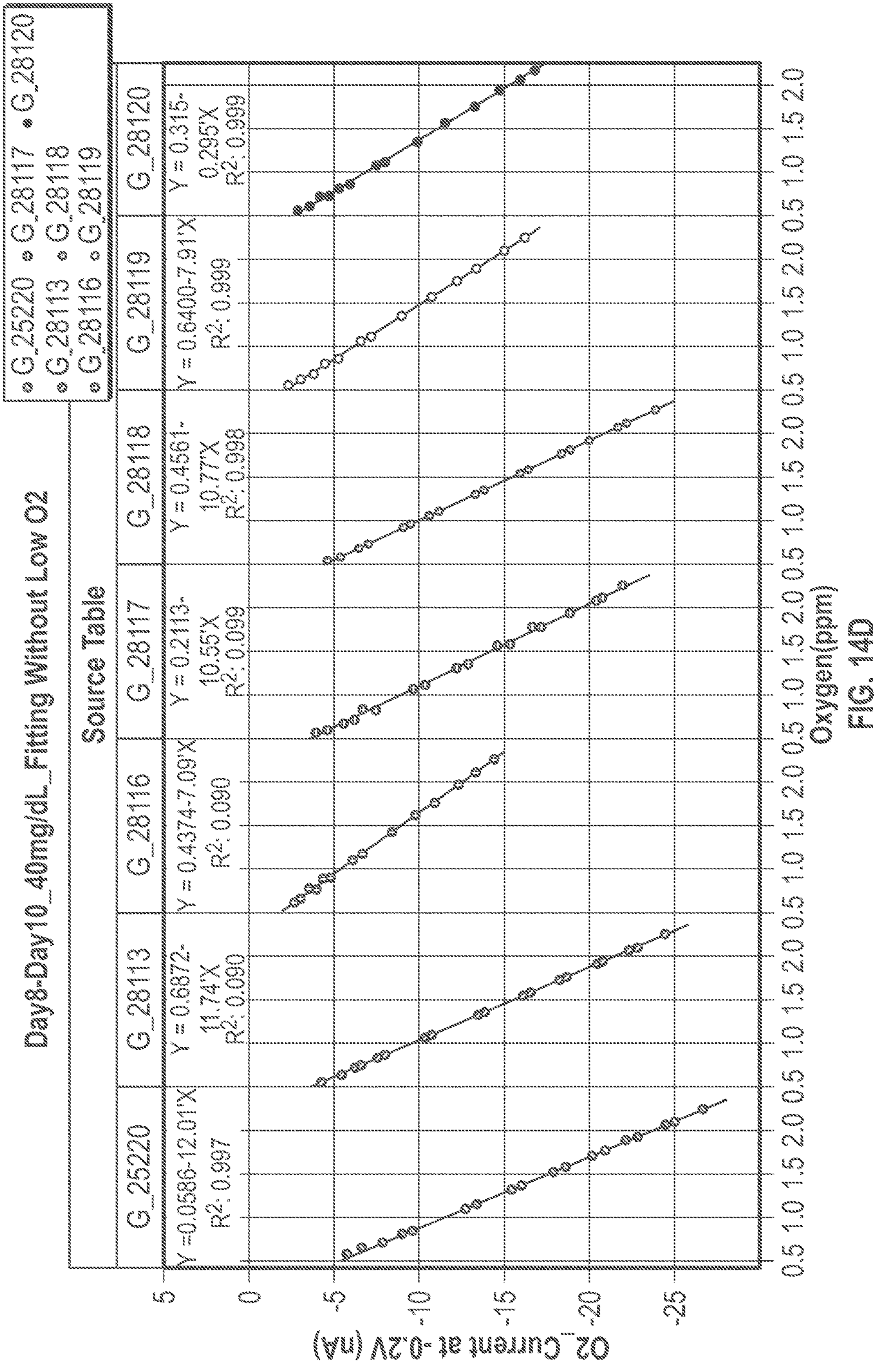
Figure 14E:
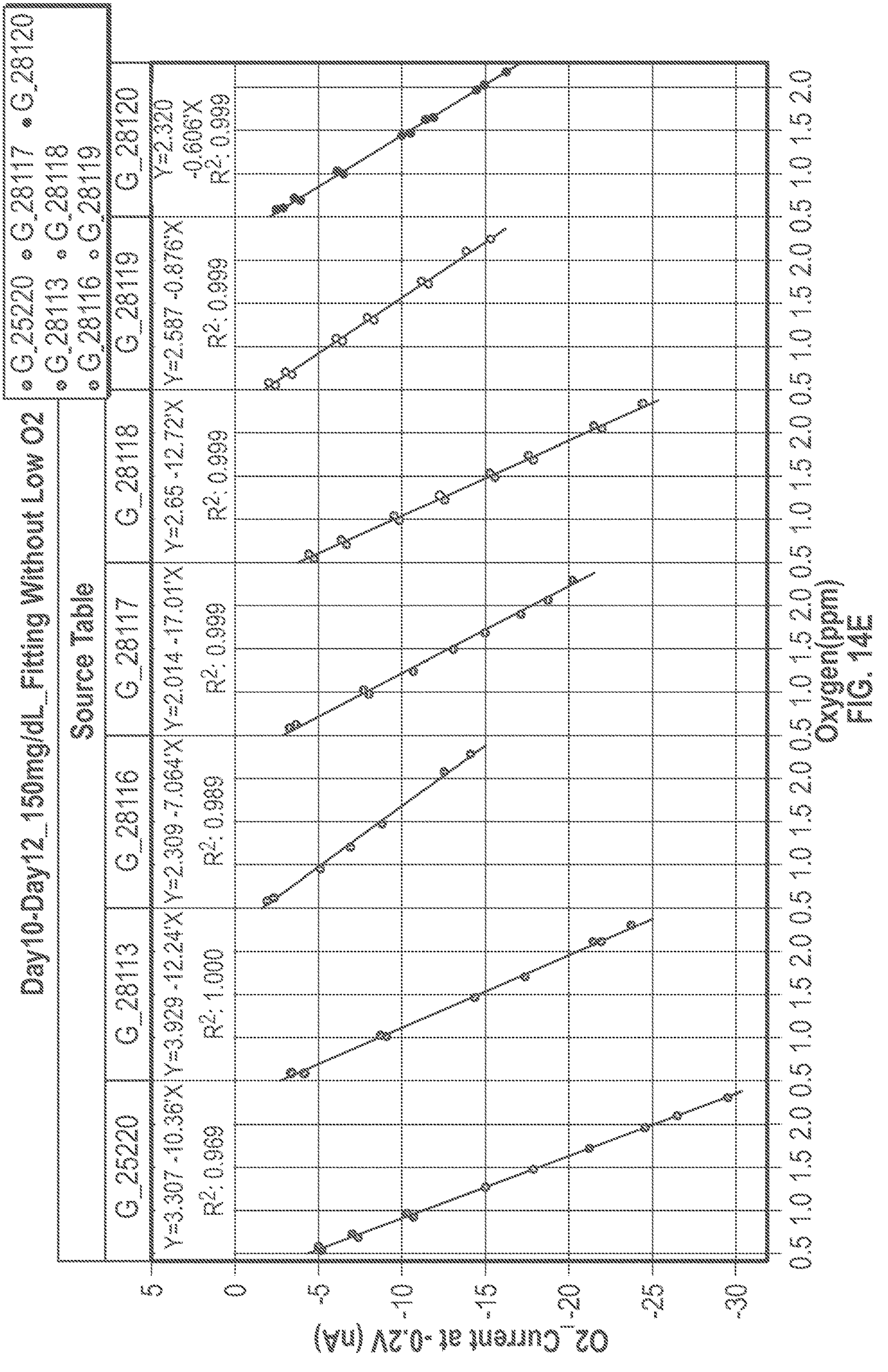
Figure 14F:
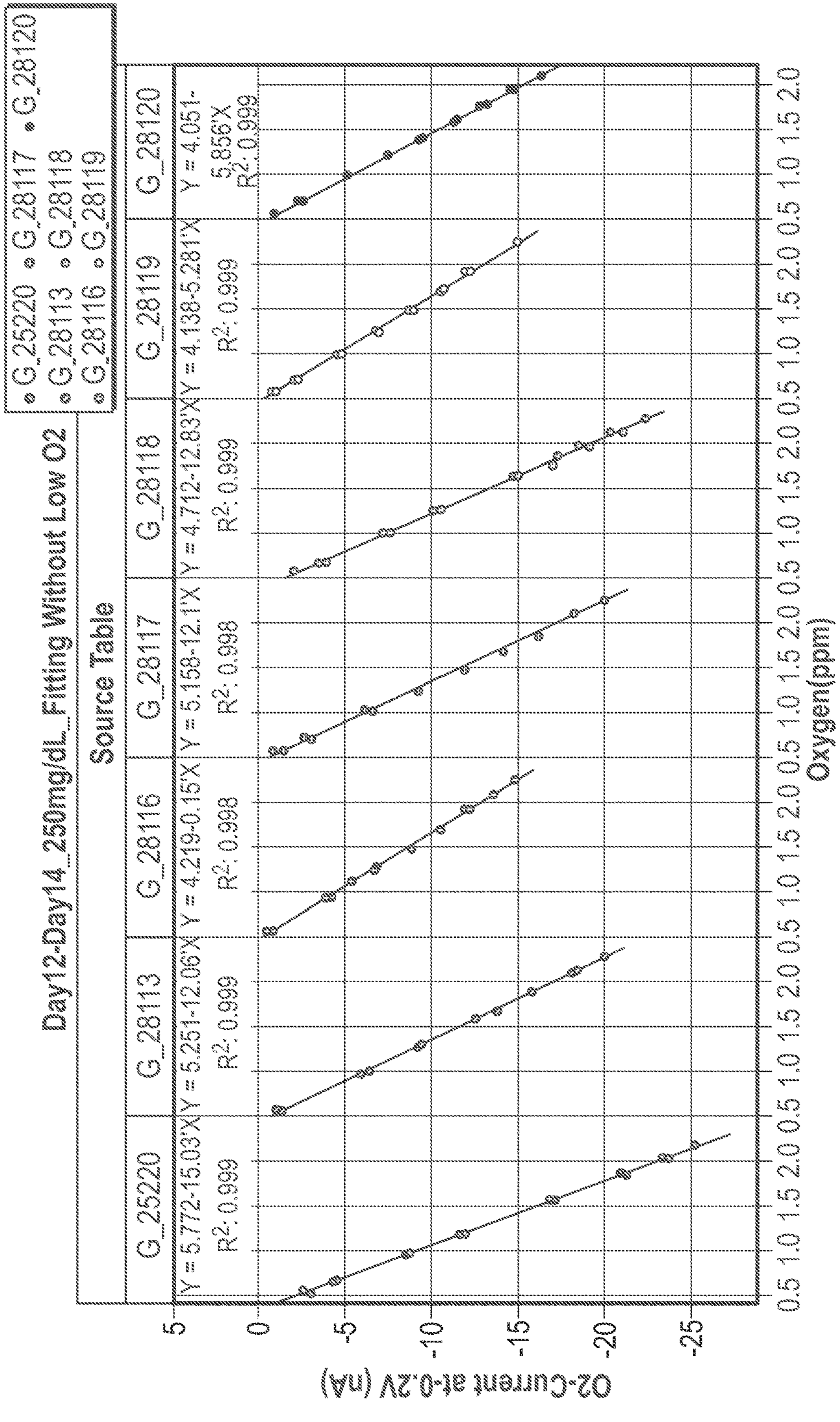

FIGS. 14A-14F demonstrate the linear relationship between the oxygen current vs. oxygen concentration at different glucose concentrations and days. For example, FIG. 14A shows the relationship of oxygen current vs. 150 mg/dL of glucose concentration at day2-day4. FIG. 14B shows the relationship of oxygen current vs. 250 mg/dL of glucose concentration at day4-day6. FIG. 14C shows the relationship of oxygen current vs. 350 mg/dL of glucose concentration at day6-day8. FIG. 14D shows the relationship of oxygen current vs. 40 mg/dL of glucose concentration at day8-day10. FIG. 14E shows the relationship of oxygen current vs. 150 mg/dL of glucose concentration at day10-day12. FIG. 14F shows the relationship of oxygen current vs. 250 mg/dL of glucose concentration at day12-day14. In FIGS. 14A-14F, current from reduction reaction is presented as negative current and all current by oxidation reaction is presented as positive current.

FIG. 4I illustrates an example of the sensor of FIG. 4A on line C-C, showing a non-exposed electroactive surface of at least a working electrode 438 surrounded by a sensing member 430 including a plurality of domains or layers, for example, the interference domain 444, the enzyme domain 446, and the resistance domain 448. In other examples, the sensing member 420 can include one or more additional domains/membranes, such as an electrode domain, a cell impermeable domain (not shown), an oxygen domain (not shown), a drug releasing membrane 470, and/or a biointerface membrane (not shown), such as described in more detail below. As shown in FIG. 4C, the drug releasing membrane 470 is positioned adjacent to working electrode 438 surface and does not cover working electrode 438 or the plurality of domains or layers, for example, the interference domain 444, the enzyme domain 446, and the resistance domain 448, of the sensing member 430. In one example, the drug releasing membrane 470 is positioned at the distal end 437 of sensor 434.

Figure 4J:
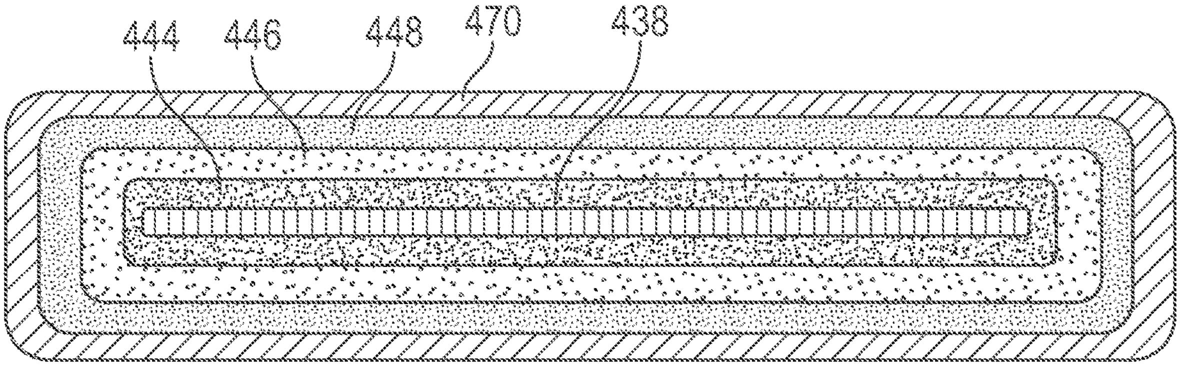
FIG. 4J illustrates an example of the continuous analyte monitoring system according to various aspects of the present disclosure.

FIG. 4J shows an exposed electroactive surface of at least a working electrode 438 surrounded by a sensing membrane. Similar to the circular sensor shown in FIG. 4B, the planar version can include a sensing membrane with multiple layers or domains. For example, the planar version can include an interference domain 444, an enzyme domain 446, and resistance domain 448, in addition to other variations of domains, such as drug releasing membrane 470 as discussed above.

In some examples, the sensor can be configured for transcutaneous or short-term subcutaneous implantation, and can have a thickness from about 0.5 μm to about 8 μm, and sometimes from about 4 μm to about 6 μm. In one sensor configured for fluid communication with a host's circulatory system, the thickness can be from about 1.5 μm to about 25 μm, and sometimes from about 3 to about 15 μm. It is also contemplated that in some examples, the biointerface/drug releasing layer or any other layer of the electrode can have a thickness that is consistent, but in other examples, the thickness can vary horizontally and/or vertically with reference to the sensing region. For example, in some examples, the presence and/or thickness of the biointerface/drug releasing layer can vary along the longitudinal axis of the electrode end.

Figure 5:
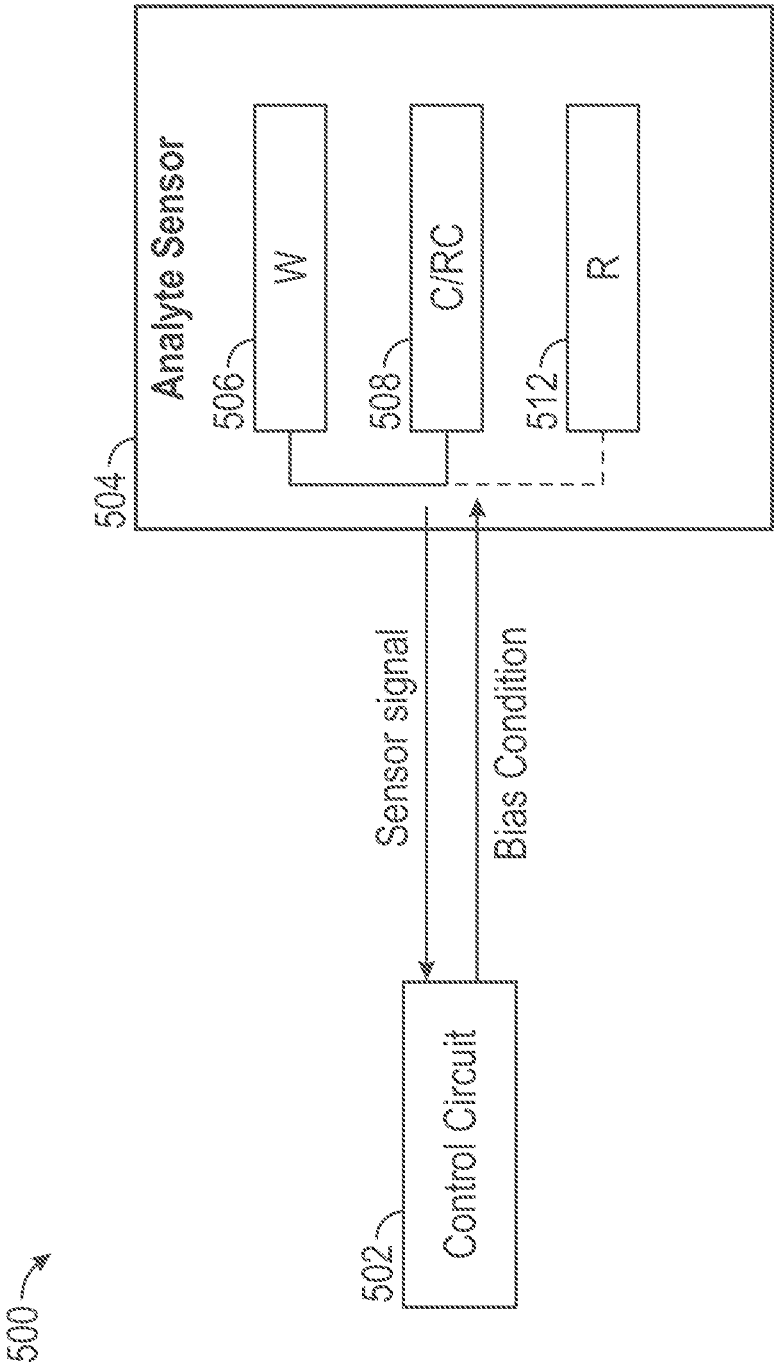
FIG. 5 illustrates an example of an example sensor system that is arranged to selectively transition between a first configuration for measuring a first analyte and a second configuration for measuring a second analyte according to various aspects of the present disclosure.

FIG. 5 illustrates an example of sensor system 500 that is arranged to selectively transition between a first configuration for measuring a first analyte and a second configuration for measuring a second analyte. The sensor system 500 may be arranged similar to the various sensor systems described herein such as, for example, the analyte sensor system 102. The sensor system 500 comprises an analyte sensor 504 and a control circuit 502. The control circuit 502 may comprise a processor or other circuit components for controlling the analyte sensor 504. The control circuit 502 may also comprise biasing circuit for generating a bias signal to be provided to the analyte sensor 504 according to one or more bias conditions.

The analyte sensor 504 may comprise electrodes 506, 508 and optional electrode 512. The analyte sensor 504 may be arranged, for example, similar to various other analyte sensors described herein such as, for example those include a solid-state electrolyte layer as described further herein. In a three-electrode arrangement, the control circuit 502 may provide a bias condition to the analyte sensor 504 by providing a potential difference between the working electrode 506 and the reference electrode 512. Providing the bias condition to the analyte sensor 504 may prompt an electrochemical reaction resulting in a current between the working electrode 506 and the counter electrode 508. In a two-electrode arrangement (e.g., when the reference electrode 512 is omitted), the control circuit 502 may provide a bias condition by providing a potential difference between the working electrode and the counter electrode 508, which may act as a reference-counter electrode as described herein. The bias condition may prompt an electrochemical reaction that results in a current between the working electrode 506 and the reference-counter electrode 508.

In some examples, the control circuit 502 is configured to selectively change the bias condition provided to the analyte sensor 504 to cause the analyte sensor 504 to generate a sensor signal (e.g., current) indicating concentrations of different analytes. For example, under a first bias condition, the analyte sensor 504 generates a sensor signal indicating a concentration of the first analyte. Under a second bias condition, the analyte sensor 504 generates a sensor signal indicating a concentration of the second analyte different than the first analyte. In some examples, the first bias condition is a positive potential, where the working electrode 506 is driven to a potential higher than the reference electrode (which may be the reference-counter electrode 508 in a two-electrode arrangement or the reference electrode 512 in a three-electrode arrangement). The first bias condition can be used to detect the first analyte (e.g., glucose) and the second bias condition can be used to detect the second analyte (e.g., oxygen).

As mentioned herein, the analyte sensor 334 is capable of selectively measuring the concentration of oxygen or glucose in the interstitial fluid. The ability to alternate between an oxygen measurement mode (to sense the concentration of oxygen in the interstitial fluid) and a glucose measurement mode (to sense the concentration of glucose in the interstitial fluid) is a result of the bias condition applied to the working electrode 438 relative to the reference electrode (e.g., the reference electrode 512). In one example, when the system 500 is configured in the glucose measurement mode the working electrode 438 and reference electrode of sensing member 430 are biased to a potential difference of about 0.20 V to about 0.90 V, relative to the reference electrode, about 0.50 V to about 0.70 V about 0.55 V to about 0.65 V, less than, equal to, or greater than about 0.20 V, 0.25, 0.30, 0.35, 0.40, 0.45, 0.50 0.55, 0.60, 0.65, 0.70, 0.75, 0.80, 0.85, or about 0.90 V, relative to the reference electrode. In the oxygen measurement mode, the working electrode 438 is biased at about −0.90 V to about −0.05 V, relative to the reference electrode, about −0.30 V to about −0.20 V, about −0.25 V to about −0.23 V, less than, equal to, or greater than about −0.90 V, −0.85, −0.80, −0.75, −0.70, −0.65, −0.60, −0.55, −0.50 −0.45, −0.40, −0.35, −0.30, −0.25, −0.20, −0.15, −0.10, or, −0.05 V, relative to the reference electrode.

The analyte sensor 334 can be configured to transition from the glucose measurement mode to the oxygen sensing mode or from the oxygen sensing mode to the glucose sensing mode to switch between the glucose measurement mode and the oxygen sensing mode using a sensor control circuit executing respective algorithms for each mode to achieve the described relative bias. The analyte sensor 334 can be configured to alternate between the glucose measurement mode and the oxygen measurement mode according to a predetermined schedule or a user can manually alternate between the glucose measurement mode and the oxygen measurement mode. The analyte sensor 334 can be configured to be in each of the glucose measurement mode and the oxygen measurement mode for equal amounts of time or uneven amounts of time.

In some examples, one cycle where the analyte sensor 334 alternates between the glucose measurement mode and the oxygen measurement mode can last for a time in a range of 60 minutes to 180 minutes, 100 minutes to 140 minutes, less than, equal to, or greater than 60 minutes, 65, 70 75, 80, 85, 90, 95, 100, 105, 110, 115, 120, 125, 130, 135, 140, 145, 150, 155, 160, 165, 170, 175, or 180 minutes. As an illustrative example if the cycle lasts for 120 minutes total, the glucose measurement mode can last for 117 minutes and the oxygen sensing mode can last for 3 minutes. Minimizing the amount of time that the analyte sensor 334 is in the oxygen measurement mode and help to ensure that the same local conditions (glucose and oxygen concentrations) near the analyte sensor 334 are compared to the conditions at glucose sensing mode just before switching to oxygen sensor mode.

In various examples, each of the working electrode 438 and the reference electrode can include many different materials. In one example, the working electrode 438 includes platinum and tantalum and the reference electrode includes silver and silver chloride. In this example, the analyte sensor 334 can be used to selectively measure oxygen and glucose levels in interstitial tissue. In some further examples, the working electrode 438 can include platinum, palladium, rhodium, iridium, tantalum, or a mixture thereof.

Figure 6:
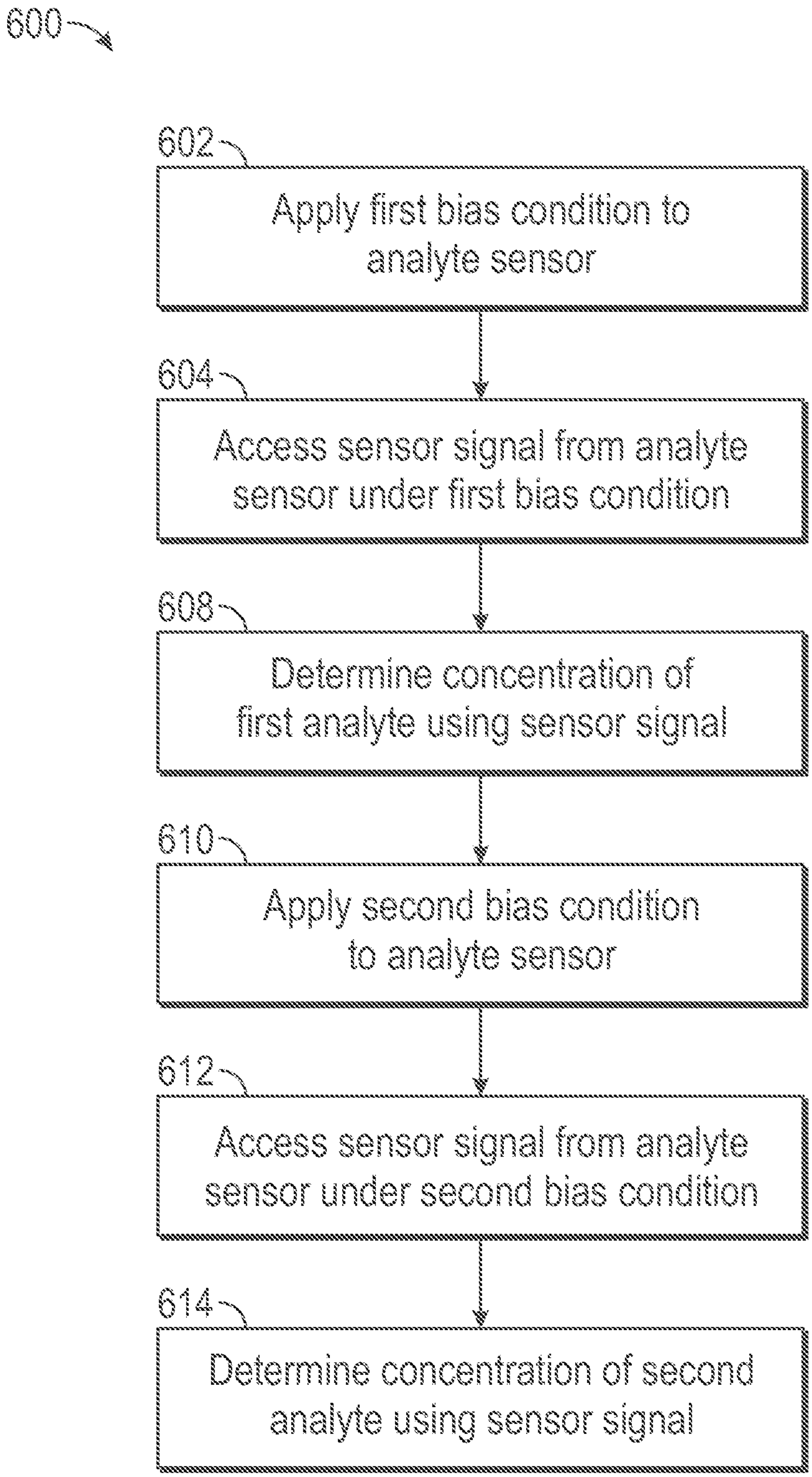
FIG. 6 illustrates an example of a process flow that may be executed in the sensor system of FIG. 5 according to various aspects of the present disclosure.

FIG. 6 illustrates an example of a process flow 600 that may be executed in the sensor system 500 of FIG. 5. At operation 602, the control circuit 502 applies a first bias condition to the analyte sensor 504. In some examples, the applying of the first bias condition to the analyte sensor 504 comprises applying a potential between the working electrode and the reference electrode. At operation 604, a sensor signal as accessed from the analyte sensor 504 under the first bias condition applied at operation 602. At operation 608, a concentration of the first analyte is determined using the sensor signal. At operation 610, a second bias condition is applied to the analyte sensor 504. At operation 612, a sensor signal is accessed from the analyte sensor 504 under the second bias condition. At operation 614, the concentration of the second analyte is determined using the signal accessed from the second bias condition applied at operation 610.

Figure 7:
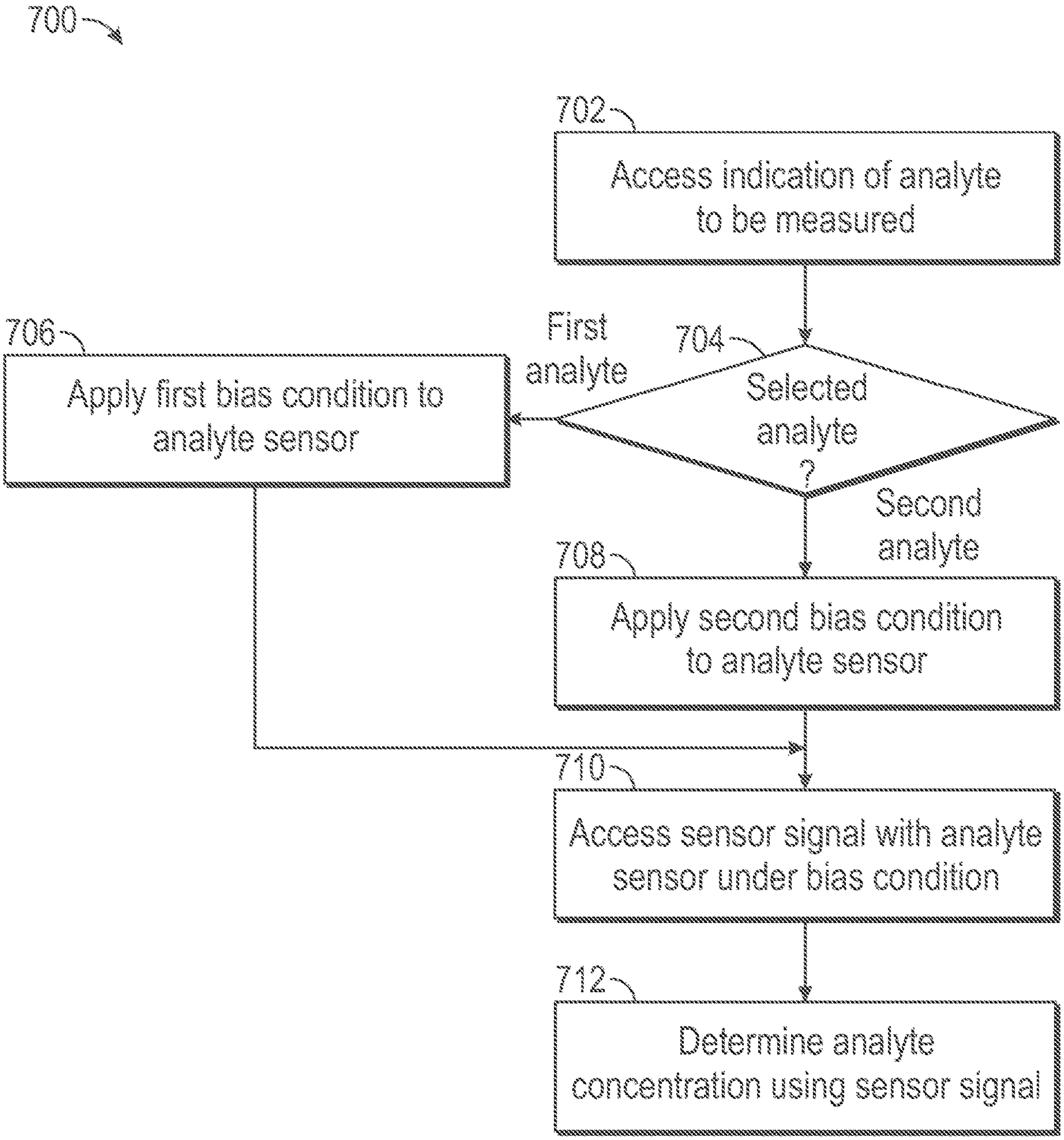
FIG. 7 illustrates an example of a process flow that may be executed in the sensor system of FIG. 5 according to various aspects of the present disclosure.

FIG. 7 illustrates an example of a process flow 700 that may be executed in the sensor system 500 of FIG. 5. At operation 702, the control circuit 502 accesses an indication of an analyte to be measured. The indication of the analyte to be measured may be accessed in any suitable manner. In some examples, the host or other user provides an indication of the analyte using one or more computing devices in communication with the sensor system 500 such as, for example, a smart device, a tablet, a smart pen, a computer, a wearable device, a peripheral medical device and/or the like. In other examples, the indication of the analyte to be measured may be generated by the control circuit 502. For example, the control circuit 502 may measure the first and second analyte periodically according to a determined schedule. The control circuit 502 may generate the indication of the analyte based on which analyte is to be measured at a given time.

Also, in some examples, the control circuit 502 may generate an indication of an analyte to be measured in response to a condition at the analyte sensor 504. Consider an example in which the analyte sensor 504 is configurable to measure glucose and oxygen. In this example, an excessive concentration of oxygen at the analyte sensor 504 while the analyte sensor 504 is configured to measure glucose may degrade the sensor signal generated by the analyte sensor 504. For example, silver ions can migrate to the platinum and destroy the ability for a current to flow between the electrodes. In this example, the control circuit 502 may determine if the sensor signal has degraded while the analyte sensor 504 is configured to measure glucose. If the sensor signal has degraded, the control circuit 502 may reconfigure the analyte sensor 504 to measure oxygen. The resulting determining of oxygen concentration may be used to diagnose the degraded signal observed during glucose measurement.

At operation 704, the control circuit 502 determines if the accessed indication references a first analyte or a second analyte. If the accessed indication references the first analyte, the control circuit 502 applies a first bias condition to the analyte sensor 504 at operation 706. If the accessed indication references a second analyte, the control circuit 502 applies a second bias condition to the analyte sensor 504 at operation 708. The first bias condition may configure the analyte sensor 504 to generate a sensor signal indicative of a concentration of the first analyte and the second bias condition may configure the analyte sensor 504 to generate a sensor signal indicative of a concentration of the second analyte. In examples where the first analyte is glucose, for example, the first bias condition may include applying a positive potential difference between the working electrode 506 and the reference-counter electrode and/or the reference electrode. In examples where the second analyte is oxygen, for example, the second bias condition may include applying a negative potential difference between the working electrode 506 and the reference-counter electrode and/or the reference electrode. At operation 710, the control circuit 502 may access a sensor signal generated while the analyte sensor 504 is under the first bias condition or second bias condition. At operation 712, the control circuit 502 determines a concentration of the selected analyte utilizing the sensor signal, for example, as described herein.

In some examples the process can include a third bias condition. This is because in certain examples if switching for example from a glucose measuring mode, to oxygen measuring mode, and back to glucose measuring mode, it may take time for a sensor to reach electrochemical equilibrium when back in glucose measuring mode. If electrochemical equilibrium is not reached quickly, then the accuracy of the sensor may be impacted.

Figure 15:
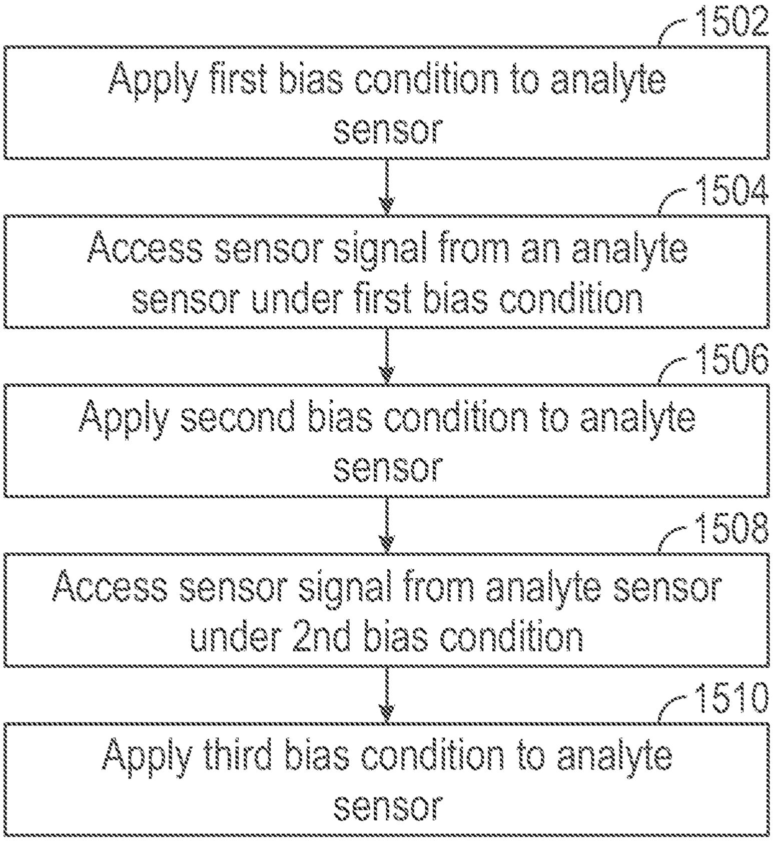
FIG. 15 is a flow chart showing one example of a process for biasing an analyte sensor.

FIG. 15 is a flowchart showing one example of a process 1500 for biasing an analyte sensor. At operation 1502, the control circuit 502 may apply a first bias condition to the analyte sensor, for example, between the working electrode 438 and the reference electrode 414. The first bias condition has a first polarity and a first magnitude. At operation 1504, the control circuit 502 may access a first signal generated by the sensor in vivo while the first bias condition is applied to the sensor. The first signal may indicate a concentration of a first analyte at the host. At operation 1506, the control circuit 502 may apply a second bias condition to the analyte sensor, for example, between the working electrode and the reference electrode. The second bias condition has a second polarity and a second magnitude, where the second polarity is opposite to the first polarity. At operation 1508, the control circuit 502 accesses a second signal generated by the sensor in vivo while the second bias condition is applied to the sensor. The second signal may indicate a concentration of a second analyte at the host. The second analyte can be oxygen if the first analyte is glucose or lactate. At operation 1510, the control circuit 502 may apply a third bias condition to the analyte sensor, for example, between the working electrode 438 and the reference electrode 414. The third bias condition has a third polarity and a third magnitude. The third polarity may be equivalent to the first polarity of the first bias condition. The third magnitude may be greater than the first magnitude of the first bias condition.

In some examples, the first polarity is positive from the working electrode 438 to the reference electrode 414. The second polarity is negative from the working electrode to the reference electrode. As examples, a magnitude of the first bias condition can be in a range of from about 0.5 V and about 0.7 V; a magnitude of the second bias condition can be in a range of from about −0.3V and about −0.2V; a magnitude of the third bias condition can be in a range of from about 0.7V and to about 1.2V.

The third bias condition may be applied for an amount of time that is less than a time that each of the first bias condition and the second bias condition are applied. The relatively short duration of the third bias condition helps to achieve the aforementioned electrochemical equilibrium. The second bias condition may be applied for a time ranging from about 3 times to about 9 times greater or 5 times to 7 times greater than the third bias condition. As non-limiting examples, the second bias condition can applied for a time in range of from about 1 minute to about 10 minutes or 2 minutes to 4 minutes while the third bias condition is applied for a time in a range of from about 10 seconds to about 60 seconds or about 15 seconds to about 45 seconds. Any data obtained during the first, second, and/or third bias conditions can be transmitted by a transmitter capable of transmitting data obtained during the first bias condition, the second bias condition, the third bias condition, or a combination thereof to a device.

Figure 16:
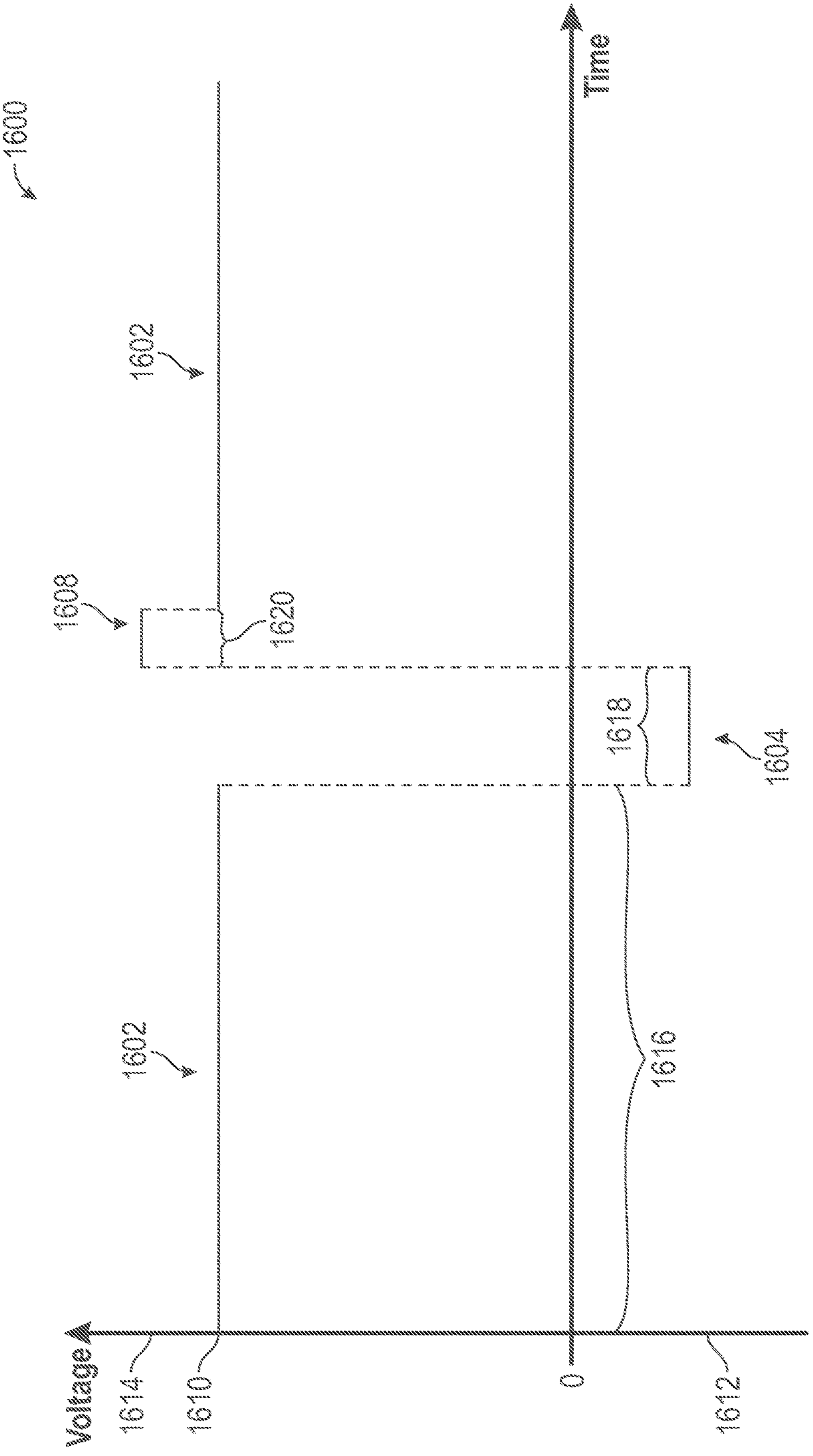
FIG. 16 is a graph showing voltage cycles of the continuous analyte sensor according to various aspects of the present disclosure.

FIG. 16 is a chart 1600 illustrating an example bias signal that may be provided to an analyte sensor, for example, in accordance with the process flow 1500. The chart 1600 includes a horizontal axis indicating time and the vertical axis indicating bias condition magnitude. In the example of FIG. 16, the bias condition magnitude is measured in volts. As during a first time period 1616, a first bias condition 1602 having a first magnitude 1610 is applied to the analyte sensor. During a second time period 1618, a second bias condition 1604 having a second magnitude 1612 is applied to the analyte sensor. During a third time period 1620, a third bias condition having a third magnitude 1614 is applied to the analyte sensor. As illustrated in the example of FIG. 16, the first magnitude 1610 of the first bias condition 1602 is positive and the second magnitude 1612 of the second bias condition 1604 is negative such that the polarity of the first bias condition 1602 and the second bias condition 1604 are opposite. Also, as illustrated in the example of FIG. 16, the third magnitude 1614 of the third bias condition 1608 is greater than the first magnitude 1610 of the first bias condition. Both the first magnitude 1610 and the third magnitude 1614 are positive, and therefore have the same polarity. In some examples, the bias condition arrangement described in FIGS. 16 and 17 may be provided in a cyclic manner. For example, referring to FIG. 16, the first bias condition 1602 may be applied again after the expiration of time period 1620. The first bias condition 1602 may again be applied for a time equal to that of the time period 1616, after which, the second bias condition 1604 may be applied, followed by the third bias condition 1608, and so on.

Figure 8:
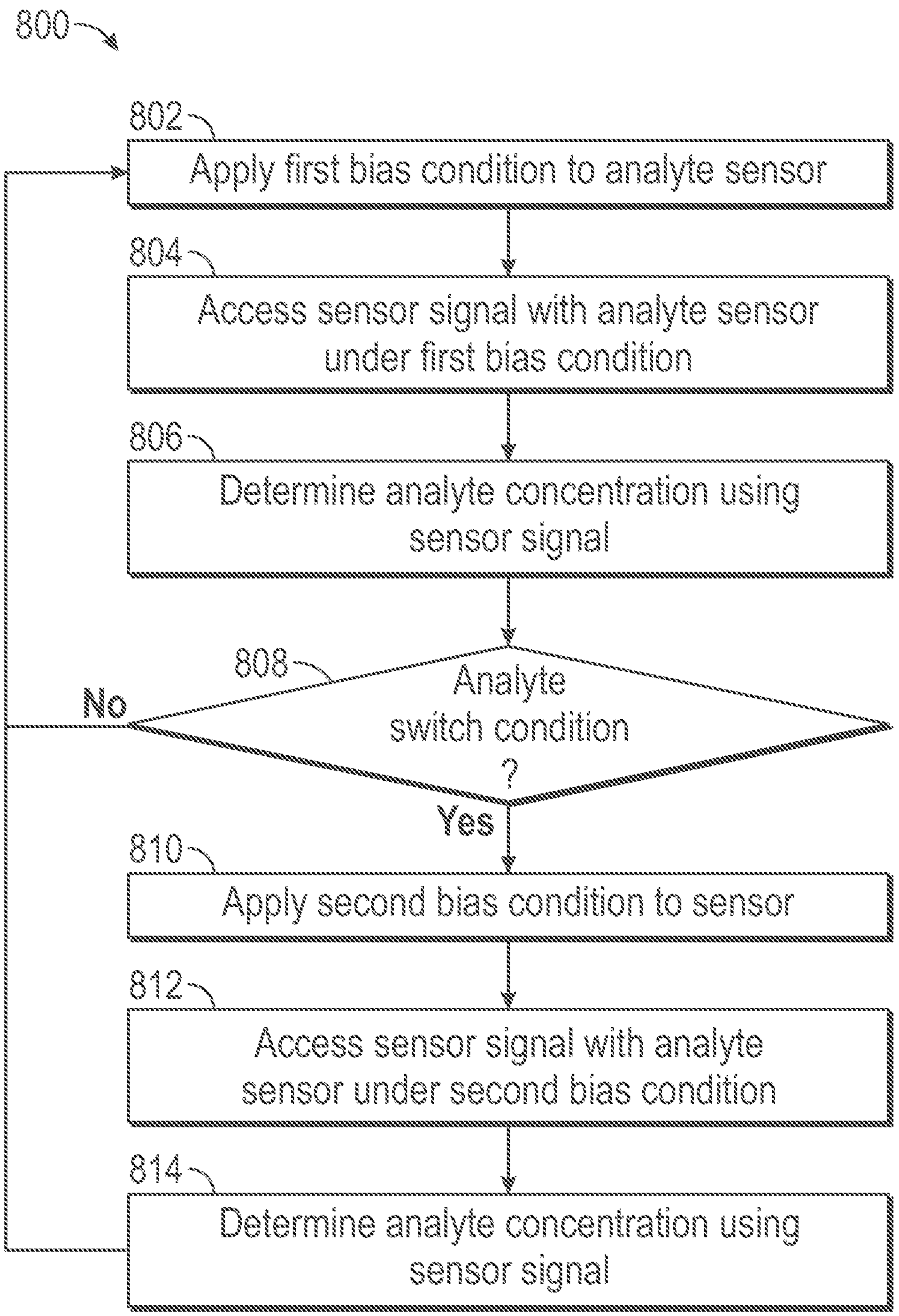
FIG. 8 illustrates an example of a process flow that may be executed in the sensor system of FIG. 5 according to various aspects of the present disclosure.

FIG. 8 illustrates an example of a process flow 800 that may be executed in the sensor system 500 of FIG. 5. At operation 802, the control circuit 502 applies a bias. The indication of the analyte to be measured may be accessed in any suitable manner. In some examples, the host or other user provides an indication of the analyte using one or more computing devices in communication with the sensor system 500 such as, for example, a smart device, a tablet, a smart pen, a computer, a wearable device, a peripheral medical device and/or the like. In other examples, the indication of the analyte to be measured may be generated by the control circuit 502. For example, the control circuit 502 may measure the first and second analyte periodically according to a determined schedule. The control circuit 502 may generate the indication of the analyte based on which analyte is to be measured at a given time.

At operation 804, the control circuit 502 the first signal is accessed under the first bias condition. At operation 806 the control circuit 502 determines the analyte concentration using the accessed signal. At operation 808 the control circuit 502 may determine whether to analyze a second analyte. This may happen automatically or by user input.

If a second analyte is analyzed, a second bias condition can be applied by the control circuit at operation 810. The signal generated from applying the second bias is accessed at operation 812 and the concentration of the analyte is determined at operation 814. Operations 810, 812, and 814 are accessed in a manner similar to those of operations 802, 804, and 806.

Figure 9C:
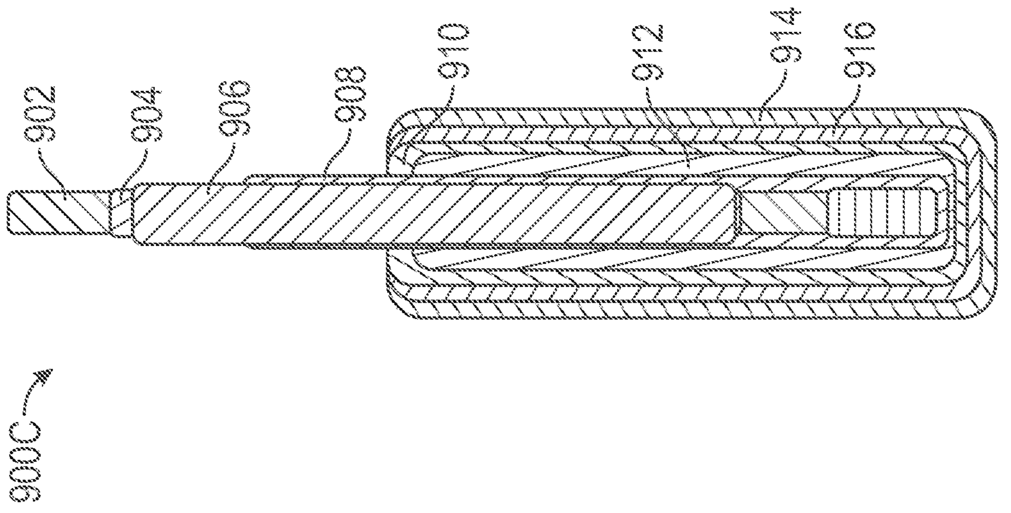
FIG. 9C illustrates an example of another continuous analyte monitoring system including a solid-state electrolyte layer according to various aspects of the present disclosure.
Figure 9B:
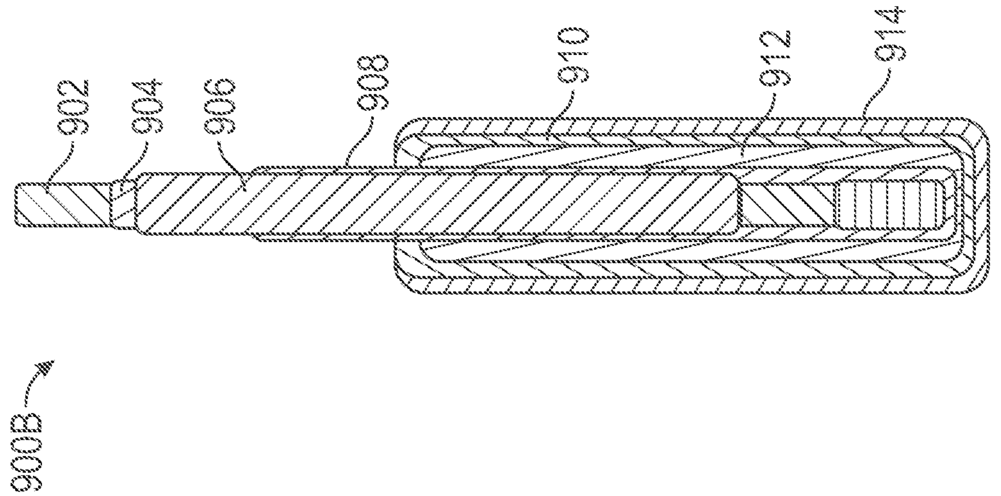
FIG. 9B illustrates an example of another continuous analyte monitoring system including a solid-state electrolyte layer according to various aspects of the present disclosure.
Figure 9A:
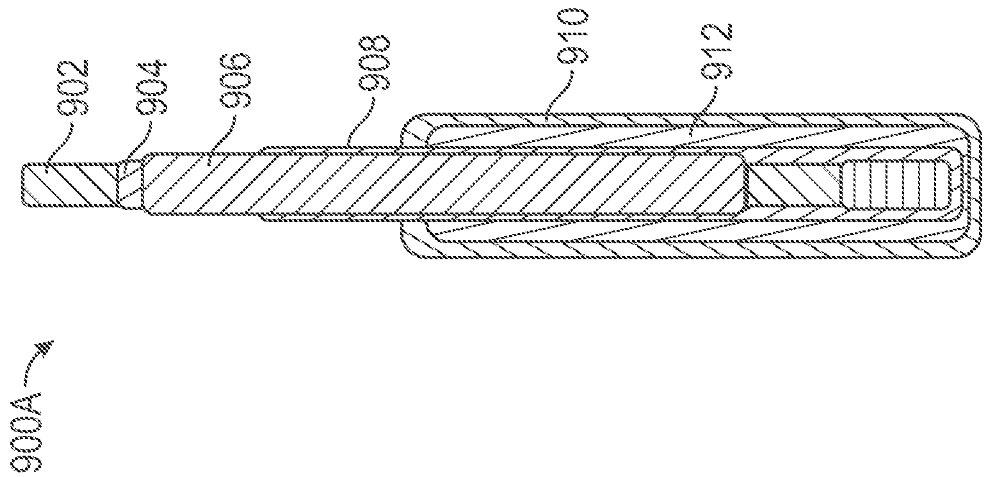
FIG. 9A illustrates an example of a continuous analyte monitoring system including a solid-state electrolyte layer according to various aspects of the present disclosure.

The structure of the analyte sensor 334 can be modified to enhance its ability to measure the concentration of oxygen in the interstitial tissue. This can be accomplished by physically separating the working electrode 438 and the reference electrode. This can further be accomplished by at least partially covering the working electrode 438, reference electrode, or both with a solid-state electrolyte layer. FIGS. 9A-9C are illustrations showing various examples of the analyte sensor 334 including the above-described modifications to enhance its ability to measure the concentration of oxygen in the interstitial tissue. The analyte sensor 334 shown in FIGS. 9A-9C may be formed as a planar sensor having one or more electrodes configured in along a shared central axis with a sensor substrate. In different examples, the analyte sensor 334 may include various cross-sectional geometries, including a circular cross-sectional geometry, an elliptical cross-sectional geometry, a polygonal cross-sectional geometry, or other extruded or deposited (e.g., chemical-vapor deposition, physical-vapor deposition, or the like) cross-sectional geometry FIG. 9A illustrates an example of an analyte sensor 900A. The example analyte sensor 900A includes a working electrode 902, an interference domain 904 and a reference electrode 906. The working electrode 902 is partially covered with an interference domain 904. The working electrode can include any of the materials described herein above with respect to the working electrode 438 The interference domain 904 can include a polymeric material such as such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers. The reference electrode 906 can include any material that is capable of performing an oxidation reaction to complement the reduction reaction at the working electrode 902. For example, the reference electrode 906 can include silver and silver chloride.

In the depicted example, at least a portion of the working electrode 902 and the reference electrode 906 are covered with a solid-state electrolyte layer 908. In one example, solid-state electrolyte layer 908 includes a polyelectrolyte. A polyelectrolyte refers to polymers whose repeating units bear an electrolyte group. For example, polycations and polyanions are polyelectrolytes. Polyelectrolytes dissociate in aqueous solutions, making the polymers charged. Polyelectrolyte properties are thus similar to both electrolytes and polymers and are sometimes called polysalts. Examples of suitable polyelectrolytes for use at the solid-state electrolyte layer 908 are polyacrylic acids, polyethyleneimines, carboxymethylcellulose, polyphosphates, mixtures thereof, and copolymers thereof. Specific examples of repeating units that can be included in polyelectrolytes include acrylamide repeating units, acrylate repeating units include tetrafluoroethylene-perfluoro-3,6-dioxa-4-methyl-7-octane-sulfonic acid copolymer (also categorized under the tradename NAFION).

The solid-state electrolyte layer 908 may be in electrical contact with physiological tissue to complete a circuit between the working electrode 902 and the reference electrode 900 by allowing the passage of ionic current. Additionally, the solid-state electrolyte layer 908 can be permeable to oxygen in gaseous form. Including the solid-state electrolyte layer 908 can also allow the analyte sensor 900A to include a gas permeable diffusion layer 910 atop the working electrode 902. The gas permeable diffusion layer 910 may function to exclude all solvated interfering species and biomolecules. The gas permeable diffusion layer 910, in some examples, is tunable to achieve a range of permeabilities and can be fabricated from other polymeric materials for drug release or the incorporation of oxidase enzyme systems.

An oxidase enzyme system can be present in enzyme layer 912. The enzyme layer can be an optional component, but where present the enzyme layer 912 can include an oxidase. An oxidase refers to an enzyme that catalyzes an oxidation-reduction reaction. Examples of oxidases include cytochrome c oxidase, glucose oxidase, monoamine oxidase, cytochrome P450 oxidase, NADPH oxidase, xanthine oxidase, L-gluconolactone oxidase, laccase, lysyl oxidase, polyphenol oxidase, and sulfhydryl oxidase. If the analyte sensor 800A is being used to measure glucose, the enzyme layer 912 can include glucose oxidase.

FIGS. 9B and 9C illustrate examples of alternate arrangements of an analyte sensor. For example, FIG. 9B shows an analyte sensor 900B. The analyte sensor 900B includes many of the same components as the analyte sensor 900A. However, the analyte sensor 900B additionally includes a resistance layer 914. The resistance layer 914 can at least partially cover the diffusion layer 910.

The resistance layer 914 includes a semi permeable membrane that controls the flux of oxygen and glucose to the underlying enzyme layer 912, rendering oxygen in a non-rate-limiting excess. As a result, the upper limit of linearity of glucose measurement is extended to a much higher value than that which is achieved without the resistance domain. In some examples, the resistance layer 914 exhibits an oxygen-to-glucose permeability ratio of from about 50:1 or less to about 400:1 or more, or about 200:1. As a result, one-dimensional reactant diffusion is adequate to provide excess oxygen at all reasonable glucose and oxygen concentrations found in the subcutaneous matrix.

In some examples, the resistance layer 914 includes a polyurethane membrane with both hydrophilic and hydrophobic regions. The combination of the hydrophobic regions and the hydrophilic regions can be configured to control the diffusion of glucose and oxygen to the enzyme layer 912. Examples of suitable hydrophobic polymer components include polyurethanes, and polyether urethane ureas.

If the resistance layer 914 includes a polyurethane, the flux of oxygen, glucose, or both therethrough can be further controlled by adding a crystallization slowing co-chain extender component to the polyurethane. An example of a crystallization slowing co-chain extender component is 2-methyl-1,3-propanediol, which allows the polyurethane compositions to be dissolved in common solvents and dip coated for use in biosensor membrane applications. The co-chain extender component disposed in the thermoplastic polyurethane compositions can allow for modulation of thermoplastic polyurethane copolymer degree of hard segment domain phase separation and crystallization, morphology, and thus analyte permeability (e.g. decreased $O_2$ permeability/diffusivity) in biosensor membrane applications.

The thermoplastic polyurethanes are generally prepared by combining and reacting a) a polyol component of at least one hydroxyl terminated intermediate such as hydroxyl terminated polyester, polyether, polycarbonate, polycaprolactone, or polysiloxane with b) a polyisocyanate component, c) a primary chain extender component, d) a crystallization slowing co-chain extender component, and optionally a catalyst.

The thermoplastic polyurethanes include a polyol, which includes but are not limited to hydroxyl terminated polyesters, hydroxyl terminated polyethers, hydroxyl terminated polycarbonates, hydroxyl terminated polycaprolactones, hydroxyl terminated polyolefins, and hydroxyl terminated polysiloxanes.

The polyurethanes are derived from an isocyanate. In order to form large linear polyurethane chains, diisocyanates are suitable. Diisocyanates can be aromatic, cycloaliphatic, aliphatic, or combinations thereof having from 2 to 20 carbon atoms. Examples include, but are not limited to diphenylmethane-4,4'diisocyanate (MDI); toluene-2,4-diisocyanate (TDI); toluene-2,6-diisocyanate (TDI); methylene bis (4-cyclohexylisocyanate (H12MDI); 3-isocyanatomethyl-3,5,5-trimethyl-cyclohexyl isocyanate (IPDI); 1,6-hexane diisocyanate (HDI); naphthalene-1,5 diisocyanate (NDI); 1,3 and 1,4-phenylenediisocyanate; xylene diisocyanate (XDI); 1,4-cyclohexyl diisocyanate (CHDI); 1,4-bis (isocyanato methyl) cyclohexane (1,4-H6XDI); 3,3'-Dimethyl-4,4'-biphenyldiisocyanate (TODI); and isomers and mixtures or combinations thereof.

Chain extenders used in the polyurethane formulations described herein. They are also responsible for formation of crystalline hard block domains and consequent hard segment domain phase separation leading to thermoplastic polyurethanes with desirable mechanical properties. Suitable chain extenders are unbranched, unsubstituted, straight chain symmetric alkane diols free of heteroatoms which have a total from about 2 to about 6 carbon atoms. Examples include 1,2-ethanediol, 1,6-hexanediol, 1,3-propanediol, 1,5-propanediol, and preferably 1,4-butanediol. The chain extenders are present in mixture for forming the polyurethane in a range of from about 0.5 wt % to about 20 wt %, about 5 wt % to about 15 wt %, less than, equal to, or greater than about 0.5 wt %, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or about 20 wt %.

The crystallization slowing co-chain extender is generally sterically hindered so that hard segment domain crystalline formation is interrupted or delayed allowing for improved solvent solubility and more copolymer hard segment and soft segment phase mixing.

The crystallization slowing components are short chain or monomeric diols which are branched, substituted, and/or contain heteroatoms (atoms other than carbon). Crystallization slowing components include but are not limited to dipropylene glycol, tripropylene glycol, diethylene glycol, triethylene glycol, cis-trans-isomers of cyclohexyl dimethylol, neopentyl glycol and substituted alkane diols such as 2-methyl-1,3-propanediol, 3-methyl-1,5-pentanediol, 1,3-butane diol, and 2-methyl-2,4-pentane diol. Any branched or substituted alkane diols having from about 2 up to about 12 carbon atoms in the main chain can be utilized. Please see FIGS. 4-6 for select chain extender chemical structures.

FIG. 9C illustrates an example of analyte sensor 900C including a second enzyme layer 916. The analyte sensor 900C includes many of the same components as the analyte sensors 900A and 900B, and additionally includes the second enzyme layer 916. The second enzyme layer 916 can be at least partially covered with the resistance layer 914. The second enzyme layer can include any of the enzymes described herein above with respect to the enzyme layer 912. In some examples the second enzyme layer 916 can function to catalyze a reaction where an analyte of interest is reacted to a form product that can be further reacted upon contact with the enzyme layer 912. This can increase the accuracy of the analyte sensor 900C. Alternatively, the second enzyme layer 916 can function to catalyze the reaction of an interferant to a product that will not be catalyzed upon contact with the enzyme layer 912 and cause a false signal to be generated by the analyte sensor 900C.

Any of the continuous analyte sensors discussed herein including the analyte sensors 900A-900C can be calibrated ex vivo. The calibration is discussed with reference to FIG. 11, which illustrates an example of a calibration process 1101. Calibration can include exposing any of the analyte sensors 900A-900C to a first known analyte concentration at operation 1102. For example, a portion of any of the analyte sensors 900A-900C can be exposed to a liquid solution having an analyte of interest dissolved therein. For example, the liquid solution can have a known dissolved oxygen content or a known dissolved glucose content. Following exposure, a first sensor signal is accessed as generated by any of the analyte sensors 900A-900C at operation 1104. Thereafter, any of the analyte sensors 900A-900C is exposed to a second known analyte concentration that can be the same or different than the first known analyte concentration at operation 1108. Similar to the first known analyte concentration, the second known analyte concentration can have a known dissolved oxygen content or a known dissolved glucose content. Following exposure, a second sensor signal is accessed as generated by any of the analyte sensors 900A-900C at operation 1110. This process can be repeated any number of times to generate any plural number of signals.

After all signals are accessed, a calibration parameter is determined at operation 1113. The calibration parameter may include a linear relationship between an amount of signal produced by the analyte sensor 900A-900C and the analyte concentration. The calibration parameter can include the sensitivity in which the sensitivity describes an analyte concentration per unit of sensor signal. In some aspects a calibration may be defined by solving for the equation $y=mx+b$, the value of b represents the baseline of the signal. In certain aspects, the value of b (i.e., the baseline) can be zero or about zero. This can be the result of a baseline-subtracting electrode or low bias potential settings, for example. As a result, for these aspects, calibration can be defined by solving for the equation $y=mx$. Once the calibration parameter is determined any of the sensors 900A-900C can be deployed in vivo. Upon deployment at least a third senor signal is accessed. The concentration of the analyte of interest is then determined using the calibration parameter.

The analyte sensors 334, 900A, 900B, and 900C have been depicted as having a coaxial construction with respect to the working electrode 438 or 902 and reference electrode 906, and other components. As mentioned herein, components such as the working electrode 438 or 902 reference electrode 906, and other components including a core on which the one or more electrodes are positioned can be planar. The planar structure can conform to a generally, planar square profile, planar triangular profile, planar rectangular profile, or any higher order planar polygonal profile.

Planar structures are shown in FIGS. 10A-10G. Planar analyte sensors can be readily manufactured and create reproducible results. Planar analyte sensors can be configured to monitor, including to continuously monitor, at least one analyte, and, in some examples, two or more analytes. The planar analyte sensors can be configured differently and may be described based on the geometry of their electrode layouts. The sensor types can include single-sided or double-sided layouts. In single-sided layouts, the electrodes can be conductive traces and can be in a coplanar arrangement, a stacked arrangement, or a staggered arrangement. In double-sided layouts the electrodes can be in a coplanar arrangement, a stacked arrangement, or a staggered arrangement, as well as arrangements where connector pads are on a single side of the sensor, or arrangements where connector pads are on both sides of the sensor.

FIGS. 10A-10G illustrate a single sided coplanar analyte sensor assembly 1000 in an example. The sensor assembly can have a first end 1012 and a second end 1014. The sensor assembly 1000 can include substrate 1010, conductive traces 1021, connector pads 1022, working electrode 1024, counter electrode 1026, insulator 1030, and reference electrode 1040. In sensor assembly 1000, a single-sided planar configuration is used. In the sensor assembly 1000, a three-electrode sensor is shown, with a working electrode (WE) 1024, a counter electrode (CE) 1026 and a reference electrode (RE) 1040. In sensor assembly 1000, the electrodes are coplanar.

Figure 10D:
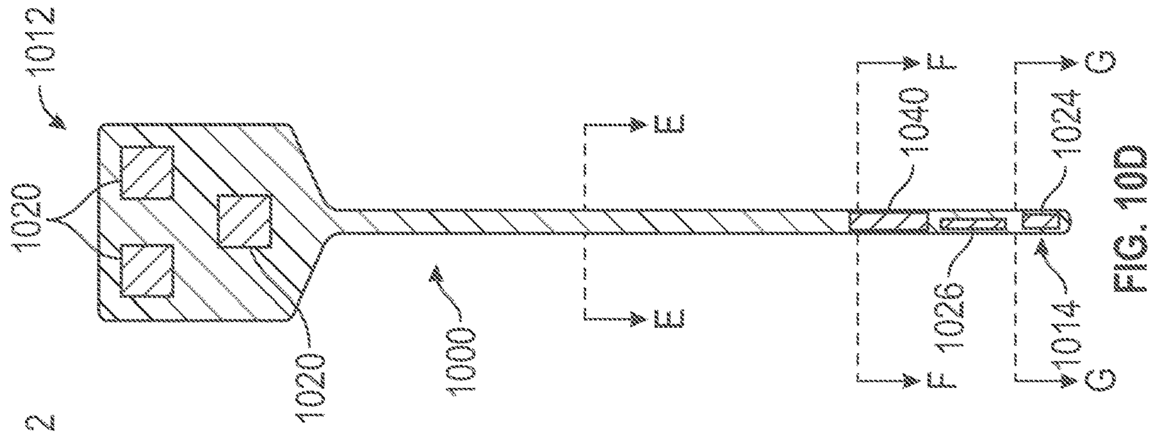
FIGS. 10A-10G illustrate an example of a single sided coplanar analyte sensor according to various aspects of the present disclosure.
Figure 10C:
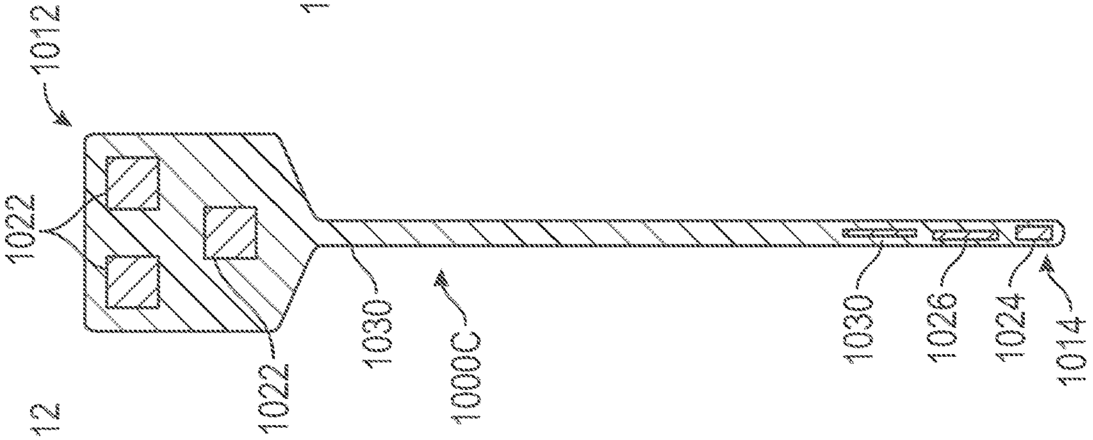
Figure 10B:
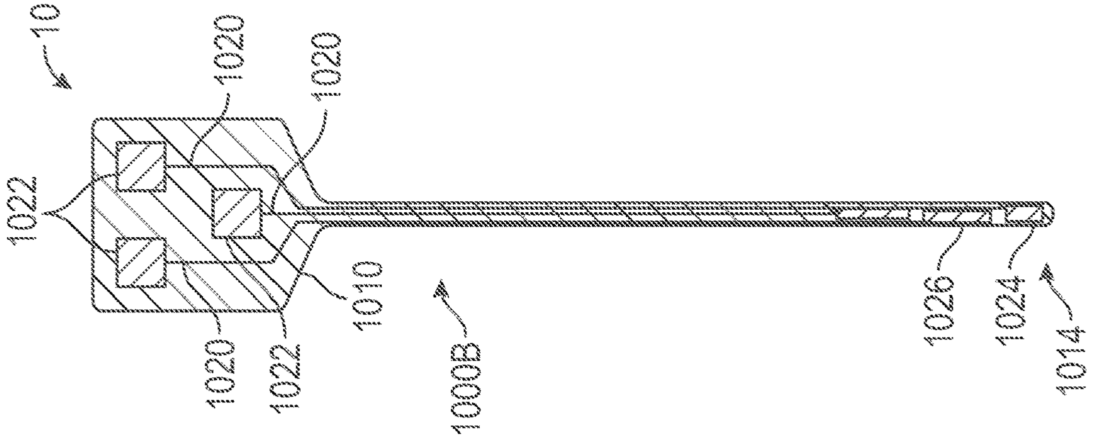

FIGS. 10A to 10D depict top-down schematic views of the sensor assembly 1000 being produced. FIGS. 10E to 10G depict cross-sectional schematic views of the sensor assembly 1000 at varying points along the length of the sensor assembly 1000.

The sensor assembly 1000 can extend between the first end 1012 and the second end 1014 and be substantially planar along its length. The first end 1012 can be, for example, a connection end, such as for allowing electrical connection of the sensor assembly 1000 to a reader, computer, or other component for interpretation of signals detected with the sensor assembly 1000. The first end 1012 can host one or more connection pads 1022.

The second end 1014 can be, for example, a sensing end, for connection with or implantation in a patient, such as for detecting glucose or other analytes. The second end 1014 can host the electrodes 1024, 1026, and 1040. The second end 1014 can be the implantable portion of the sensor assembly 1000. The first end 1012 of the sensor that has the connector pads 1022 can be the proximal end of the sensor assembly 1000. The second end 1014 with the implantable portion of the sensor that contains the sensing electrodes can be the distal end of the sensor assembly 1000.

Figure 10A:
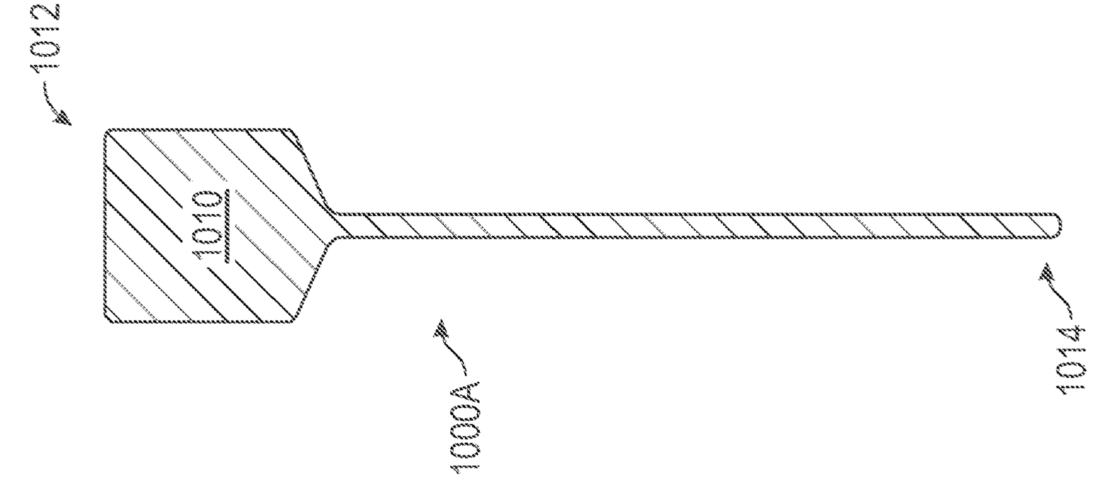
Figure 10E:
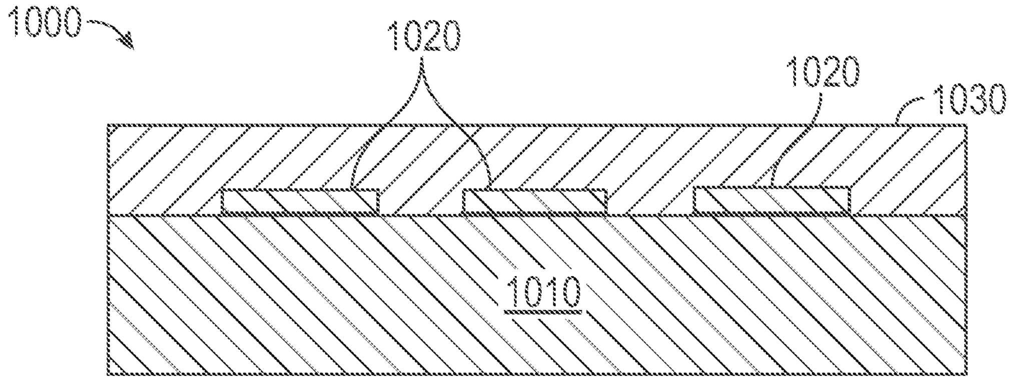
Figure 10F:
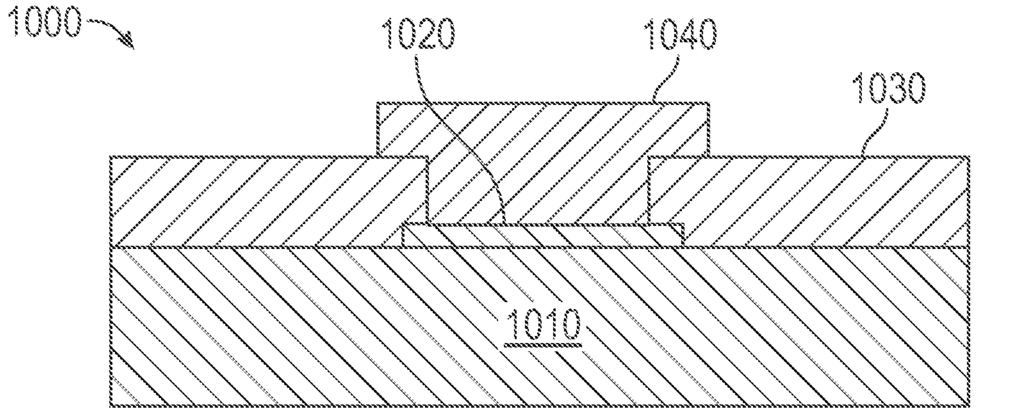
Figure 10G:
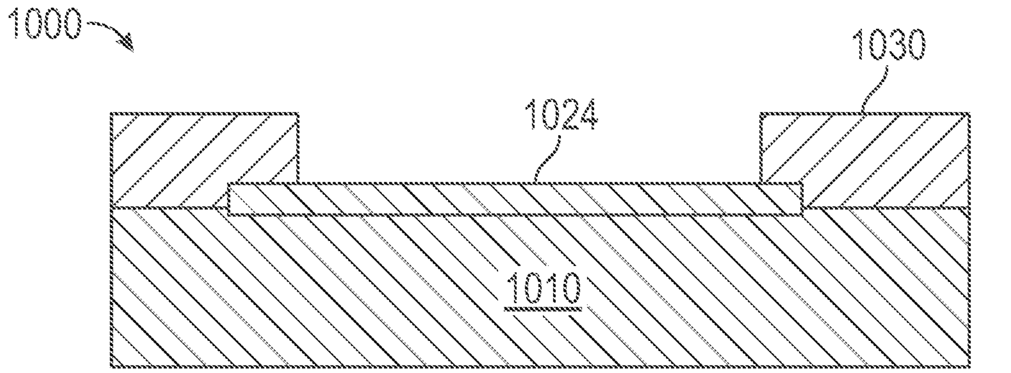

Shown in FIG. 10A, the substrate 1010 can extend between the first end 1012 and the second end 1014. The substrate 1010 can be a relatively planar material, for example, the substrate 1010 can be a thin flexible layer for hosting the other components. In some cases, the substrate 1010 can be a polymeric film, such as liquid crystal polymer (LCP), polyimide (PI), polyethylene terephthalate (PET), combinations thereof, or similar polymeric films. The substrate 1010 can have a thickness of about 25 to about 450 μm, such as a thickness of about 75 to 100 μm. In some examples, a substrate thickness of about 40 μm to about 80 μm may be used.

The conductive traces 1021, connector pads 1022, working electrode 1024, and counter electrode 1026 can be made from a conductive layer built on the substrate. The connector pads 1022 can be situated on or at the first end 1012 of the assembly 1000 and allow for electrical connection of the sensor assembly 1000. The working electrode 1024 and the counter electrode 1026 can be sensing electrodes exposed at the second end 1014 of the assembly 1000 for implantation and sensing of an analyte in a patient environment. The conductive traces 1021 can connected the electrodes 1024, 1026, to the connector pads 1022.

Shown in FIG. 4B, the conductive layer can be built up on the substrate 1010 with the conductive traces 1021, connector pads 1022, working electrode 1024, and counter electrode 1026 in a single plane or layer. The conductive layer can, for example, be made of a sputtered metal, such as titanium/gold/platinum or platinum/gold/platinum sputtered metal layers. In this case, relevant sensing surfaces such as at the working electrode 1024 can have exposed platinum for electrical connection and sensing. The reference electrode 1040 can be deposited on a base metal pad, and can be connected through additional conductive traces.

In some examples, the conductive layer is formed from a single conductor, such as gold or platinum. In other examples, the conductive layer or can be formed from more than one material, such as a thin palladium layer that is covered with gold and platinum. The composition, geometry, and exposed conductor surfaces can depend on the manufacturing method, desired mechanical properties, and requirements of the sensing chemistry. For example, the base conductive material can be formed by a less expensive material, such as silver, which is covered in strategic locations by platinum for the active sensing surfaces. In some cases, gold can be plated as the base conductor, which is can be covered with platinum in order to provide both mechanical robustness and an active sensing surface for sensing hydrogen peroxide.

The conductive layer, including the working electrode 1024, counter electrode 1026, connector pads 1022, and conductive traces 1021, can be formed by a variety of techniques, such as plating, sputtering, or printing. To form the structure of patterning of the conductive layers, standard photolithographic techniques, laser ablation, or printing (e.g., inkjet or screen printing) can be used.

Although certain electrode designations are shown in the supporting document, it should be understood that the size, shape, and electrode identity can be changed depending on a specific use case, such as a particular analyte to be determined. The general size and shape of the sensor is 3 to 4 mm wide at the proximal end (connector end) and 300-500 μm wide in the narrow implantable distal end. The overall length of the sensor is dependent on the requirements of the wearable/inserter but are generally between 15 and 25 mm.

Shown in FIG. 10C, the insulator 1030 can be layered on top of the conductive layer as desired. Insulating materials can be referred to as "solder mask," "dielectric," or "insulator." These materials can be used to protect the conductive traces from exposure to the sample matrix and environment, as well as improve the accuracy and reliability of measurements by defining the sensing electrode area. An opening 1031 can be made for later deposition of the reference electrode 1040.

Here, the insulator 1030 can be made of an electrically insulating material deposited on top of the conductive layer to protect the conductive traces 1021 and define the openings for the connector pads 1022, and the electrodes 1024, 1026, in addition to an opening 1031 for the reference electrode 1040. The insulator 1030 can be, for example, a thin layer of solder mask.

Shown in FIG. 10D, the reference electrode 1040 material can be deposited over the designated reference electrode opening in the insulator 1030. The reference electrode 1040 material can be, for example, a silver/silver chloride formulation. It can be deposited on the designated sensing electrode pad. This reference electrode material can be deposited by a printing technique, such as screen printing, or by discrete dispense, such as a jet-valve dispenser.

FIGS. 10E to 10G depict cross-section of the assembly 1000 at varying points along the body of the assembly. FIG. 10E shows a cross-section at line E-E of FIG. 10D, in a central portion of the assembly 1000. At this part of the assembly 1000, the conductive traces 1021 can be seen between the insulator 1030 and the substrate 1010. FIG. 10F shows a cross-section at line F-F of FIG. 10D, near the second end 1014 of the assembly 1000. At this part of the assembly 1000, the reference electrode 1040 can be seen on top of the conductive traces 1021. FIG. 10G depicts a cross-section at line G-G of the assembly, near the second end 1014. Here, the working electrode 1024 can be seen. The assembly 1000 is a single sided, coplanar arrangement for the electrodes 1024, 1026, 1040.

Figure 11:
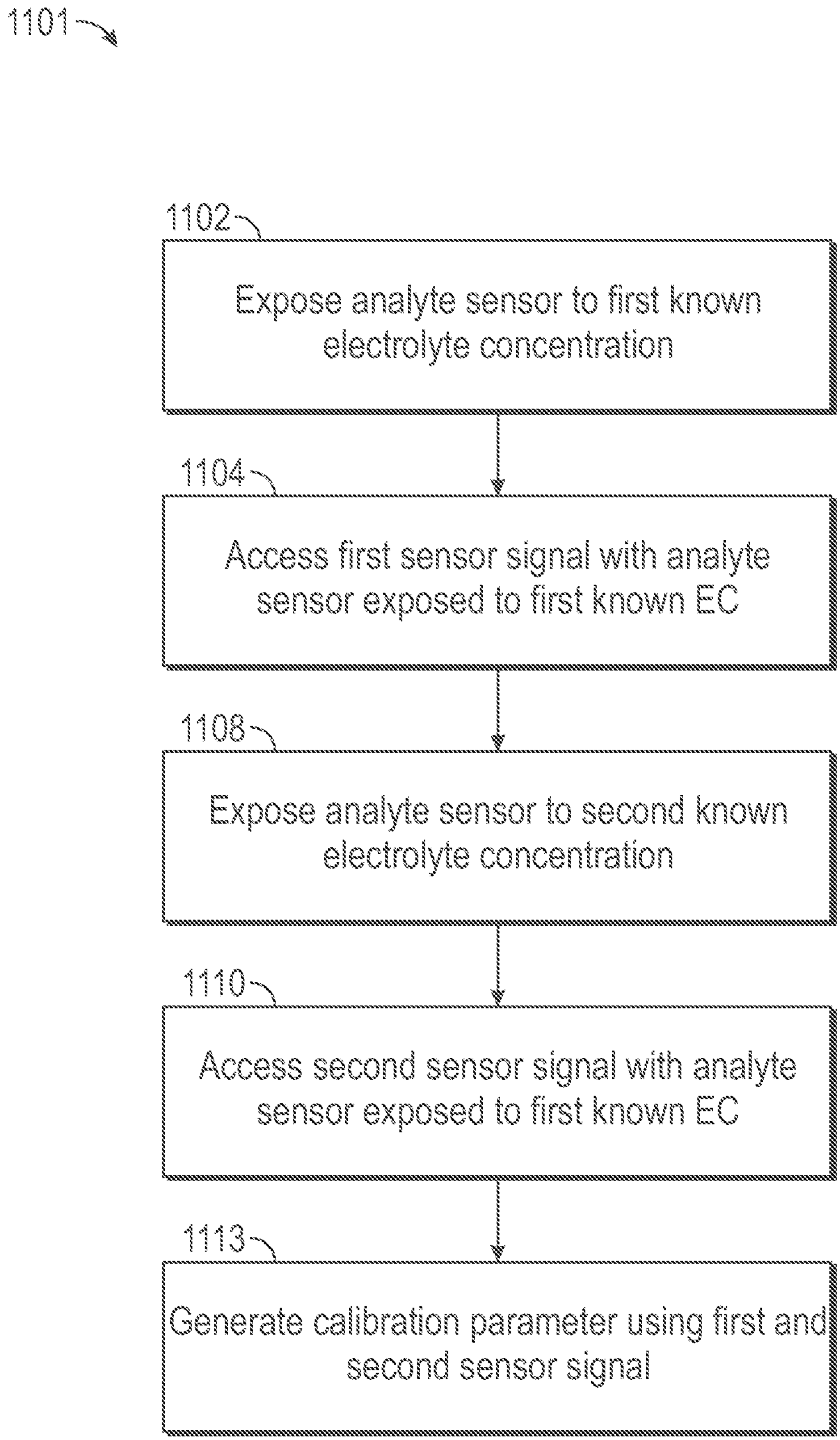
FIG. 11 illustrates an example of a calibration process of a continuous analyte monitoring system according to various aspects of the present disclosure.

Additionally, in some examples, some components of the analyte sensors 334, 900A, 900B, and 900C can be completely separated from each other. For example, FIG. 11 illustrates an example of an analyte sensor system 1100 having a reference electrode 112 configured to be in contact the skin of a host.

The analyte sensor system 1100 can be beneficial in that it may reduce the risk of silver migrating from the reference electrode 1112 to the working electrode 1106. For example, in arrangements where the reference electrode is positioned subcutaneously, silver ions may generate and can migrate to the working electrode 1106 where they are reduced and deposited. This prevents current from flowing between the electrodes, thus making it impossible to determine analyte concentration.

Figure 12:
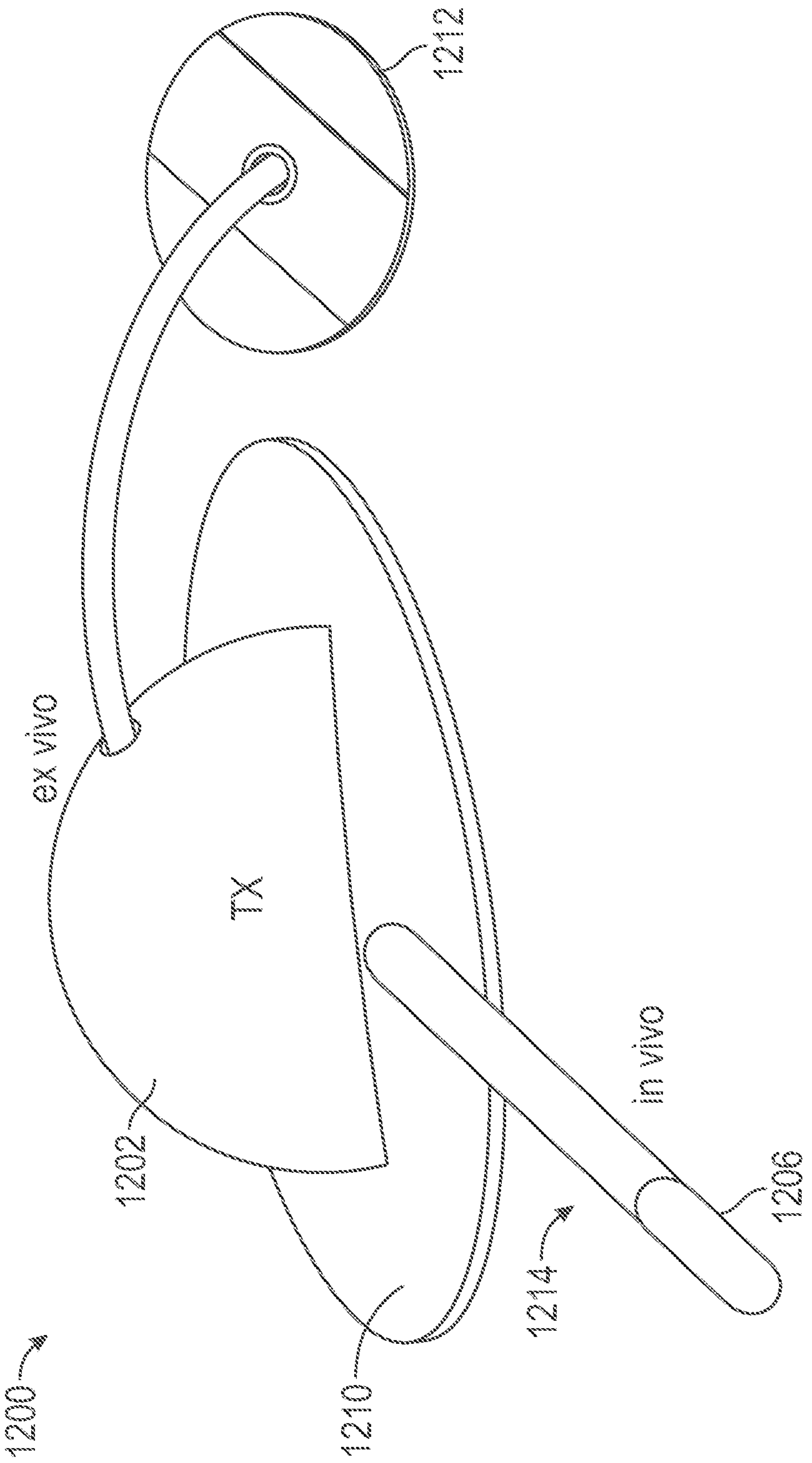
FIG. 12 illustrates an example of another continuous analyte monitoring system according to various aspects of the present disclosure.

The arrangement shown in FIG. 12 includes the reference electrode 1212 that is configured to be placed in contact with the external surface of the skin of the host. This may, in some examples, reduce the risk, of silver migration that can result in short circuits. Thus, the physical separation attributed to the host's skin provides physical separation of the electrodes and prevents migration of the silver ions to the working electrode.

As shown in FIG. 12, analyte sensor 1200 includes a mounting unit 1202, which includes many of the same components as the mounting unit 314 described herein above. The mounting unit 1202 can be adhered to the external surface of a host's skin (ex vivo) by an adhesive patch 1210. An implantable probe 1204 includes a working electrode 1206, which may be arranged in a manner similar to the working electrodes 438 and/or 902 described herein. The reference electrode 1212 is adapted to adhere to the external surface of a host's skin (ex vivo). The reference electrode 1212 can be formed of any metal suitable to conduct the oxidation reactions described herein. In some examples, the metal of the reference electrode can be at least partially surrounded by an electrically conductive gel.

The interference domain 1214 can perform a similar role in the analyte sensors 900A-900C. Another potential benefit of locating the reference electrode 1212 ex-vivo, for example, on the external surface of a host's skin is that the footprint of an in-vivo portion of the analyte sensor 1200, inside the host, is reduced because less hardware needs to be implanted therein. By contrast in FIGS. 9A-9C, all shown components are adapted to be disposed in vivo. This can reduce the complexity in analyte sensor 1200's design and potentially increase the host's comfort. In some alterative examples, at least a portion of the reference electrode 1212 may be inserted into the host's skin, but it may not be inserted to the same degree that the working electrode 1206 is inserted. This again can decrease the footprint of the analyte sensor 1200 and potentially increase a host's comfort.

The sensors 900A-900C and 1200 are discussed primarily in the context of being used to detect interstitial oxygen concentrations. However, depending on the enzyme located in their respective enzyme layers, any of the sensors 900A-900C and 1200 can be used to detect interstitial glucose levels. It has been found, however, that at least the solid-state electrolyte layer 908 has a particularly beneficial, and unexpected, effect in measuring interstitial oxygen levels.

Figure 13:
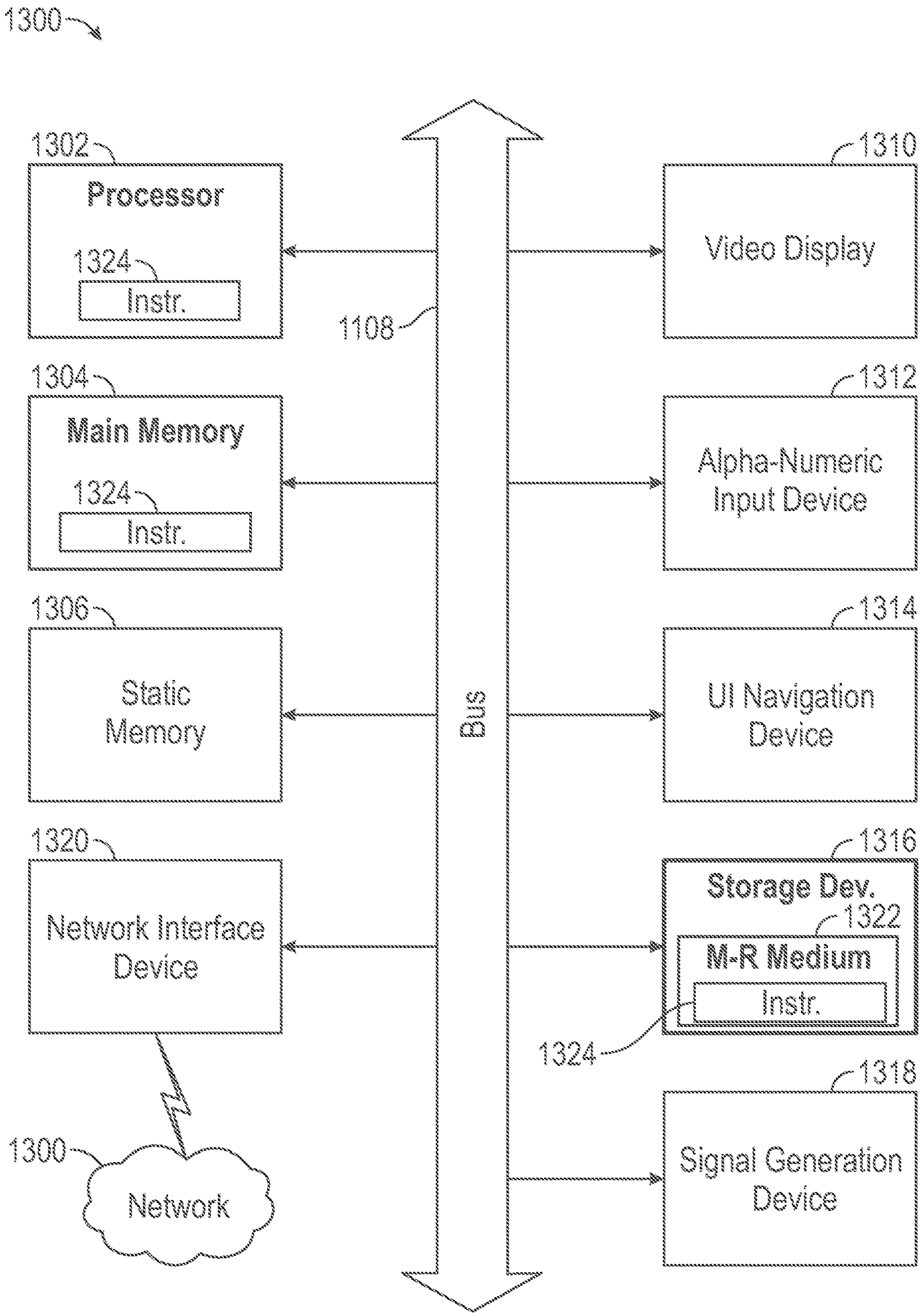
FIG. 13 illustrates an example of a computing device hardware architecture according to various aspects of the present disclosure.

FIG. 13 illustrates an example of a hardware architecture 1300, within which a set or sequence of instructions can be executed to cause a machine to perform examples of any one of the methodologies discussed herein. The hardware architecture 1300 can describe various computing devices including, such as those described herein, including a hand-held smart device (e.g., smart device), tablet, smart pen (e.g., insulin delivery pen with processing and communication capability), computer, a wearable device such as a watch, or peripheral medical device.

The architecture 1300 may operate as a standalone device or may be connected (e.g., networked) to other machines. In a networked deployment, the architecture 1300 may operate in the capacity of either a server or a client machine in server-client network environments, or it may act as a peer machine in peer-to-peer (or distributed) network environments. The architecture 1300 can be implemented in a personal computer (PC), a tablet PC, a hybrid tablet, a set-top box (STB), a personal digital assistant (PDA), a mobile telephone, a web appliance, a network router, a network switch, a network bridge, wearable technology such as a watch, hat, or other piece of jewelry, item of clothing, accessory, or Internet-of-things (IoT) device, or any machine capable of executing instructions (sequential or otherwise) that specify operations to be taken by that machine.

The example architecture 1300 includes a processor unit 1302 comprising at least one processor (e.g., a central processing unit (CPU), a graphics processing unit (GPU), or both, processor cores, compute nodes). The architecture 1300 may further comprise a main memory 1304 and a static memory 1306, which communicate with each other via a link 1308 (e.g., bus). The architecture 1300 can further include a video display unit 1310, an input device 1312 (e.g., a keyboard), and a UI navigation device 1314 (e.g., a mouse). In some examples, the video display unit 1310, input device 1312, and UI navigation device 1314 are incorporated into a touchscreen display. The architecture 1300 may additionally include a storage device 1316 (e.g., a drive unit), a signal generation device 1318 (e.g., a speaker), a network interface device 1320, and one or more sensors (not shown), such as a Global Positioning System (GPS) sensor, compass, accelerometer, or other sensor.

In some examples, the processor unit 1302 or another suitable hardware component may support a hardware interrupt. In response to a hardware interrupt, the processor unit 1302 may pause its processing and execute an ISR, for example, as described herein.

The storage device 1316 includes a machine-readable medium 1322 on which is stored one or more sets of data structures and instructions 1324 (e.g., software) embodying or used by any one or more of the methodologies or functions described herein. The instructions 1324 can also reside, completely or at least partially, within the main memory 1304, within the static memory 1306, and/or within the processor unit 1302 during execution thereof by the architecture 1300, with the main memory 1304, the static memory 1306, and the processor unit 1302 also constituting machine-readable media.

Executable Instructions and Machine-Storage Medium

The various memories (i.e., 1304, 1306, and/or memory of the processor unit(s) 1302) and/or storage device 1316 may store one or more sets of instructions and data structures (e.g., instructions) 1324 embodying or used by any one or more of the methodologies or functions described herein. These instructions, when executed by processor unit(s) 1302 cause various operations to implement the disclosed examples.

As used herein, the terms "machine-storage medium," "device-storage medium," "computer-storage medium" (referred to collectively as "machine-storage medium 1322") mean the same thing and may be used interchangeably in this disclosure. The terms refer to a single or multiple storage devices and/or media (e.g., a centralized or distributed database, and/or associated caches and servers) that store executable instructions and/or data, as well as cloud-based storage systems or storage networks that include multiple storage apparatus or devices. The terms shall accordingly be taken to include, but not be limited to, solid-state memories, and optical and magnetic media, including memory internal or external to processors. Specific examples of a machine-readable medium 1322 include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks.

Computer-Readable Medium

The instructions 1324 can further be transmitted or received over a communications network 1326 using a transmission medium via the network interface device 1320 using any one of a number of well-known transfer protocols (e.g., HTTP). Examples of communication networks include a LAN, a WAN, the Internet, mobile telephone networks, plain old telephone service (POTS) networks, and wireless data networks (e.g., Wi-Fi, 3G, 4G LTE/LTE-A, 5G or WiMAX networks). The term "transmission medium" shall be taken to include any intangible medium that is capable of storing, encoding, or carrying instructions for execution by the machine, and includes digital or analog communications signals or other intangible media to facilitate communication of such software.

EXAMPLES

The benefit of the third bias operation discussed herein above with respect to FIGS. 15 and 16 was evaluated by running a complete sequence that included an odd cycle (first bias condition), in which the waveform was 57 min glucose mode at 0.6 V+3 min $O_2$ mode (second bias condition) at −0.2 V, followed by the even cycle with the waveform 30 s overpotential step (the third bias condition) at 0.8 V+56.5 min.

Figure 17A:
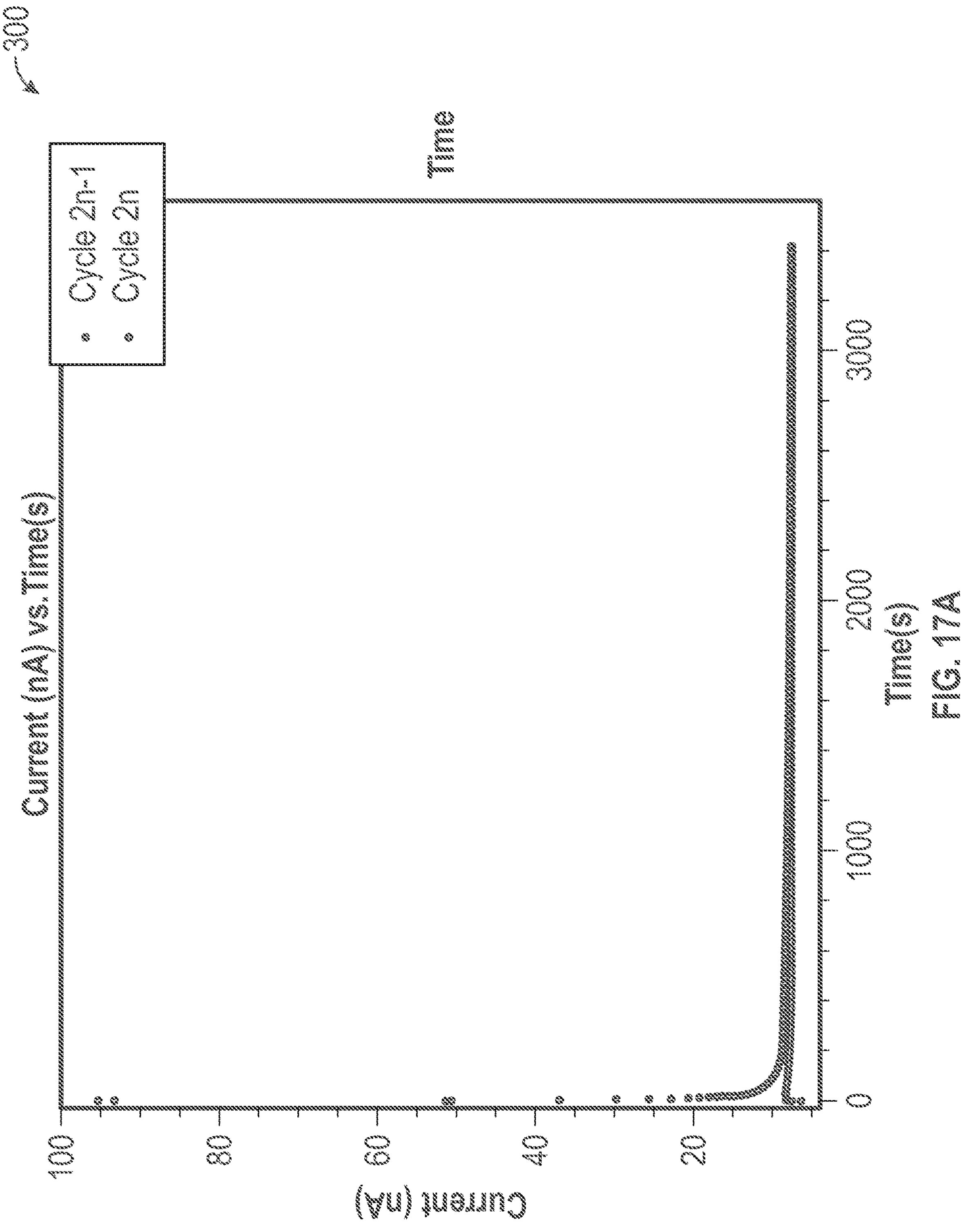
FIG. 17A is a graph showing glucose current measurements in odd cycles (without overpotential step) compared with those in even cycles (with overpotential step) according to various aspects of the present disclosure.
Figure 17B:
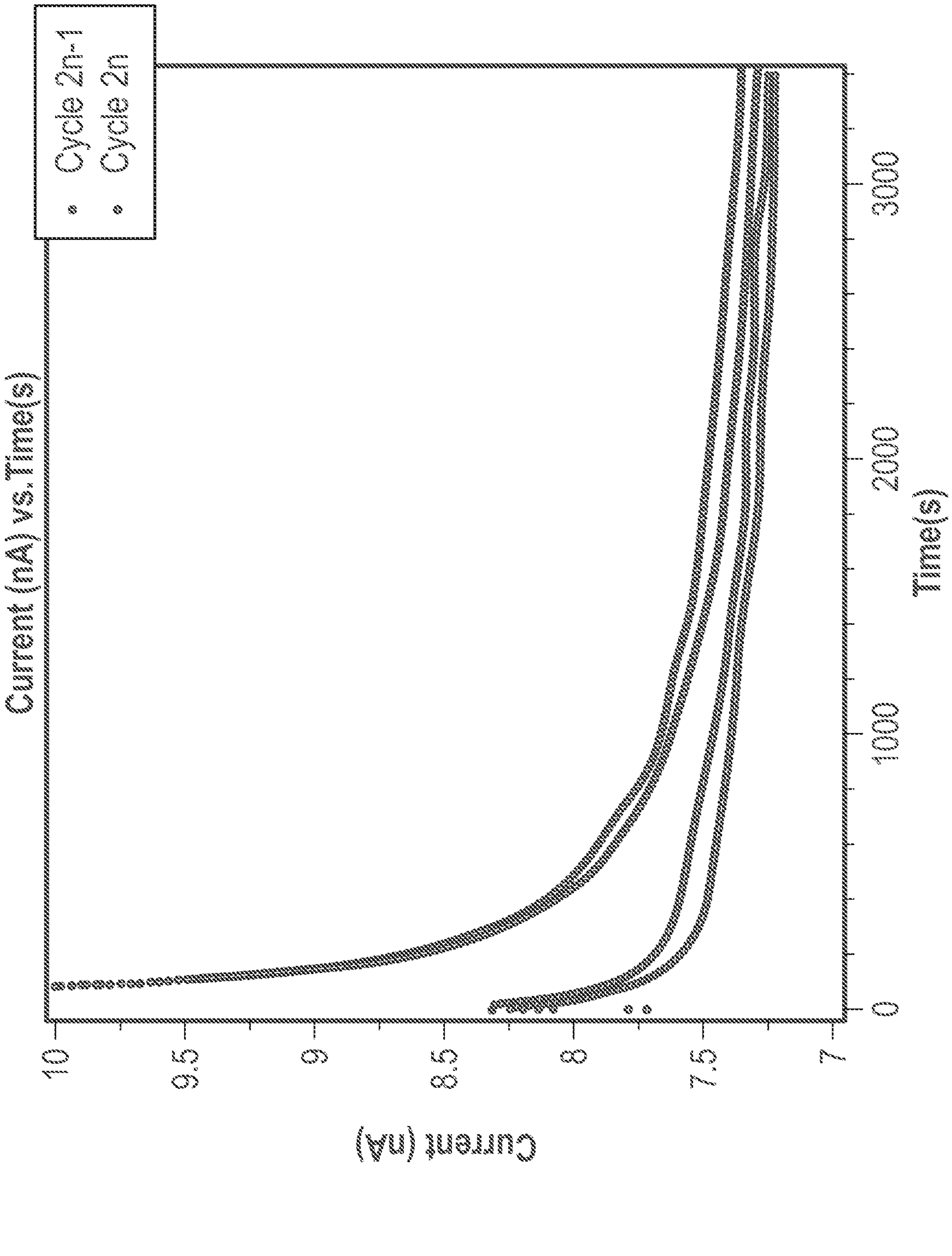
FIG. 17B is a zoomed-in portion of the graph of FIG. 16A according to various aspects of the present disclosure.

For all the tested sensors (n=8), the even cycles, which contains overpotential step (30 s at 0.8 V), demonstrated faster stabilization of glucose signal compared with the neighboring odd cycles within testing window (48 h). There was no significant impact on $O_2$ measurement. The testing buffer is 250 mg/dL glucose in sensor drifting buffer at 36° C. under 1.8 ppm $O_2$. FIG. 17A shows Glucose signal measurements in odd cycles (without overpotential step) compared with those in even cycles (with overpotential step). FIG. 17B is a zoom in plot of a portion of FIG. 17A.

To quantify the stabilization time, $1^{st}$ derivative of glucose current vs time was plotted for the odd and even cycle, wherein $$1^{st}\text{ derivative} = \frac{\Delta y}{\Delta x}(\Delta y = \text{ raw current difference within 30 } s, \Delta x = 30\ s).$$

The stabilization time of glucose current from cycle 13 to cycle 14 was reduced from 450 s to 200 s, where the stabilization is defined as the $1^{st}$ derivation within 2 pA.

To validate the benefit of the overpotential step, the same waveform was under two more different glucose concentrations (40 mg/dL and 400 mg/dL). Similar to the first run, the cycle that contains overpotential step showed significantly reduced the stabilization time for glucose current within the testing window.

To further validate the benefit of the overpotential step, two more different waveforms were tested under 250 mg/dL glucose over 14 days. For each waveform, sensors were split into three groups, the overpotential group (with overpotential step); the dual mode group (with flipping bias); and the control group (glucose mode only). The overpotential group demonstrated faster stabilization of glucose current compared with the dual sensing group. Moreover, the overpotential group and dual mode group doesn't significantly increase the spread of glucose sensitivity.

It was determined that applying an overpotential step between flipping bias for dual sensing can be used to accelerate the rate of reaching electrochemical equilibrium and stabilization of the glucose current. This technique is feasible at different glucose concentrations (e.g. 40 mg/dL, 250 mg/dL and 400 mg/dL), as well as different waveforms (10 min, 15 min and 1 h).

Before reaching electrochemical equilibrium and stabilization of the analyte current, transient currents can be used to predict the estimated analyte concentration level. For example, the transient glucose current can be used to predict the estimated glucose concentration level prior to reaching steady state. In one application, the average of current over a certain period (5 seconds, for example) during the transient period is used to extrapolate the current at its steady state via a pre-defined mathematical equation. Alternatively, a mathematical or physical fitting (via Cottrell equation, for example) can be applied to extract parameters that can generate a prediction of current at a later stage.

Figure 18A:
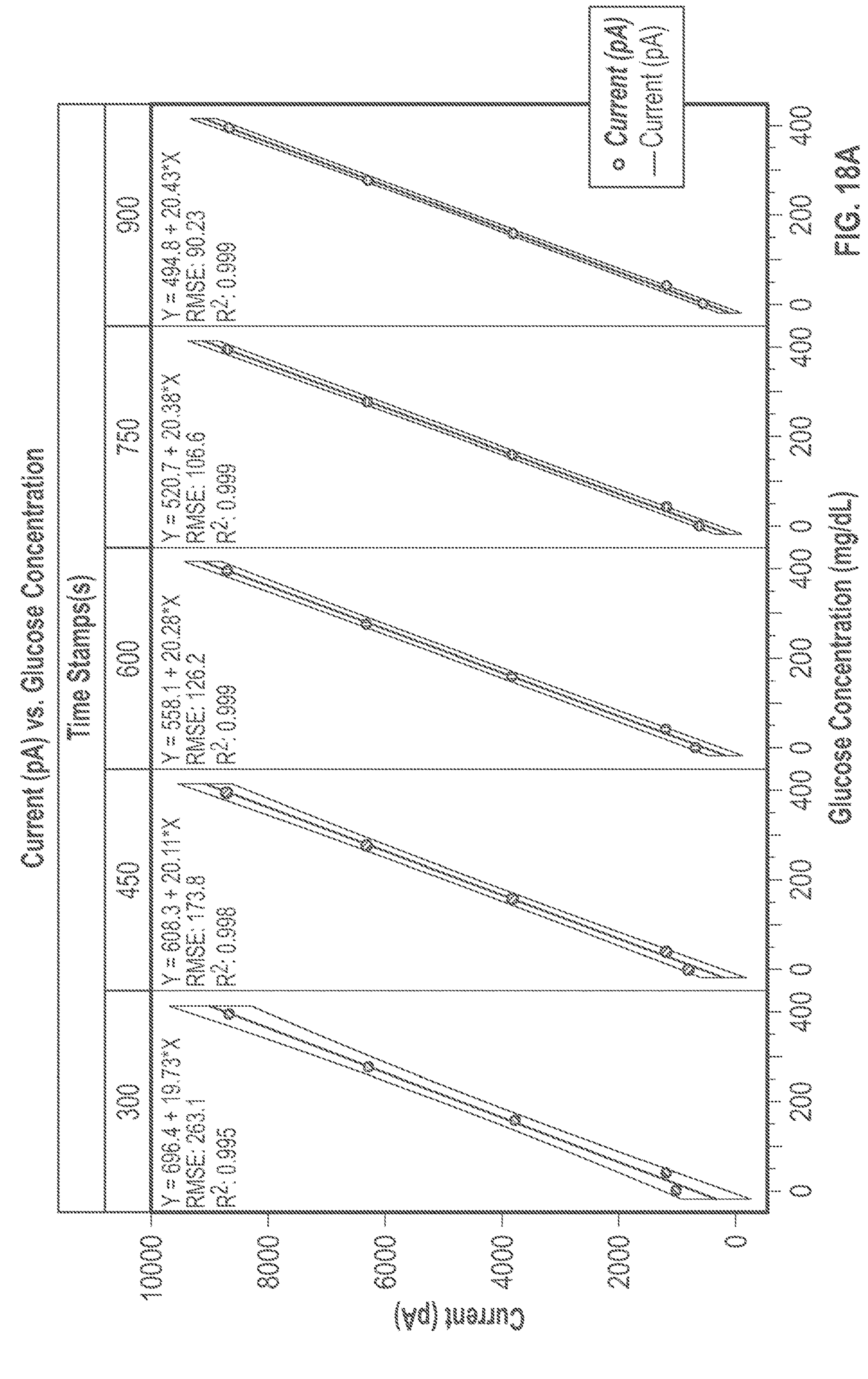
Figure 18B:
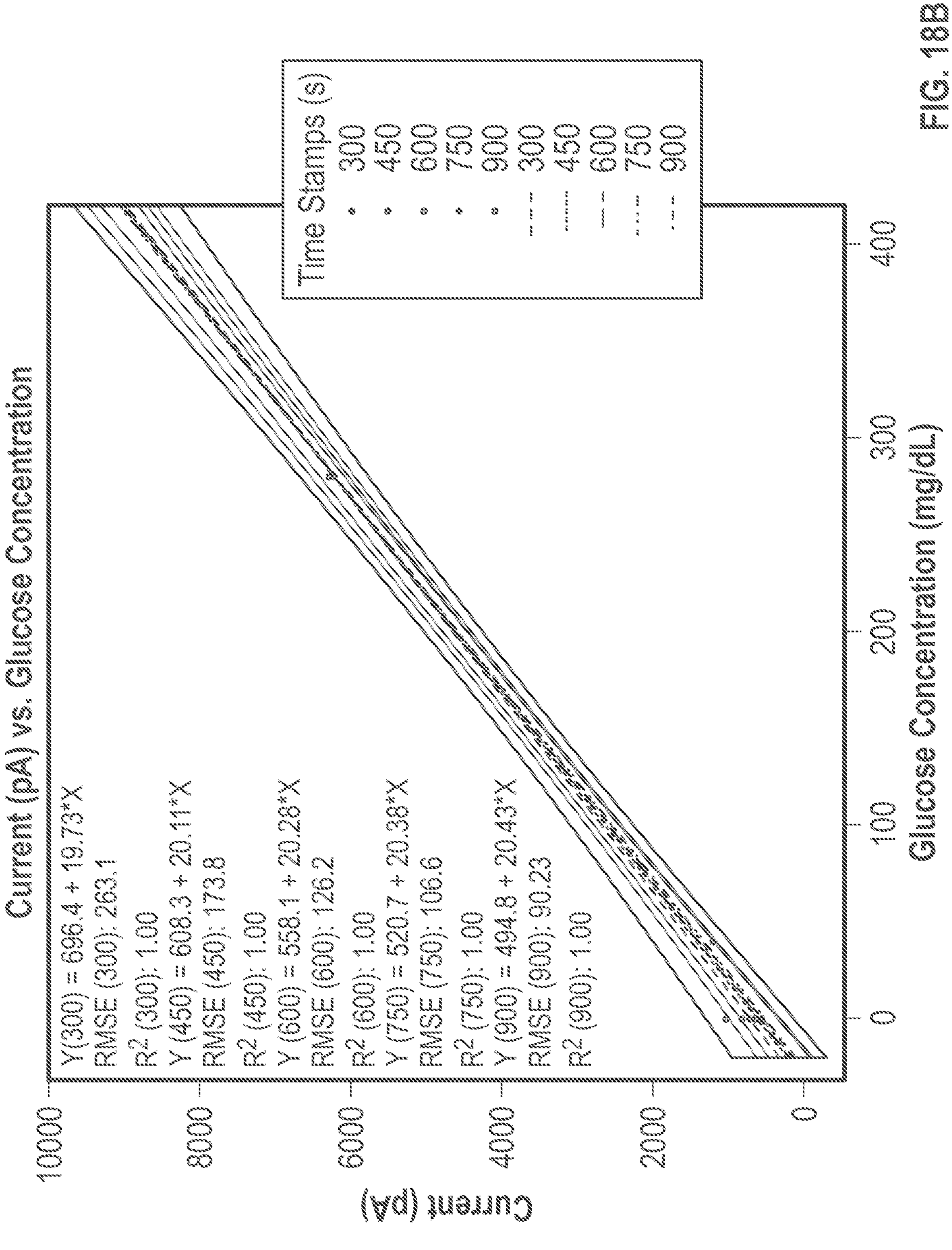

FIGS. 18A and 18B illustrate an example of transient raw current values corresponding to glucose concentrations at multiple times after the completion of measuring oxygen concentration. A steady bias voltage of 0.6 V is applied to the analyte sensor and the true glucose concentrations are measured at multiple times (300 sec, 450 s, 600 s, 750 s and 900 s) after the completion of measuring an oxygen concentration (i.e. after flipping the bias voltage). As show in FIG. 18A, the glucose raw current is collected at different time stamps after the flipping, i.e. 300 s, 450 s, 600 s, 750 s and 900 s. As show in FIG. 18B, the glucose current versus actual glucose concentration demonstrates a strong linear relationship at the glucose concentrations (0 mg/dL, 40 mg/dL, 160 mg/dL, 280 mg/dL and 400 mg/dL). The slope of the linear fits represented for the glucose sensitivity corresponds to the different time stamps.

Figure 19:
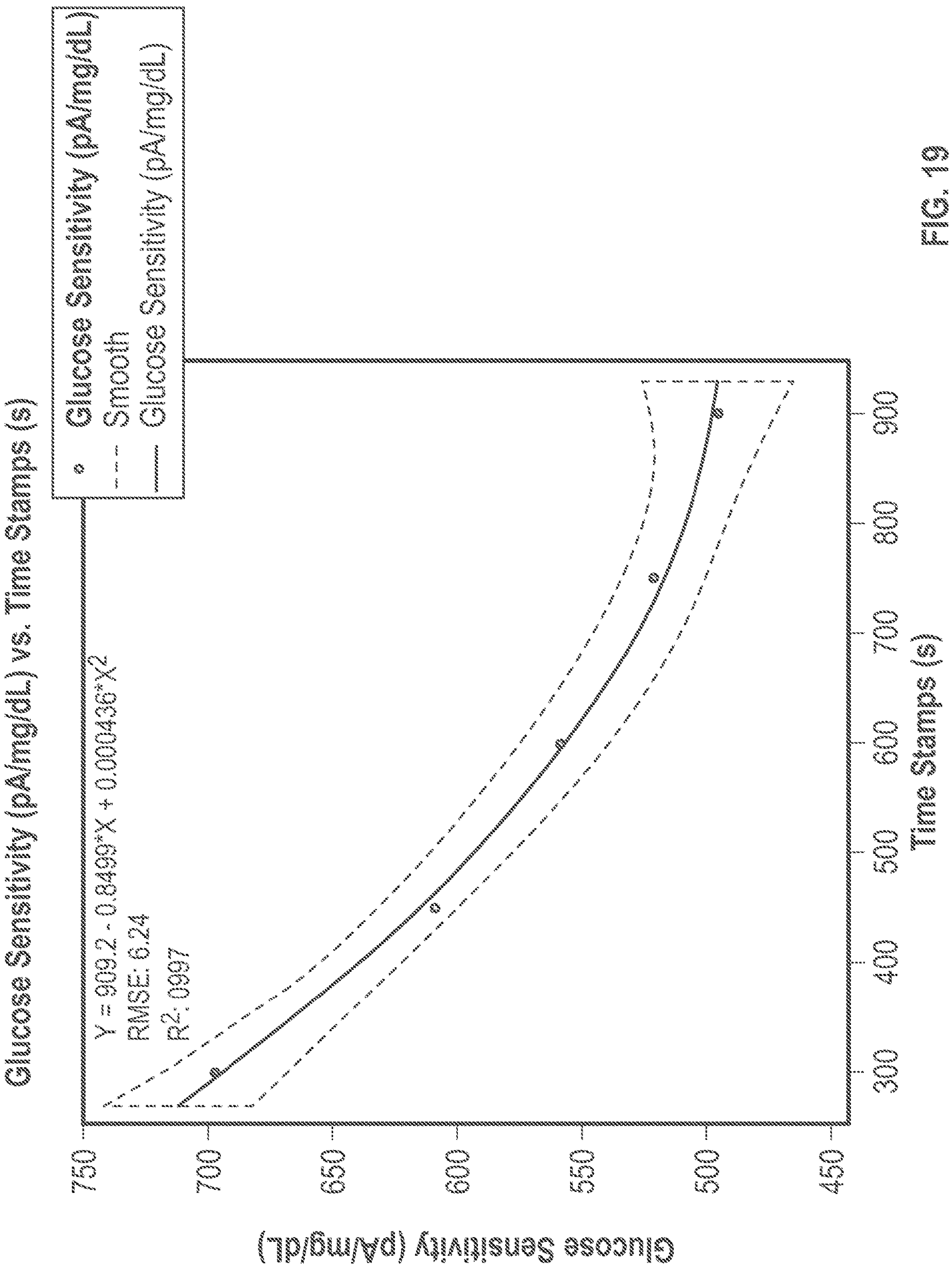
FIG. 19 illustrates an example of mathematical fitting of glucose sensitivity versus transient currents for several different time stamps.

FIG. 19 illustrates an example of mathematical fitting of glucose sensitivity versus transient currents for several different time stamps. This model allows the estimated glucose concentration level at steady state condition to be predicted by measuring the transient current and determining the time stamp. In other words, the transient current and time stand allow the glucose sensitivity to be extrapolated to provide estimated glucose concentration level prior to actually reaching steady state.

Figure 20A:
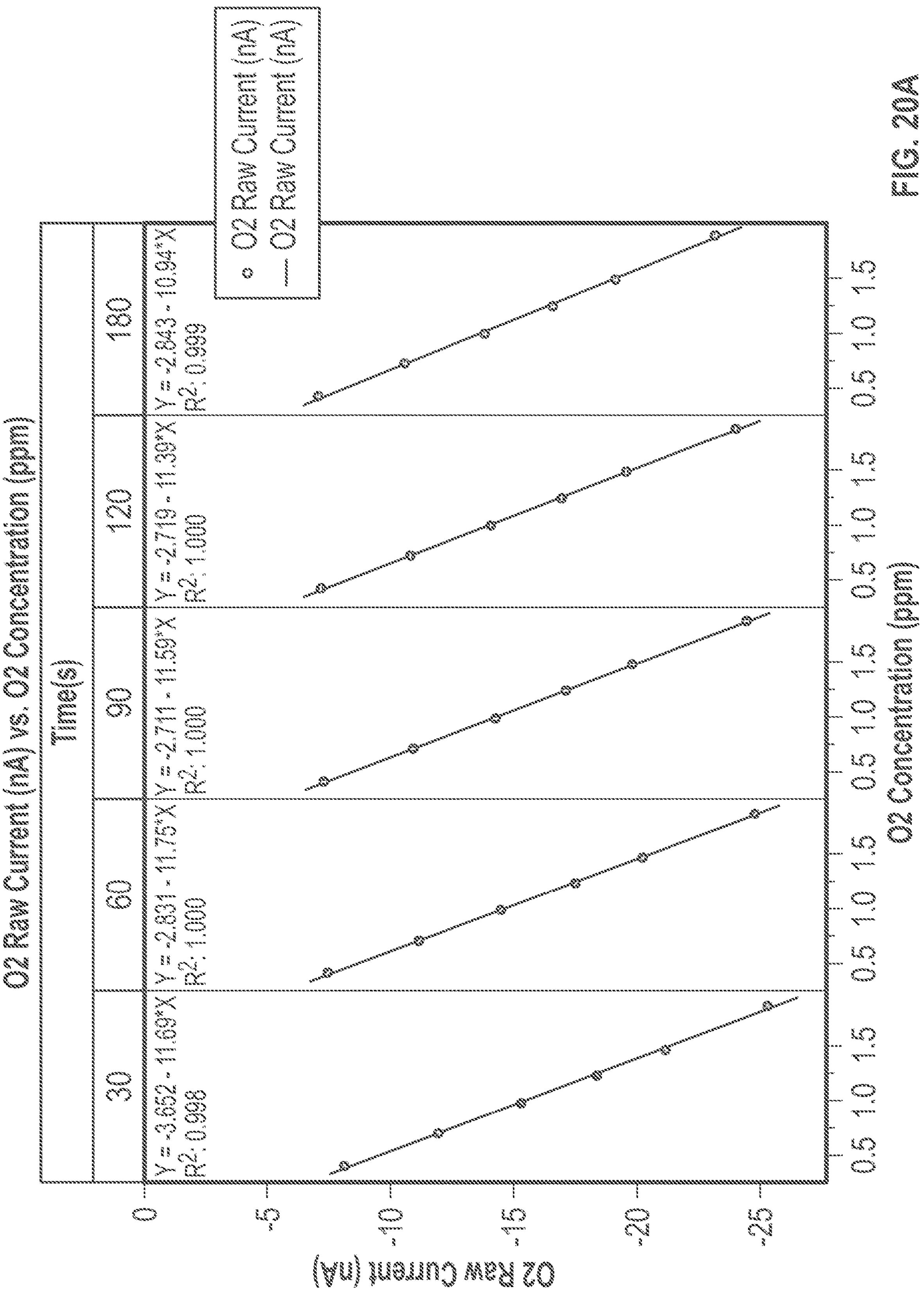
FIGS. 20A-20B illustrates an example of transient raw current values corresponding to oxygen concentrations at multiple times after the measurement of a glucose concentration.
Figure 20B:
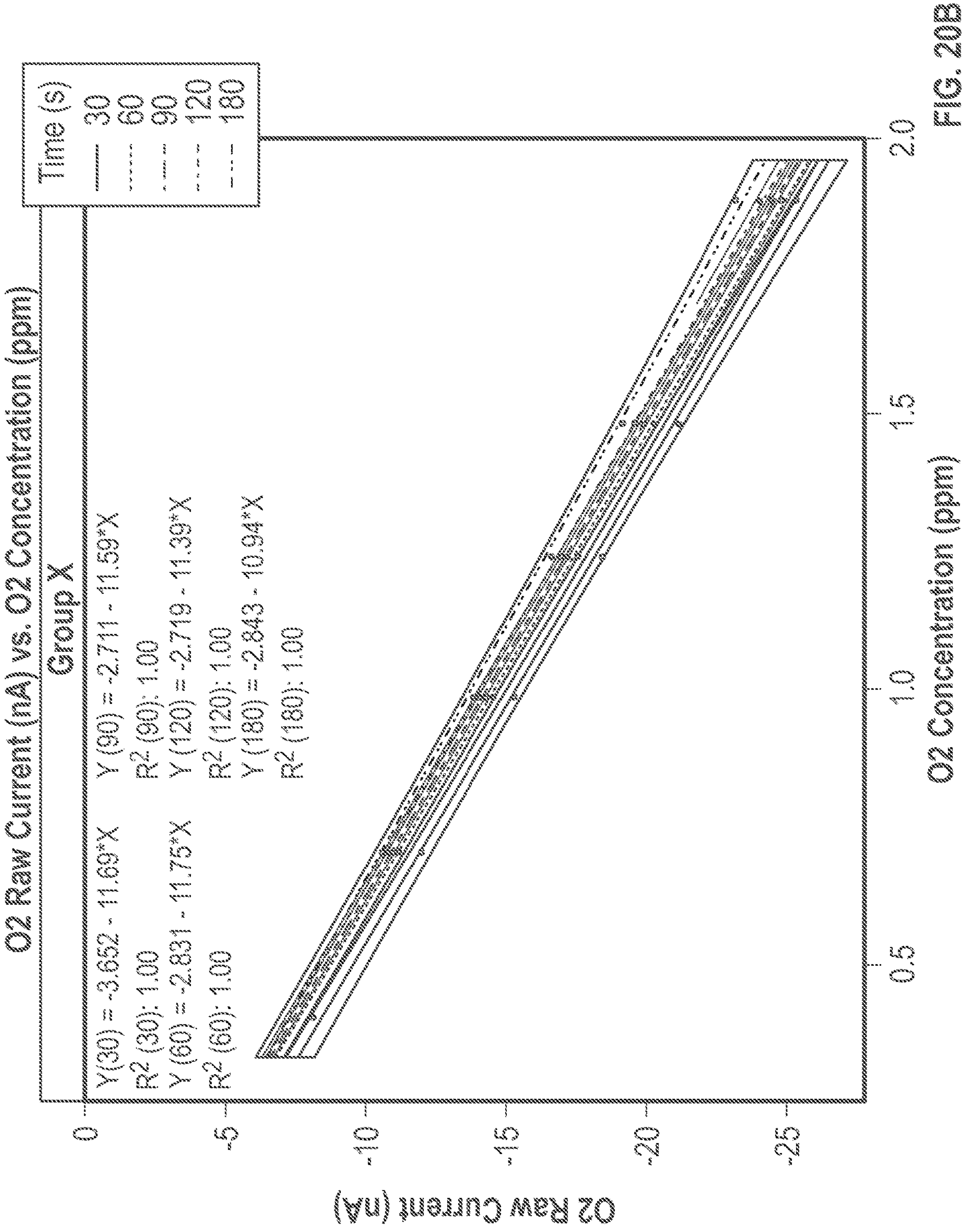

FIGS. 20A-20B illustrates an example of transient raw current values corresponding to oxygen concentrations at multiple times after the completion of measuring a glucose concentration. A steady bias voltage of −0.2 V is applied to the analyte sensor and the true oxygen concentrations are measured at multiple times (30 s, 60 s, 90 s, 120 s and 180 s) after the completion of measuring a glucose concentration (i.e. after flipping the bias voltage). As shown in FIG. 20B, the oxygen current versus actual oxygen concentration demonstrates a strong linear relationship at the oxygen concentrations between 0 and 2.0 ppm.

Figure 21:
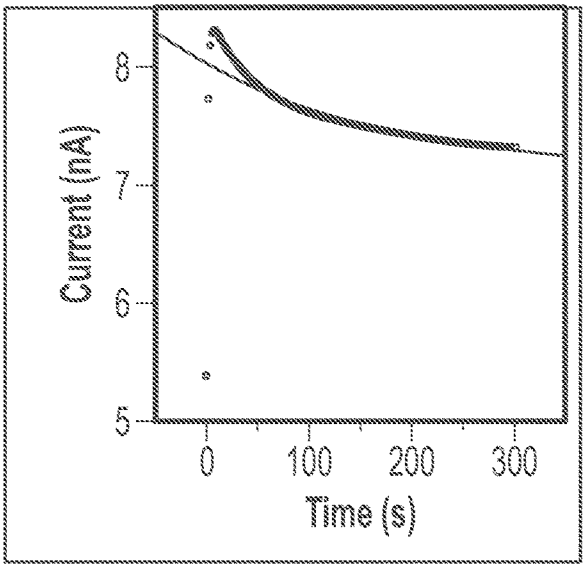
FIG. 21 illustrates an example of an exponential 3P decay plot that is used for fitting data to predict the glucose current decay after the flipping the bias voltage.

FIG. 21 illustrates an example of an exponential 3P decay plot that is used for fitting to predict the glucose current decay after the flipping the bias voltage. As shown in FIG. 21, the fitting model is extracted by using the raw data from 0 s to 300 s, and the prediction model is y=7.089+0.927*Exp (−0.00517*x); where x is the time in second. For example, as shown in FIG. 21, the predicted current at 824 s is 7.102 nA. The true data collected is 7.11 nA. Therefore, the error is within 0.2%.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

What is claimed is:

1. A continuous analyte monitoring system for measuring a concentration of a first analyte and a concentration of a second analyte in a host, the continuous analyte monitoring system comprising:
- a sensor comprising a working electrode extending along a central axis; and
- a reference electrode; and
- a sensor control circuit, the sensor control circuit configured to perform operations comprising:
  - performing a first measurement cycle comprising:
    - applying a first bias condition between the working electrode and the reference electrode, the first bias condition having a first polarity and a first magnitude;
    - accessing a first signal generated by the sensor in vivo while the first bias condition is applied, the first signal indicating the concentration of the first analyte;
    - applying a second bias condition between the working electrode and the reference electrode after applying the first bias condition, the second bias condition having a second polarity and a second magnitude, the second polarity being opposite the first polarity; and
    - accessing a second signal generated by the sensor in vivo while the second bias condition is applied, the second signal indicating the concentration of the second analyte, the second analyte being different than the first analyte;
  - performing a second measurement cycle comprising:
    - applying the first bias condition between the working electrode and the reference electrode during the second measurement cycle;
    - accessing a third signal generated by the sensor in vivo while the first bias condition is applied during the second measurement cycle;
    - applying the second bias condition between the working electrode and the reference electrode after applying the first bias condition during the second measurement cycle; and
    - accessing a fourth signal generated by the sensor in vivo while the second bias condition is applied during the second measurement cycle; and
  - applying, between the first measurement cycle and the second measurement cycle, a third bias condition between the working electrode and the reference electrode, the third bias condition being an overpotential relative to the first bias condition that is not used for generating a signal indicating the concentration of the first analyte or the concentration of the second analyte, the third bias condition having a third polarity and a third magnitude, the third polarity being equivalent to the first polarity and opposite the second polarity, and the third magnitude being greater than the first magnitude,
  - wherein the second measurement cycle is performed immediately following completion of the applying of the third bias condition.

2. The continuous analyte monitoring system of claim 1, wherein the first analyte is glucose or lactate and the second analyte is oxygen.

3. The continuous analyte monitoring system of claim 1, further comprising a counter electrode in electrical communication with the working electrode, the reference electrode, or both.

4. The continuous analyte monitoring system of claim 1, further comprising an enzyme layer at least partially covering the working electrode.

5. The continuous analyte monitoring system of claim 4, wherein the enzyme layer comprises an oxidase, dehydrogenase, or a mixture thereof.

6. The continuous analyte monitoring system of claim 4, further comprising a resistance layer at least partially covering the enzyme layer.

7. The continuous analyte monitoring system of claim 1, wherein the working electrode comprises platinum, palladium, rhodium, iridium, tantalum, or a mixture thereof and the reference electrode comprises silver and silver chloride.

8. The continuous analyte monitoring system of claim 1, the first polarity being positive from the working electrode to the reference electrode and the second polarity being negative from the working electrode to the reference electrode.

9. The continuous analyte monitoring system of claim 1, the first magnitude being between about 0.5 V and about 0.7 V.

10. The continuous analyte monitoring system of claim 1, the second magnitude being between about-0.3V and about-0.2V.

11. The continuous analyte monitoring system of claim 1, the third magnitude being between about 0.7V and to about 1.2V.

12. The continuous analyte monitoring system of claim 1, further comprising a transmitter capable of transmitting data obtained during the first bias condition, the second bias condition, the third bias condition, or a combination thereof to a device.

13. The continuous analyte monitoring system of claim 1, wherein the third bias condition is applied for an amount of time that is less than a time that each of the first bias condition and the second bias condition are applied.

14. The continuous analyte monitoring system of claim 1, wherein the first bias condition is applied for a time in a range of from about 4 minutes to about 80 minutes;

the second bias condition is applied for a time in range of from about 10 seconds to about 10 minutes; and the third bias condition is applied for a time in a range of from about 5 seconds to about 60 seconds.

15. The continuous analyte monitoring system of claim 1, wherein the first bias condition is applied for a time in a range of from about 4 minutes to about 30 minutes;

the second bias condition is applied for a time in range of from about 10 seconds to about 2 minutes; and the third bias condition is applied for a time in a range of from about 10 seconds to about 60 seconds.

16. The continuous analyte monitoring system of claim 1, wherein the second bias condition is applied for a time in range of from about 1 minute to about 10 minutes; and the third bias condition is applied for a time in a range of from about 10 seconds to about 60 seconds.

17. The continuous analyte monitoring system of claim 1, wherein the second bias condition is applied for a time in range of from about 1 minute to about 4 minutes; and the third bias condition is applied for a time in a range of from about 10 seconds to about 60 seconds.

18. The continuous analyte monitoring system of claim 1, wherein the second bias condition is applied for a time ranging from about 3 times to about 9 times greater than the third bias condition.

19. The continuous analyte monitoring system of claim 1, wherein the second bias condition is applied for a time ranging from about 5 times to about 7 times greater than the third bias condition.

20. The continuous analyte monitoring system of claim 1, further comprising a solid-state electrolyte layer at least partially covering at least one of the working electrode and the reference electrode.

21. The continuous analyte monitoring system of claim 20, wherein the solid-state electrolyte layer comprises a polyelectrolyte.

22. The continuous analyte monitoring system of claim 20, wherein the solid-state electrolyte layer is disposed between and in electrical communication with the working electrode and reference electrode.

* * * * *